US008080553B2

(12) United States Patent
Keith et al.

(10) Patent No.: US 8,080,553 B2
(45) Date of Patent: Dec. 20, 2011

(54) METHODS AND REAGENTS FOR THE TREATMENT OF IMMUNOINFLAMMATORY DISORDERS

(75) Inventors: Curtis Keith, Boston, MA (US); Alexis Borisy, Arlington, MA (US); Grant R. Zimmermann, Somerville, MA (US); Edward Roydon Jost-Price, West Roxbury, MA (US); Palaniyandi Manivasakam, West Roxbury, MA (US); Nicole Hurst, Boston, MA (US); Michael A. Foley, Chestnut Hill, MA (US); Michael S. Slavonic, Quincy, MA (US); Brendan Smith, Somerville, MA (US); Benjamin A. Auspitz, Cambridge, MA (US)

(73) Assignee: Zalicus Inc., Cambridge, MA (US)

( * ) Notice: Subject to any disclaimer, the term of this patent is extended or adjusted under 35 U.S.C. 154(b) by 1504 days.

(21) Appl. No.: 11/517,593

(22) Filed: Sep. 7, 2006

(65) Prior Publication Data
US 2007/0010502 A1 Jan. 11, 2007

Related U.S. Application Data

(63) Continuation of application No. 10/966,228, filed on Oct. 15, 2004, now abandoned.

(60) Provisional application No. 60/512,415, filed on Oct. 15, 2003.

(51) Int. Cl.
A01N 43/54 (2006.01)
A01N 43/90 (2006.01)
A61K 31/517 (2006.01)
A61K 31/519 (2006.01)
C07D 239/42 (2006.01)
C07D 401/04 (2006.01)

(52) U.S. Cl. .................................... 514/258.1; 514/256
(58) Field of Classification Search ................ 514/258.1, 514/256
See application file for complete search history.

(56) References Cited

U.S. PATENT DOCUMENTS

| | | | |
|---|---|---|---|
| 3,031,450 A | 4/1962 | Fischer et al. | |
| 3,934,036 A | 1/1976 | Irikura | |
| 3,944,577 A | 3/1976 | Laurent et al. | |
| 4,034,087 A | 7/1977 | Voorhees | |
| 4,107,306 A | 8/1978 | Voorhees | |
| 4,254,122 A * | 3/1981 | Brown | 514/245 |
| 4,367,217 A | 1/1983 | Gruber et al. | |
| 4,499,093 A | 2/1985 | Galabov et al. | |
| 4,554,271 A | 11/1985 | Braughler et al. | |
| 4,685,911 A | 8/1987 | Konno et al. | |
| 4,879,119 A | 11/1989 | Konno et al. | |
| 5,051,262 A | 9/1991 | Panoz et al. | |
| 5,242,921 A | 9/1993 | Milstone et al. | |
| 5,270,047 A | 12/1993 | Kauffman et al. | |
| 5,314,688 A | 5/1994 | Kauffman et al. | |
| 5,326,764 A | 7/1994 | Milstone et al. | |
| 5,428,040 A | 6/1995 | Magolda et al. | |
| 5,468,729 A | 11/1995 | Chretien et al. | |
| 5,639,759 A | 6/1997 | Magolda et al. | |
| 5,668,116 A | 9/1997 | Cullis-Hill et al. | |
| 5,728,712 A | 3/1998 | Montana et al. | |
| 5,756,553 A | 5/1998 | Iguchi et al. | |
| 5,762,918 A | 6/1998 | Thorpe | |
| 5,792,476 A | 8/1998 | Hallgren | |
| 5,874,437 A | 2/1999 | Garvey et al. | |
| 5,874,441 A | 2/1999 | Magolda et al. | |
| 5,958,926 A | 9/1999 | Garvey et al. | |
| 6,010,716 A | 1/2000 | Saunal et al. | |
| 6,015,577 A | 1/2000 | Eisert et al. | |
| 6,054,487 A | 4/2000 | Sekut et al. | |
| 6,071,514 A | 6/2000 | Grinnell et al. | |
| 6,110,910 A | 8/2000 | Magolda et al. | |
| 6,133,272 A | 10/2000 | Garvey et al. | |
| 6,172,060 B1 | 1/2001 | Garvey et al. | |
| 6,172,068 B1 | 1/2001 | Garvey et al. | |
| 6,177,428 B1 | 1/2001 | Garvey et al. | |
| 6,197,778 B1 | 3/2001 | Garvey et al. | |
| 6,197,782 B1 | 3/2001 | Garvey et al. | |
| 6,211,179 B1 | 4/2001 | Garvey et al. | |
| 6,221,881 B1 | 4/2001 | Garvey et al. | |
| 6,232,321 B1 | 5/2001 | Garvey et al. | |
| 6,265,427 B1 | 7/2001 | Camden | |
| 6,316,457 B1 | 11/2001 | Garvey et al. | |
| 6,331,543 B1 | 12/2001 | Garvey et al. | |
| 6,337,325 B1 | 1/2002 | Schonharting et al. | |
| 6,372,254 B1 | 4/2002 | Ting et al. | |
| 6,383,471 B1 | 5/2002 | Chen et al. | |
| 6,403,571 B2 | 6/2002 | Gould et al. | |
| 6,462,044 B2 | 10/2002 | Garvey et al. | |
| 6,515,010 B1 | 2/2003 | Franchini et al. | |
| 6,602,521 B1 | 8/2003 | Ting et al. | |
| 6,677,326 B2 | 1/2004 | Bardsley et al. | |
| 6,730,321 B2 | 5/2004 | Ting et al. | |
| 7,253,155 B2 | 8/2007 | Keith et al. | |

(Continued)

FOREIGN PATENT DOCUMENTS

CN 1246335 A 3/2000

(Continued)

OTHER PUBLICATIONS

Boileau et al. Arthritis & Rheumatism, 2002, vol. 46, No. 10, pp. 2637-2647.*

(Continued)

*Primary Examiner* — Sreeni Padmanabhan
*Assistant Examiner* — Samira Jean-Louis
(74) *Attorney, Agent, or Firm* — Clark & Elbing LLP

(57) ABSTRACT

The invention features a method for treating a patient diagnosed with, or at risk of developing, an immunoinflammatory disorder by administering to the patient a tetra-substituted pyrimidopyrimidine, either alone or in combination with one or more additional agents. The invention also features a composition containing a tetra-substituted pyrimidopyrimidine in combination with one or more additional agents.

22 Claims, No Drawings

U.S. PATENT DOCUMENTS

| | | | |
|---|---|---|---|
| 2001/0007083 | A1 | 7/2001 | Roorda et al. |
| 2001/0016604 | A1 | 8/2001 | Yu et al. |
| 2002/0019405 | A1 | 2/2002 | Garvey et al. |
| 2003/0003151 | A1 | 1/2003 | Chopra |
| 2003/0023087 | A1 | 1/2003 | Garvey et al. |
| 2003/0069169 | A1 | 4/2003 | Macor et al. |
| 2003/0077229 | A1 | 4/2003 | Dugger |
| 2003/0078246 | A1* | 4/2003 | Sackeyfio et al. ............ 514/171 |
| 2003/0203028 | A1 | 10/2003 | Ting et al. |
| 2004/0087486 | A1 | 5/2004 | Hanson |
| 2004/0087591 | A1 | 5/2004 | Garvey et al. |
| 2004/0180812 | A1 | 9/2004 | Dicker et al. |
| 2005/0019393 | A1 | 1/2005 | Augsburger et al. |
| 2005/0025713 | A1 | 2/2005 | Dugger |
| 2005/0037074 | A1 | 2/2005 | Ross et al. |
| 2005/0058688 | A1 | 3/2005 | Boerger et al. |
| 2005/0119160 | A1 | 6/2005 | Keith et al. |
| 2006/0234991 | A1 | 10/2006 | Keith et al. |
| 2007/0010502 | A1 | 1/2007 | Keith et al. |
| 2007/0196491 | A1 | 8/2007 | Venkatesh |
| 2007/0213296 | A1 | 9/2007 | Zhang |
| 2007/0213308 | A1 | 9/2007 | Lessem et al. |
| 2009/0075955 | A1 | 3/2009 | Padval |

FOREIGN PATENT DOCUMENTS

| | | |
|---|---|---|
| EP | 0 303 713 B1 | 5/1993 |
| EP | 0 543 653 A1 | 5/1993 |
| EP | 1 093 814 A1 | 4/2001 |
| GB | 2 292 079 | 2/1996 |
| WO | WO 89/10122 | 11/1989 |
| WO | WO 92/16226 | 10/1992 |
| WO | WO 98/19672 | 5/1998 |
| WO | WO 98/55142 | 12/1998 |
| WO | WO 99/16417 | 4/1999 |
| WO | WO 99/62537 | 12/1999 |
| WO | WO 00/12076 | 3/2000 |
| WO | WO 00/12497 | 3/2000 |
| WO | WO 00/59475 | 10/2000 |
| WO | WO 01/47572 A2 | 7/2001 |
| WO | WO 01/54679 A2 | 8/2001 |
| WO | WO 01/68056 | 9/2001 |
| WO | WO 02/22127 A1 | 3/2002 |
| WO | WO 02/069905 | 9/2002 |
| WO | WO 02/085304 A2 | 10/2002 |
| WO | WO 02/094227 A1 | 11/2002 |
| WO | WO 03/006026 | 1/2003 |
| WO | WO 03/030823 | 4/2003 |
| WO | WO 03/043603 A1 | 5/2003 |
| WO | WO 2004/019909 A2 | 3/2004 |
| WO | WO 2004/069254 A2 | 8/2004 |
| WO | WO 2005/020933 A2 | 3/2005 |
| WO | WO 2005/030132 | 4/2005 |
| WO | WO 2005/037203 | 4/2005 |
| WO | WO 2007/089617 | 8/2007 |
| WO | WO 2007/103373 | 9/2007 |

OTHER PUBLICATIONS

Forrest C M et al., "Adenosine and Cytokine Levels Following Treatment of Rheumatoid Arthritis with Dipyridamole", *Rheumatology International*. 27(1) 11-17 (2006).
Green, P G et al., "Purinergic Regulation of Bradykinin-Induced Plasma Extravasation and Adjuvant-Induced Arthritis in The Rat", *Proceedings of the National Academy of Sciences*, 88:10; 4162-4165 (1991).
European Search Report for EP09002049 dated Mar. 18, 2009.
Afeltra, "Treatment of Rheumatoid Arthritis: New Therapeutic Approaches with Biological Agents," *Curr. Drug Targets Immune. Endocr. Metabol. Disord.* 1:45-65 (2001).
Badger et al., "Disease-Modifying Activity of SB242235, A Selective Inhibitor of p38 Mitogen-Activated Protein Kinase, in Rat Adjuvant-Induced Arthritis," *Arthritis. Rheum.* 43:175-183 (2000).
Barlow et al., "Resistance-modifying agents. Part 7: 2,6-disubstituted-4,8-dibenzylaminopyrimido[5,4-*d*]pyrimidines that inhibit nucleoside transport in the presence of $\alpha_1$-acid glycoprotein (AGP)," *Bioorg. & Med. Chem. Lett.* 10:585-589 (2000).
Barnes, "Anti-inflammatory Actions of Glucocorticoids: Molecular Mechanisms," *Clin. Sci.* 94:557-572 (1998).
Baxter et al., "Mechanism of Glucocorticoid Action: General Features, with Reference to Steroid-Mediated Immunosuppression," *Transplant. Proc.* 7:55-65 (1975).
Berger et al., "Comparative Carcinogenic Activity of Prednimustine, Chlorambucil, Prednisolone and Chlorambucil Plus Prednisolone in Sprague-Dawley Rats," *Arch. Geschwulstforsch* 55:429-442 (1985).
Berger et al., "Long-Term Toxicology Effects of Prednimustine in Comparison with Chlorambucil, Prednisolone, and Chlorambucil Plus Prednisolone in Sprague-Dawley Rats," *Semin. Oncol.* 13:8-13 (1986).
Berkow et al., "The Merck Manual," fifteenth edition, pp. 797-807 (1987).
Berkow et al., "Merck Manual of Medical Information," Home edition, pp. 248-255 (1997).
Brunette et al., "Long-term Immunosuppressive Treatment of a Child with Takayasu's Arteritis and High IgE Immunoglobulins," *Pediatr. Nephrol.* 10:67-69 (1996).
Bruserud, "Dipyridamol Inhibits Activation of Human T Lymphocytes In Vitro," *Clin. Immunol. Immunopathol.* 42:102-109 (1987).
Cass et al., "A Comparison of the Abilities of Nitrobenzylthioinosine, Dilazep, and Dipyridamole to Protect Human Hematopoietic Cells From 7-Deazaadenosine (Tubercidin)," *Cancer Res.* 52:5879-5886 (1992).
Cazenave et al., "Inhibition of Platelet Adherence to a Collagen-coated Surface by Nonsteroidal Anti-inflammatory Drugs, Pyrimido-pyrimidine and Tricyclic Compounds, and Lidocaine" *J. Lab. Clin. Med.* 83:797-806 (1974).
Conway et al., "Inhibition of Cartilage and Bone Destruction in Adjuvant Arthritis in the Rat by a Matrix Metalloproteinase Inhibitor," *J. Exp. Med.* 182:449-457 (1995).
Curtin et al., "Potentiation of the Cytotoxicity of Thymidylate Synthase (TS) Inhibitors by Dipyridamole Analogues with Reduced $\alpha_1$-acid Glycoprotein Binding" *Br. J. Cancer* 80:1738-1746 (1999).
Eigler et al., "Endogenous Adenosine Curtails Lipopolysaccharide-Stimulated Tumour Necrosis Factor Synthesis," *Scan J. Immunol.* 45:132-139 (1997).
Feldmann et al., "Anti-TNFα Therapy of Rheumatoid Arthritis: What Have We Learned?" *Annu. Rev. Immunol.* 19:163-196 (2001).
Goh et al., "Nitrobenzylthioinosine-binding Protein Overexpression in Human Breast, Liver, Stomach and Colorectal Tumour Tissues," *Anticancer Res.* 15:2575-2580 (1995).
Griffon-Etienne et al., "Taxane-induced Apoptosis Decompresses Blood Vessels and Lowers Interstitial Fluid Pressure in Solid Tumors: Clinical Implications," *Cancer Res.* 59: 3776-3782 (1999).
Harada et al., "Renal Amyloidosis Associated with Crescentic Glomerulonephritis" *Am. J. Nephrol.* 4:52-55 (1984).
Haskó et al., "Adenosine Inhibits IL-12 and TNF-60 Production Via Adenosine $A_{2a}$ Receptor-Dependent and Independent Mechanisms," *FASEB J.* 14:2065-2074 (2000).
Iijima et al., "Multiple Combined Therapy for Severe Henoch-Schönlein Nephritis in Children," *Pediatr. Nephrol.* 12:244-248 (1998).
Konstantinov et al., "Interferon Response to Dipyridamole in Lupus Erythematosus Patients" *Br. J. Dermatol.* 121:59-63 (1989).
Lau et al., "Reduced Red Blood Cell Deformability in Patients with Rheumatoid Vasculitis. Improvement After In Vitro Treatment with Dipyridamole," *Arthritis & Rheum.* 38:248-253 (1995).
Le Vraux et al., "Inhibition of Human Monocyte TNF Production by Adenosine Receptor Agonists," *Life Sci.* 52:1917-1924 (1993).
Lehman et al., "Modulation of RTX Cytotoxicity by Thymidine and Dipyridamole In Vitro: Implications for Chemotherapy," *Cancer Chemother. Pharmacol.* 45:142-148 (2000).
Maezawa et al., "Combined Treatment with Cyclophosphamide and Prednisolone Can Induce Remission of Nephrotic Syndrome in a Patient with Renal Amyloidosis, Associated with Rheumatoid Arthritis," *Clin. Nephrol.* 42:30-32 (1994).
Mancini et al., "Inhibition of Tumor Necrosis Factor-α (TNF-α)/TNF-α Receptor Binding by Structural Analogues of Suramin," *Biochem. Pharmacol.* 58:851-859 (1999).
Milas et al., "Role of Reoxygenation in Induction of Enhancement of Tumor Radioresponse by Paclitaxel," *Cancer Res.* 55:3564-3568 (1995).

Milas et al., "Combination of Taxanes With Radiation: Preclinical Studies," *Semin. Radial. Oncology* 9:12-26 (1999).
Nenci et al., "Effects of Dipyridamole on the Hypoxemic Pulmonary Hypertension of Patients with Chronic Obstructive Pulmonary Disease," *Respiration* 53:13-19 (1988).
Rossi et al., "Thrombotic Thrombocytopenic Purpura," *JAMA* 228:1141-1143 (1974).
Ryrfeldt et al., "Liver Tumors in Male Rats Following Treatment with Glucocorticosteroids," *Toxicol. Pathol.* 20:115-117 (1992).
Sadamoto et al., "Thrombotic Thrombocytopenic Purpura in a Patient with a Diffuse Form of Systemic Sclerosis," *Jpn. J. Rheumatol.* 9:267-272 (1999).
Shinohara et al., "Corticosteroids in the Treatment of the Acute Phase of Kawasaki Disease," *J. Pediatr.* 135:465-469 (1999).
Simpson-Herren et al., "Diversity of Penetration of Anti-cancer Agents Into Solid Tumors," *Cell Prolif.* 24:355-365 (1991).
Solvay et al., "Atherosclerosis and Cerebral Ischemic Attacks: Intakes of Cerebrography with Xenon$^{133}$ Inhaled and Platelet Tests in the Diagnosis, Clinical and Therapeutic Monitoring: the Preventive Role of Dipyridamole," *Angiology* 35:709-717 (1984).
Takeda et al., "Long-Term Corticosteroid and Dipyridamole Treatment of Membranoproliferative Glomerulonephritis Type I in Children," *Jpn. J. Nephrol.* 37:330-335 (1995).
Tunggal et al., "Penetration of Anticancer Drugs Through Solid Tissue: A Factor That Limits the Effectiveness of Chemotherapy for Solid Tumors," *Clin. Cancer Res.* 5:1583-1586 (1999).
Wagner et al., "Adenosine Inhibits Lipopolysaccharide-Induced Cardiac Expression of Tumor Necrosis Factor-α," *Circ. Res.* 82:47-56 (1998).
Yoshikawa et al., "Combined Therapy with Prednisolone, Azathioprine, Heparin-Warfarin, and Dipyridamole for Paediatric Patients with Severe IgA Nephropathy—Is it Relevant for Adult Patients?" *Nephrol. Dial Transplant* 14:1097-1099 (1999).
Ziemnicka-Merchant et al., "Effects of Chemical Modification of Nitrobenzyl thioinosine on its Binding to High-Affinity Membrane Binding Sites and Inhibition of Nucleoside Transport," *Biochem. Pharmacol.* 44:1577-1583 (1992).
Zimmermann, "Plasmapheresis and Dipyridamole for Recurrent Focal Glomerular Sclerosis," *Nephron* 40:241-245 (1985).
Ardizzone et al., "Inflammatory Bowel Disease: New Insights Into Pathogenesis and Treatment," *J. Intern. Med.* 252:475-496 (2002).
Beck et al., "Increased Production of Interferon Gamma and Tumor Necrosis Factor Precedes Clinical Manifestation in Multiple Sclerosis: Do Cytokines Trigger Off Exacerbations?" *Acta. Neurol. Scand.* 78:318-323 (1988).
Braun et al. "Anti-Tumour Necrosis Factor α Therapy for Ankylosing Spondylitis: International Experience," *Ann. Rheum. Dis.* 61:iii51-iii60 (2002).
Braun et al., "Therapy of Ankylosing Spondylitis and Other Spondyloarthritides: Established Medical Treatment, Anti-TNF-α Therapy and Other Novel Approaches," *Arthritis Res.* 4:307-321 (2002).
Brown et al., "Acceptable Analytical Practices for Dissolution Testing of Poorly Soluble Compounds," *Pharm. Tech.* pp. 56-65 (Dec. 2004).
Crew et al., "Transgenic Mice Expressing a Truncated *Peromyscus leucopus* TNF-α Gene Manifest an Arthritis Resembling Ankylosing Spondylitis," *J. Interferon Cytokine Res.* 18:219-225 (1998).
Durie et al., "Collagen-Induced Arthritis as a Model of Rheumatoid Arthritis," *Clin. lmmunol. Immunopathol.* 73:11-18 (1994).
Edwards et al., "PEGylated Recombinant Human Soluble Tumour Necrosis Factor Receptor Type I (r-Hu-sTNF-RI): Novel High Affinity TNF Receptor Designed for Chronic Inflammatory Diseases," *Ann. Rheum. Dis.* 58(Supplement):173-181 (1999).
Ettehadi et al., "Elevated Tumour Necrosis Factor-Alpha (TNF-α) Biological Activity in Psoriatic Skin Lesions," *Clin. Exp. Immunol.* 96:146-151 (1994).
European Communication issued for EP Patent Application No. 02800923.1, dated Sep. 14, 2009.
Examination Report issued by Government of India Patent Office for Indian Patent Application No. 967/CHENP/2004, mailed Aug. 7, 2007.
Ganesan et al., "Therapeutic Inhibitors of Tumor Necrosis Factor in Crohn's Disease," *Curr. Op. Invest. Drugs* 3:1301-1306 (2002).
Gorman et al., "Treatment of Ankylosing Spondylitis by Inhibition of Tumor Necrosis Factor α," *N. Eng. J. Med.* 346:1349-1356 (2002).
Khoury et al., "Changes in Serum Levels of ICAM and TNF-R Correlate With Disease Activity in Multiple Sclerosis," *Neurology* 53:758 (1999).
Krueger et al., "Potential of Tumor Necrosis Factor Inhibitors in Psoriasis and Psoriatic Arthritis," *Arch. Dermatol.* 140:218-225 (2004).
Lichtenstein et al., "Is Infliximab Effective for Induction of Remission in Patients With Ulcerative Colitis?" *Inflamm. Bowel Dis.* 7:89-93 (2001).
Moreland et al., "Etanercept Therapy in Rheumatoid Arthritis," *Ann. Intern. Med.* 130:478-486 (1999).
Mpofu et al., "Anti-TNF-α Therapies: They are All the Same (Aren't They?)," *Rheumatology* 44:271-273 (2004).
Murch et al., "Location of Tumour Necrosis Factor α by Immunohistochemistry in Chronic Inflammatory Bowel Disease," *Gut* 34:1705-1709 (1993).
Nanda et al., "Etanercept: A Clinical Review of Current and Emerging Indications," *Expert. Opin. Pharmacother.* 5:1175-1186 (2004).
Nicolaus, B.J.R., *Decision Making in Drug Research: Symbiotic Approach to Drug Design*, New York: Raven Press, pp. 173-186 (1983).
Nikolaus et al., "Mechanisms in Failure of Infliximab for Crohn's Disease," *Lancet* 356:1475-1479 (2000).
Öner et al., "The Effect of Triple Therapy on Rapidly Progressive Type of Henoch-Schönlein Nephritis," *Pediatr. Nephrol.* 9:6-10 (1995).
Raza et al., "Anti-TNF Therapies in Rheumatoid Arthritis, Crohn's Disease, Sepsis, and Myelodysplastic Syndromes," *Microsc. Res. Techn.* 50:229-235 (2000).
Sandborn et al., "Etanercept for Active Crohn's Disease: A Randomized, Double-Blind, Placebo-Controlled Trial," *Gastroenterology* 121:1088-1094 (2001).
Sands et al., "Biological Therapies for Ulcerative Colitis," *Acta. Gastro-Enterologica Belgica* 64:205-209 (2001).
Schreiber et al., "Tumour Necrosis Factor α and Interleukin 1β in Relapse of Crohn's Disease," *Lancet* 353:459-461 (1999).
Selmaj et al., "Identification of Lymphotoxin and Tumor Necrosis Factor in Multiple Sclerosis Lesions," *J. Clin. Invest.* 87:949-954 (1991).
Sharief et al., "Association Between Tumor Necrosis Factor-α and Disease Progression in Patients with Multiple Sclerosis," *N. Eng. J. Med.* 325:467-472 (1991).
Shen et al., "Current Therapeutic Recommendations, Infliximab for Ulcerative Colitis," *J. Clin. Gastroenterol.* 38:741-745 (2004).
Shou et al., "Identification of Blood Biomarkers of Rheumatoid Arthritis by Transcript Profiling of Peripheral Blood Mononuclear Cells From the Rat Collagen-Induced Arthritis Model," *Arthritis Res. Ther.* 8:R28 (2006).
Sieper et al., "New Treatment Options in Ankylosing Spondylitis: a Role for Anti-TNFα Therapy," *Ann. Rheum. Dis.* 60:iii58-iii61 (2001).
Vladic et al., "Cerebrospinal Fluid and Serum Protein Levels of Tumour Necrosis Factor-Alpha (TNF-α), Interleukin-6 (IL-6) and Soluble Interleukin-6 Receptor (sIL-6Rgp80) in Multiple Sclerosis Patients," *Cytokine* 20:86-89 (2002).
Yoshikawa et al., "A Controlled Trial of Combined Therapy for Newly Diagnosed Severe Childhood IgA Nephropathy," *J. Am. Soc. Nephrol.* 10:101-109 (1999).
Vuolteenaho et al., "Effects of TNFα-Antagonists on Nitric Oxide Production in Human Cartilage," *Osteoarthritis and Cartilage* 10:327-332 (2002).
European Patent Office Communication Application No. 09002049.6 dated Jun. 6, 2011.

* cited by examiner

US 8,080,553 B2

METHODS AND REAGENTS FOR THE TREATMENT OF IMMUNOINFLAMMATORY DISORDERS

CROSS-REFERENCE TO RELATED APPLICATIONS

This application is a continuation application of and claims priority from U.S. patent application Ser. No. 10/966,228, filed Oct. 15, 2004, which claims benefit of the filing date of U.S. Provisional Application No. 60/512,415, filed Oct. 15, 2003, each of which is hereby incorporated by reference.

BACKGROUND OF THE INVENTION

The invention relates to the treatment of immunoinflammatory disorders.

Immunoinflammatory conditions are characterized by the inappropriate activation of the body's immune defenses. Rather than targeting infectious invaders, the immune response targets and damages the body's own tissues or transplanted tissues. The tissue targeted by the immune system varies with the disorder. For example, in multiple sclerosis, the immune response is directed against the neuronal tissue, while in Crohn's disease the digestive tract is targeted. Immunoinflammatory disorders affect millions of individuals and include conditions such as asthma, allergic intraocular inflammatory diseases, arthritis, atopic dermatitis, atopic eczema, diabetes, hemolytic anaemia, inflammatory dermatoses, inflammatory bowel or gastrointestinal disorders (e.g., Crohn's disease and ulcerative colitis), multiple sclerosis, myasthenia gravis, pruritis/inflammation, psoriasis, rheumatoid arthritis, cirrhosis, and systemic lupus erythematosus.

Current treatment regimens for immunoinflammatory disorders, transplanted organ rejection, and graft versus host disease typically rely on immunosuppressive agents. The effectiveness of these agents can vary and their use is often accompanied by adverse side effects. Thus, improved therapeutic agents and methods for the treatment of immunoinflammatory conditions are needed.

SUMMARY OF THE INVENTION

The invention features a method for treating an immunoinflammatory disease by administering to a patient in need thereof certain tetra-substituted pyrimidopyrimidines, either alone or in combination with any of a number of companion compounds, including an antihistamine, a corticosteroid, rolipram, ibudilast, a tricyclic or tetracyclic antidepressant, an SSRI, a non-steroidal anti-inflammatory drug, a non-steroidal immunophilin-dependent immunosuppressant, and an analog of any thereof, as described herein.

Accordingly, in one aspect, the invention features a method of treating a patient having an immunoinflammatory disease by administering to the patient a tetra-substituted pyrimidopyrimidine in an amount and for duration to treat the patient.

In a related aspect, the invention features a method for treating a patient having an immunoinflammatory disorder by administering to the patient tetra-substituted pyrimidopyrimidine and an antihistamine simultaneously or within 14 days of each other in amounts sufficient to treat the patient.

In another aspect, the invention features a method of decreasing proinflammatory cytokine secretion or production in a patient by administering to the patient a tetra-substituted pyrimidopyrimidine and an antihistamine simultaneously or within 14 days of each other in amounts sufficient to decrease proinflammatory cytokine secretion or production in the patient.

In another aspect, the invention features a composition that includes a tetra-substituted pyrimidopyrimidine and an antihistamine. A particularly desirable tetra-substituted pyrimidopyrimidine is dipyridamole. The composition may be formulated for topical or systemic administration.

In another aspect, the invention features a kit that includes: (i) a composition that includes a tetra-substituted pyrimidopyrimidine and an antihistamine; and (ii) instructions for administering the composition to a patient diagnosed with or at risk of developing an immunoinflammatory disorder.

In a related aspect, the invention features a kit that includes: (i) an antihistamine; (ii) a tetra-substituted pyrimidopyrimidine; and (iii) instructions for administering the tetra-substituted pyrimidopyrimidine and the antihistamine to a patient diagnosed with or at risk of developing an immunoinflammatory disorder.

In another aspect, the invention features a composition that includes a tetra-substituted pyrimidopyrimidine and a corticosteroid. Particularly desirable corticosteroids are prednisolone, cortisone, dexamethasone, hydrocortisone, methylprednisolone, fluticasone, prednisone, triamcinolone, and diflorasone. The composition may be formulated for topical or systemic administration (e.g., oral administration). One or both of the drugs may be present in the composition in a low dosage or a high dosage, each of which is defined herein.

In another aspect, the invention features a method of decreasing proinflammatory cytokine secretion or production in a patient by administering to the patient a tetra-substituted pyrimidopyrimidine and a corticosteroid simultaneously or within 14 days of each other in amounts sufficient to decrease proinflammatory cytokine secretion or production in the patient.

In a related aspect, the invention features a method for treating a patient diagnosed with or at risk of developing an immunoinflammatory disorder by administering to the patient a tetra-substituted pyrimidopyrimidine and a corticosteroid simultaneously or within 14 days of each other in amounts sufficient to treat the patient.

In another aspect, the invention features a kit that includes: (i) a composition that includes a tetra-substituted pyrimidopyrimidine and a corticosteroid; and (ii) instructions for administering the composition to a patient diagnosed with or at risk of developing an immunoinflammatory disorder.

In a related aspect, the invention features a kit that includes: (i) a tetra-substituted pyrimidopyrimidine; (ii) a corticosteroid; and (iii) instructions for administering the tetra-substituted pyrimidopyrimidine and the corticosteroid to a patient diagnosed with or at risk of developing an immunoinflammatory disorder.

In another aspect, the invention features a composition that includes tetra-substituted pyrimidopyrimidine and ibudilast. The composition may be formulated for topical or systemic administration.

In another aspect, the invention features a method of decreasing proinflammatory cytokine secretion or production in a patient by administering to the patient tetra-substituted pyrimidopyrimidine and ibudilast simultaneously or within 14 days of each other in amounts sufficient to decrease proinflammatory cytokine secretion or production in the patient.

In a related aspect, the invention features a method for treating a patient diagnosed with or at risk of developing an immunoinflammatory disorder by administering to the patient tetra-substituted pyrimidopyrimidine and ibudilast simultaneously or within 14 days of each other in amounts sufficient to treat the patient.

In another aspect, the invention features a kit that includes: (i) a composition that includes tetra-substituted pyrimidopyrimidine and ibudilast; and (ii) instructions for administering the composition to a patient diagnosed with or at risk of developing an immunoinflammatory disorder.

In a related aspect, the invention features a kit that includes: (i) tetra-substituted pyrimidopyrimidine; (ii) ibudilast; and (iii) instructions for administering the tetra-substituted pyrimidopyrimidine and the ibudilast to a patient diagnosed with or at risk of developing an immunoinflammatory disorder.

In another aspect, the invention features a composition that includes tetra-substituted pyrimidopyrimidine and rolipram. The composition may be formulated for topical or systemic administration.

In another aspect, the invention features a method of decreasing proinflammatory cytokine secretion or production in a patient by administering to the patient a tetra-substituted pyrimidopyrimidine and rolipram simultaneously or within 14 days of each other in amounts sufficient to decrease proinflammatory cytokine secretion or production in the patient.

In a related aspect, the invention features a method for treating a patient diagnosed with or at risk of developing an immunoinflammatory disorder by administering to the patient tetra-substituted pyrimidopyrimidine and rolipram simultaneously or within 14 days of each other in amounts sufficient to treat the patient.

In another aspect, the invention features a kit that includes: (i) a composition that includes tetra-substituted pyrimidopyrimidine and rolipram; and (ii) instructions for administering the composition to a patient diagnosed with or at risk of developing an immunoinflammatory disorder.

In a related aspect, the invention features a kit that includes: (i) tetra-substituted pyrimidopyrimidine; (ii) rolipram; and (iii) instructions for administering the tetra-substituted pyrimidopyrimidine and the rolipram to a patient diagnosed with or at risk of developing an immunoinflammatory disorder.

In another aspect, the invention features a composition that includes a tetra-substituted pyrimidopyrimidine and a tricyclic or tetracyclic antidepressant. Particularly desirable tricyclic or tetracyclic antidepressants are nortryptiline, amoxapine, and desipramine. The composition may be formulated for topical or systemic administration.

In another aspect, the invention features a method of decreasing proinflammatory cytokine secretion or production in a patient by administering to the patient a tetra-substituted pyrimidopyrimidine and a tricyclic or tetracyclic antidepressant simultaneously or within 14 days of each other in amounts sufficient to decrease proinflammatory cytokine secretion or production in the patient.

In a related aspect, the invention features a method for treating a patient diagnosed with or at risk of developing an immunoinflammatory disorder by administering to the patient a tetra-substituted pyrimidopyrimidine and a tricyclic or tetracyclic antidepressant simultaneously or within 14 days of each other in amounts sufficient to treat the patient.

In another aspect, the invention features a kit that includes: (i) a composition that includes a tetra-substituted pyrimidopyrimidine and a tricyclic or tetracyclic antidepressant; and (ii) instructions for administering the composition to a patient diagnosed with or at risk of developing an immunoinflammatory disorder. In a related aspect, the invention features a kit that includes: (i) a tetra-substituted pyrimidopyrimidine; (ii) a tricyclic or tetracyclic antidepressant; and (iii) instructions for administering the tetra-substituted pyrimidopyrimidine and the tricyclic or tetracyclic antidepressant to a patient diagnosed with or at risk of developing an immunoinflammatory disorder.

In another aspect, the invention features a composition that includes a tetra-substituted pyrimidopyrimidine and a selective serotonin reuptake inhibitor (SSRI). Particularly desirable SSRIs are paroxetine, fluoxetine, sertraline, and citalopram. The composition may be formulated for topical or systemic administration (e.g., oral administration).

In another aspect, the invention features a method of decreasing proinflammatory cytokine secretion or production in a patient by administering to the patient a tetra-substituted pyrimidopyrimidine and an SSRI simultaneously or within 14 days of each other in amounts sufficient to decrease proinflammatory cytokine secretion or production in the patient.

In a related aspect, the invention features a method for treating a patient diagnosed with or at risk of developing an immunoinflammatory disorder by administering to the patient an a tetra-substituted pyrimidopyrimidine and an SSRI simultaneously or within 14 days of each other in amounts sufficient to treat the patient.

In another aspect, the invention features a kit that includes: (i) a composition that includes a tetra-substituted pyrimidopyrimidine and an SSRI; and (ii) instructions for administering the composition to a patient diagnosed with or at risk of developing an immunoinflammatory disorder.

In a related aspect, the invention features a kit that includes: (i) a tetra-substituted pyrimidopyrimidine; (ii) an SSRI; and (iii) instructions for administering the antihistamine and the SSRI to a patient diagnosed with or at risk of developing an immunoinflammatory disorder.

In particular embodiments of any of the methods of the invention, the tetra-substituted pyrimidopyrimidine and the companion compound are administered within 10 days of each other, within five days of each other, within twenty-four hours of each other, or even simultaneously. The compounds may be formulated together as a single composition, or may be formulated and administered separately. One or both compounds may be administered in a low dosage or in a high dosage, each of which is defined herein. If desired, the composition, method, or kit may include one or more additional compounds (e.g., a glucocorticoid receptor modulator, NSAID, COX-2 inhibitor, DMARD, biologic, xanthine, small molecule immunomodulator, anticholinergic compound, beta receptor agonist, bronchodilator, non-steroidal immunophilin-dependent immunosuppressant, vitamin D analog, psoralen, retinoid, or 5-amino salicylic acid). The composition may be formulated, for example, for topical administration or systemic administration.

Combination therapies of the invention are especially useful for the treatment of immunoinflammatory disorders in combination with other anti-cytokine agents or agents that modulate the immune response to positively effect disease, such as agents that influence cell adhesion, or biologics or small molecules that block the action of IL-6, IL-1, IL-2, IL-12, IL-15 or TNFα (e.g., etanercept, adelimumab, infliximab, or CDP-870). In this example (that of agents blocking the effect of TNFα), the combination therapy reduces the production of cytokines, etanercept or infliximab act on the remaining fraction of inflammatory cytokines, providing enhanced treatment. Examples of small molecule agents that block cytokines or modulate immune response include agents inhibiting p38 MAP kinase (e.g., Doramapimod, SCIO-469, VX-702), ICE (e.g., Pralnacasan) and TACE (e.g., BMS-561392).

In any of the methods, compositions, and kits of the invention, analogs of certain compounds may be employed in lieu of the compounds themselves. Analogs of a tetra-substituted pyrimidopyrimidine and other compounds are described herein. Structural analogs of a compound (e.g, ibudilast) or class of compound (e.g., antihistamines) do not need to have the same activity as the compound or class to which it is related. Thus, an SSRI analog does not necessarily inhibit serotonin reuptake.

In a related aspect, the invention features a method for identifying combinations of compounds useful for suppressing the secretion of proinflammatory cytokines in a patient in need of such treatment, said method comprising the steps of: (a) contacting cells in vitro with a combination of a tetra-substituted pyrimidopyrimidine, an antihistamine, a corticosteroid, ibudilast, rolipram, a tricyclic or tetracyclic antidepressant, or an SSRI and a candidate compound; and (b) determining whether the combination reduces cytokine levels in blood cells stimulated to secrete the cytokines relative to cells contacted with the tetra-substituted pyrimidopyrimidine, antihistamine, corticosteroid, ibudilast, rolipram, tricyclic or tetracyclic antidepressant, or SSRI but not contacted with the candidate compound or cells contacted with the candidate compound but not with the tetra-substituted pyrimidopyrimidine, antihistamine, corticosteroid, ibudilast, rolipram, tricyclic or tetracyclic antidepressant, or SSRI, wherein a reduction of cytokine levels identifies the combination as a combination that is useful for treating a patient in need of such treatment.

In a related aspect, the invention features a method for suppressing secretion of one or more proinflammatory cytokines in a cell by contacting the cell with: (i) a tetra-substituted pyrimidopyrimidine; and (ii) an antihistamine, a corticosteroid, ibudilast, rolipram, a tricyclic or tetracyclic antidepressant, or an SSRI simultaneously or within 14 days of each other in amounts sufficient to suppress secretion of one or more proinflammatory cytokines in the cell. The preferred cytokines are TNFα, IL-1, IL-2 and INF-γ.

In another aspect, the invention features a composition that includes an antihistamine, a corticosteroid, rolipram, ibudilast, a tricyclic or tetracyclic antidepressant, an SSRI, a non-steroidal anti-inflammatory drug, a non-steroidal immunophilin-dependent immunosuppressant, or an analog of any thereof; and (ii) a compound selected from the group consisting of a xanthine, small molecule immunomodulator, anticholinergic compound, biologic, DMARD, COX-2 inhibitor, beta-receptor agonist, bronchodilator, non-steroidal immunophilin-dependent immunosuppressant, vitamin D analog, psoralen, retinoid, or 5-amino salicylic acid.

In another aspect, the invention features a method of decreasing proinflammatory cytokine secretion or production in a patient by administering to a patient a tetra-substituted pyrimidopyrimidine or an analog thereof and an NSAID or an analog thereof simultaneously or within 14 days of each other in amounts sufficient to decrease proinflammatory cytokine secretion or production in the patient, with the proviso that when tetra-substituted pyrimidopyrimidine is dipyridamole, the NSAID is not aspirin.

In yet another aspect, the invention features a method for treating a patient diagnosed with or at risk of developing an immunoinflammatory disorder by administering to the patient a tetra-substituted pyrimidopyrimidine or an analog thereof and an NSAID or an analog thereof simultaneously or within 14 days of each other in amounts sufficient to treat the patient, with the proviso that when tetra-substituted pyrimidopyrimidine is dipyridamole, the NSAID is not aspirin.

In one aspect, the invention features a composition comprising a unit dose form of a tetra-substituted pyrimidopyrimidine and a second compound selected from an NSAID, COX-2 inhibitor, biologic, small molecule immunomodulator, DMARD, xanthine, anticholinergic compound, beta receptor agonist, bronchodilator, non-steroidal immunophilin-dependent immunosuppressant, vitamin D analog, psoralen, retinoid, and 5-amino salicylic acid with the proviso that when tetra-substituted pyrimidopyrimidine is dipyridamole, the second compound is not methotrexate or aspirin. The unit dose form this composition can be oral, topical, parenteral, rectal, cutaneous, nasal, vaginal, inhalant, skin (patch), or ocular administration.

The invention also features a method for inhibiting proinflammatory cytokine activity in a patient suffering from or at risk of suffering from a disorder associated with at least one immunoinflammatory disorder mediated by the cytokine by administering to the patient a unit dose of a tetra-substituted pyrimidopyrimidine in an amount effective to inhibit or decrease the cytokine activity in the patient, wherein when the tetra-substituted pyrimidopyrimidine is dipyridamole, the unit dose is suitable for systemic administration. The cytokine is desirably selected from TNFα, IL-1, IL-2, IL-6, IL-12, IL-15, and IFN-γ.

The methods and compositions of the invention desirably have increased effectiveness, safety, tolerability, or satisfaction of treatment of a patient suffering from or at risk of suffering from immunoinflammatory disorder, as compared to methods and compositions using each component of the combination individually.

Particularly useful tetra-substituted pyrimidopyrimidines for use in the methods, kits, and compositions of the invention are dipyridamole (also known as 2,6-bis(diethanolamino)-4, 8-dipiperidinopyrimido(5,4-d)pyrimidine); 2,6-disubstituted 4,8-dibenzylaminopyrimido[5,4-d]pyrimidines; mopidamole; dipyridamole monoacetate; NU3026 (2,6-di-(2,2-dimethyl-1,3-dioxolan-4-yl)-methoxy-4,8-di-piperidinopyrimidopyrimidine); NU3059 (2,6-bis-(2,3-dimethyoxypropoxy)-4,8-di-piperidinopyrimidopyrimidine); NU3060 (2,6-bis[N,N-di(2-methoxy)ethyl]-4,6-di-piperidinopyrimidopyrimidine); and NU3076 (2,6-bis(diethanolamino)-4,8-di-4-methoxybenzylaminopyrimidopyrimidine). Other tetra-substituted pyrimidopyrimidines are described in U.S. Pat. Nos. 3,031,450 and 4,963,541, hereby incorporated by reference.

By "corticosteroid" is meant any naturally occurring or synthetic compound characterized by a hydrogenated cyclopentanoperhydrophenanthrene ring system. Naturally occurring corticosteroids are generally produced by the adrenal cortex. Synthetic corticosteroids may be halogenated. Exemplary corticosteroids are described herein.

By "tricyclic or tetracyclic antidepressant" is meant a compound having one the formulas (I), (II), (III), or (IV):

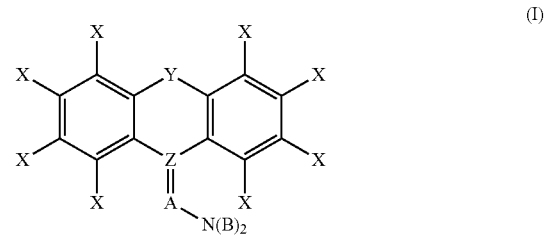

(I)

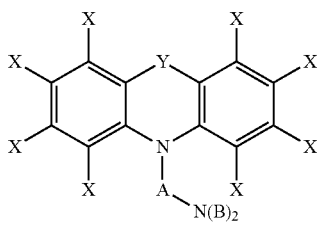
(II)

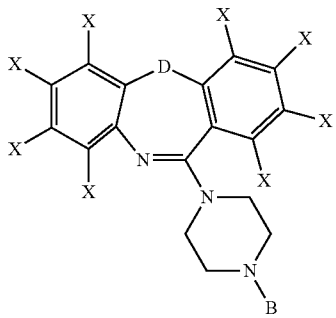
(III)

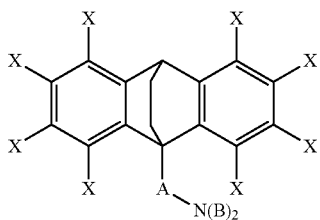
(IV)

wherein each X is, independently, H, Cl, F, Br, I, CH$_3$, CF$_3$, OH, OCH$_3$, CH$_2$CH$_3$, or OCH$_2$CH$_3$; Y is CH$_2$, O, NH, S(O)$_{0-2}$, (CH$_2$)$_3$, (CH)$_2$, CH$_2$O, CH$_2$NH, CHN, or CH$_2$S; Z is C or S; A is a branched or unbranched, saturated or monounsaturated hydrocarbon chain having between 3 and 6 carbons, inclusive; each B is, independently, H, Cl, F, Br, I, CX$_3$, CH$_2$CH$_3$, OCX$_3$, or OCX$_2$CX$_3$; and D is CH$_2$, O, NH, S(O)$_{0-2}$. In preferred embodiments, each X is, independently, H, Cl, or F; Y is (CH$_2$)$_2$, Z is C; A is (CH$_2$)$_3$; and each B is, independently, H, Cl, or F.

By "tetra-substituted pyrimidopyrimidine" is meant a compound having the formula (V):

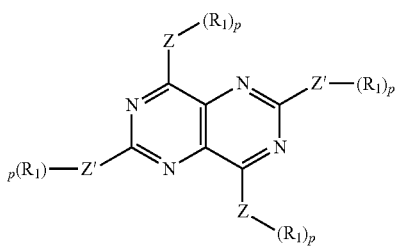
(V)

wherein each Z and each Z' is, independently, N, O, C,

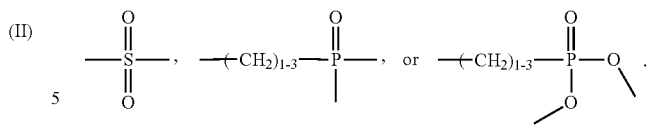

When Z or Z' is O or

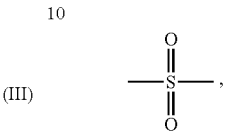

then p=1, when Z or Z' is N,

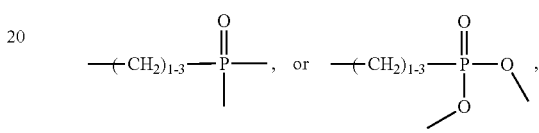

then p=2, and when Z or Z' is C, then p=3. In formula (V), each R$_1$ is, independently, X, OH, N-alkyl (wherein the alkyl group has 1 to 20, more preferably 1-5, carbon atoms); a branched or unbranched alkyl group having 1 to 20, more preferably 1-5, carbon atoms; or a heterocycle, preferably as defined in formula (Y), below. Alternatively, when p>1, two R$_1$ groups from a common Z or Z' atom, in combination with each other, may represent —(CY$_2$)$_k$— in which k is an integer between 4 and 6, inclusive. Each X is, independently, Y, CY$_3$, C(CY$_3$)$_3$, CY$_2$CY$_3$, (CY$_2$)$_{1-5}$OY, substituted or unsubstituted cycloalkane of the structure C$_n$Y$_{2n-1}$, wherein n=3-7, inclusive. Each Y is, independently, H, F, Cl, Br, or I. In one embodiment, each Z is the same moiety, each Z' is the same moiety, and Z and Z' are different moieties, By "antihistamine" is meant a compound that blocks the action of histamine. Classes of antihistamines include but are not limited to ethanolamines, ethylenediamines, phenothiazines, alkylamines, piperazines, and piperidines.

By "selective serotonin reuptake inhibitor" or "SSRI" is meant any member of the class of compounds that (i) inhibit the uptake of serotonin by neurons of the central nervous system, (ii) have an inhibition constant (Ki) of 10 nM or less, and (iii) a selectivity for serotonin over norepinephrine (i.e., the ratio of Ki(norepinephrine) over Ki(serotonin)) of greater than 100. Typically, SSRIs are administered in dosages of greater than 10 mg per day when used as antidepressants. Exemplary SSRIs for use in the invention are fluoxetine, fluvoxamine, paroxetine, sertraline, citalopram, and venlafaxine.

By "non-steroidal immunophilin-dependent immunosuppressant" or "NsIDI" is meant any non-steroidal agent that decreases proinflammatory cytokine production or secretion, binds an immunophilin, or causes a down regulation of the proinflammatory reaction. NsIDIs include calcineurin inhibitors, such as cyclosporine, tacrolimus, ascomycin, pimecrolimus, as well as other agents (peptides, peptide fragments, chemically modified peptides, or peptide mimetics) that inhibit the phosphatase activity of calcineurin. NsIDIs also include rapamycin (sirolimus) and everolimus, which bind to an FK506-binding protein, FKBP-12, and block antigen-induced proliferation of white blood cells and cytokine secretion.

By "small molecule immunomodulator" is meant a nonsteroidal, non-NsIDI compound that decreases proinflammatory cytokine production or secretion, causes a down regulation of the proinflammatory reaction, or otherwise modulates the immune system in an immunophilin-independent manner. Examplary small molecule immunomodulators are p38 MAP kinase inhibitors such as VX 702 (Vertex Pharmaceuticals), SCIO 469 (Scios), doramapimod (Boehringer Ingelheim), RO 30201195 (Roche), and SCIO 323 (Scios), TACE inhibitors such as DPC 333 (Bristol Myers Squibb), ICE inhibitors such as pranalcasan (Vertex Pharmaceuticals), and IMPDH inhibitors such as mycophenolate (Roche) and merimepodib (Vertex Pharamceuticals).

By a "low dosage" is meant at least 5% less (e.g., at least 10%, 20%, 50%, 80%, 90%, or even 95%) than the lowest standard recommended dosage of a particular compound formulated for a given route of administration for treatment of any human disease or condition. For example, a low dosage of corticosteroid formulated for administration by inhalation will differ from a low dosage of corticosteroid formulated for oral administration.

By a "high dosage" is meant at least 5% (e.g., at least 10%, 20%, 50%, 100%, 200%, or even 300%) more than the highest standard recommended dosage of a particular compound for treatment of any human disease or condition.

By a "moderate dosage" is meant the dosage between the low dosage and the high dosage.

By "treating" is meant administering or prescribing a composition for the treatment or prevention of an immunoinflammatory disease.

By "patient" is meant any animal (e.g., a human). Other animals that can be treated using the methods, compositions, and kits of the invention include horses, dogs, cats, pigs, goats, rabbits, hamsters, monkeys, guinea pigs, rats, mice, lizards, snakes, sheep, cattle, fish, and birds.

By "an amount sufficient" is meant the amount of a compound, in a combination of the invention, required to treat or prevent an immunoinflammatory disease in a clinically relevant manner. A sufficient amount of an active compound used to practice the present invention for therapeutic treatment of conditions caused by or contributing to an immunoinflammatory disease varies depending upon the manner of administration, the age, body weight, and general health of the patient. Ultimately, the prescribers will decide the appropriate amount and dosage regimen. Additionally, an effective amount may can be that amount of compound in the combination of the invention that is safe and efficacious in the treatment of a patient having the immunoinflammatory disease over each agent alone as determined and approved by a regulary authority (such as the U.S. Food and Drug Administration).

By "more effective" is meant that a method, composition, or kit exhibits greater efficacy, is less toxic, safer, more convenient, better tolerated, or less expensive, or provides more treatment satisfaction than another method, composition, or kit with which it is being compared. Efficacy may be measured by a skilled practitioner using any standard method that is appropriate for a given indication.

The term "immunoinflammatory disorder" encompasses a variety of conditions, including autoimmune diseases, proliferative skin diseases, and inflammatory dermatoses. Immunoinflammatory disorders result in the destruction of healthy tissue by an inflammatory process, dysregulation of the immune system, and unwanted proliferation of cells. Examples of immunoinflammatory disorders are acne *vulgaris*; acute respiratory distress syndrome; Addison's disease; allergic rhinitis; allergic intraocular inflammatory diseases, ANCA-associated small-vessel vasculitis; ankylosing spondylitis; arthritis, asthma; atherosclerosis; atopic dermatitis; autoimmune hemolytic anemia; autoimmune hepatitis; Behcet's disease; Bell's palsy; bullous pemphigoid; cerebral ischaemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; erythema nodosum; exfoliative dermatitis; fibromyalgia; focal glomerulosclerosis; giant cell arteritis; gout; gouty arthritis; graft-versus-host disease; hand eczema; Henoch-Schonlein purpura; herpes gestationis; hirsutism; idiopathic cerato-scleritis; idiopathic pulmonary fibrosis; idiopathic thrombocytopenic purpura; inflammatory bowel or gastrointestinal disorders, inflammatory dermatoses; lichen planus; lupus nephritis; lymphomatous tracheobronchitis; macular edema; multiple sclerosis; myasthenia gravis; myositis; osteoarthritis; pancreatitis; pemphigoid gestationis; pemphigus *vulgaris*; polyarteritis nodosa; polymyalgia rheumatica; pruritus scroti; pruritis/inflammation, psoriasis; psoriatic arthritis; rheumatoid arthritis; relapsing polychondritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; shoulder tendinitis or bursitis; Sjogren's syndrome; Still's disease; stroke-induced brain cell death; Sweet's disease; systemic lupus erythematosus; systemic sclerosis; Takayasu's arteritis; temporal arteritis; toxic epidermal necrolysis; tuberculosis; type-1 diabetes; ulcerative colitis; uveitis; vasculitis; and Wegener's granulomatosis.

"Non-dermal inflammatory disorders" include, for example, rheumatoid arthritis, inflammatory bowel disease, asthma, and chronic obstructive pulmonary disease.

"Dermal inflammatory disorders" or "inflammatory dermatoses" include, for example, psoriasis, acute febrile neutrophilic dermatosis, eczema (e.g., asteatotic eczema, dyshidrotic eczema, vesicular palmoplantar eczema), balanitis circumscripta plasmacellularis, balanoposthitis, Behcet's disease, erythema annulare centrifugum, erythema dyschromicum perstans, erythema multiforme, granuloma annulare, lichen nitidus, lichen planus, lichen sclerosus et atrophicus, lichen simplex chronicus, lichen spinulosus, nummular dermatitis, pyoderma gangrenosum, sarcoidosis, subcorneal pustular dermatosis, urticaria, and transient acantholytic dermatosis.

By "proliferative skin disease" is meant a benign or malignant disease that is characterized by accelerated cell division in the epidermis or dermis. Examples of proliferative skin diseases are psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant keratosis, acne, and seborrheic dermatitis.

As will be appreciated by one skilled in the art, a particular disease, disorder, or condition may be characterized as being both a proliferative skin disease and an inflammatory dermatosis. An example of such a disease is psoriasis.

By "sustained release" or "controlled release" is meant that the therapeutically active component is released from the formulation at a controlled rate such that therapeutically beneficial blood levels (but below toxic levels) of the component are maintained over an extended period of time ranging from e.g., about 12 to about 24 hours, thus, providing, for example, a 12 hour or a 24 hour dosage form.

In the generic descriptions of compounds of this invention, the number of atoms of a particular type in a substituent group is generally given as a range, e.g., an alkyl group containing from 1 to 7 carbon atoms or $C_{1-7}$ alkyl. Reference to such a range is intended to include specific references to groups having each of the integer number of atoms within the specified range. For example, an alkyl group from 1 to 7 carbon atoms includes each of $C_1$, $C_2$, $C_3$, $C_4$, $C_5$, $C_6$, and $C_7$. A $C_{1-7}$ heteroalkyl, for example, includes from 1 to 7 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Cyclic groups can be monocyclic or polycyclic and preferably have from 3 to 6 ring carbon atoms, inclusive. Exemplary cyclic groups include cyclopropyl, cyclobutyl, cyclopentyl, and cyclohexyl groups. The $C_{1-7}$ alkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{1-7}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; cyclobutyl; cyclobutylmethyl; cyclobutylethyl; n-pentyl; cyclopentyl; cyclopentylmethyl; cyclopentylethyl; 1-methylbutyl; 2-methylbutyl; 3-methylbutyl; 2,2-dimethylpropyl; 1-ethylpropyl; 1,1-dimethylpropyl; 1,2-dimethylpropyl; 1-methylpentyl; 2-methylpentyl; 3-methylpentyl; 4-methylpentyl; 1,1-dimethylbutyl; 1,2-dimethylbutyl; 1,3-dimethylbutyl; 2,2-dimethylbutyl; 2,3-dimethylbutyl; 3,3-dimethylbutyl; 1-ethylbutyl; 2-ethylbutyl; 1,1,2-trimethylpropyl; 1,2,2-trimethylpropyl; 1-ethyl-1-methylpropyl; 1-ethyl-2-methylpropyl; and cyclohexyl.

By "$C_{2-7}$ alkenyl" is meant a branched or unbranched hydrocarbon group containing one or more double bonds and having from 2 to 7 carbon atoms. A $C_{2-7}$ alkenyl may optionally include monocyclic or polycyclic rings, in which each ring desirably has from three to six members. The $C_{2-7}$ alkenyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, carboxyalkyl, and carboxyl groups. $C_{2-7}$ alkenyls include, without limitation, vinyl; allyl; 2-cyclopropyl-1-ethenyl; 1-propenyl; 1-butenyl; 2-butenyl; 3-butenyl; 2-methyl-1-propenyl; 2-methyl-2-propenyl; 1-pentenyl; 2-pentenyl; 3-pentenyl; 4-pentenyl; 3-methyl-1-butenyl; 3-methyl-2-butenyl; 3-methyl-3-butenyl; 2-methyl-1-butenyl; 2-methyl-2-butenyl; 2-methyl-3-butenyl; 2-ethyl-2-propenyl; 1-methyl-1-butenyl; 1-methyl-2-butenyl; 1-methyl-3-butenyl; 2-methyl-2-pentenyl; 3-methyl-2-pentenyl; 4-methyl-2-pentenyl; 2-methyl-3-pentenyl; 3-methyl-3-pentenyl; 4-methyl-3-pentenyl; 2-methyl-4-pentenyl; 3-methyl-4-pentenyl; 1,2-dimethyl-1-propenyl; 1,2-dimethyl-1-butenyl; 1,3-dimethyl-1-butenyl; 1,2-dimethyl-2-butenyl; 1,1-dimethyl-2-butenyl; 2,3-dimethyl-2-butenyl; 2,3-dimethyl-3-butenyl; 1,3-dimethyl-3-butenyl; 1,1-dimethyl-3-butenyl and 2,2-dimethyl-3-butenyl.

By "$C_{2-7}$ alkynyl" is meant a branched or unbranched hydrocarbon group containing one or more triple bonds and having from 2 to 7 carbon atoms. A $C_{2-7}$ alkynyl may optionally include monocyclic, bicyclic, or tricyclic rings, in which each ring desirably has five or six members. The $C_{2-7}$ alkynyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. $C_{2-7}$ alkynyls include, without limitation, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, 5-hexynyl; 1-methyl-2-propynyl; 1-methyl-2-butynyl; 1-methyl-3-butynyl; 2-methyl-3-butynyl; 1,2-dimethyl-3-butynyl; 2,2-dimethyl-3-butynyl; 1-methyl-2-pentynyl; 2-methyl-3-pentynyl; 1-methyl-4-pentynyl; 2-methyl-4-pentynyl; and 3-methyl-4-pentynyl.

By "$C_{2-6}$ heterocyclyl" is meant a stable 5- to 7-membered monocyclic or 7-to 14-membered bicyclic heterocyclic ring which is saturated partially unsaturated or unsaturated (aromatic), and which consists of 2 to 6 carbon atoms and 1, 2, 3 or 4 heteroatoms independently selected from the group consisting of N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom that results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5, 2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 1,4,5,6-tetrahydro pyridinyl, 6H-1,2,5-thiadiazinyl, 1,2, 3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, 1,4,5,6-tetrahydro pyridinyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary subsituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "$C_{7-14}$ alkaryl" is meant an alkyl substituted by an aryl group (e.g., benzyl, phenethyl, or 3,4-dichlorophenethyl) having from 7 to 14 carbon atoms.

By "$C_{3-10}$ alkheterocyclyl" is meant an alkyl substituted heterocyclic group having from 7 to 14 carbon atoms in addition to one or more heteroatoms (e.g., 3-furanylmethyl, 2-furanylmethyl, 3-tetrahydrofuranylmethyl, or 2-tetrahydrofuranylmethyl).

By "$C_{1-7}$ heteroalkyl" is meant a branched or unbranched alkyl, alkenyl, or alkynyl group having from 1 to 7 carbon atoms in addition to 1, 2, 3 or 4 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoralkyl, amino, aminoalkyl, disubstituted amino, quaternary amino, hydroxyalkyl, hydroxyalkyl, carboxyalkyl, and carboxyl groups.

By "acyl" is meant a chemical moiety with the formula R—C(O)—, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkoxy" is meant a chemical substituent of the formula —OR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "aryloxy" is meant a chemical substituent of the formula —OR, wherein R is a $C_{6-12}$ aryl group.

By "amido" is meant a chemical substituent of the formula —NRR', wherein the nitrogen atom is part of an amide bond (e.g., —C(O)—NRR') and wherein R and R' are each, independently, selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl, or —NRR' forms a $C_{2-6}$ heterocyclyl ring, as defined above, but containing at least one nitrogen atom, such as piperidino, morpholino, and azabicyclo, among others.

By "halide" is meant bromine, chlorine, iodine, or fluorine.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula —(R)—COOH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "hydroxyalkyl" is meant a chemical moiety with the formula —(R)—OH, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "alkylthio" is meant a chemical substituent of the formula —SR, wherein R is selected from $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, or $C_{1-7}$ heteroalkyl.

By "arylthio" is meant a chemical substituent of the formula —SR, wherein R is a $C_{6-12}$ aryl group.

By "quaternary amino" is meant a chemical substituent of the formula —(R)—N(R')(R'')(R''')$^+$, wherein R, R', R'', and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

The term "pharmaceutically acceptable salt" represents those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, isethionate, lactobionate, lactate, laurate, lauryl sulfate, malate, maleate, malonate, mesylate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds useful in the invention include those described herein in any of their pharmaceutically acceptable forms, including isomers such as diastereomers and enantiomers, salts, esters, amides, thioesters, solvates, and polymorphs thereof, as well as racemic mixtures and pure isomers of the compounds described herein. As an example, by "fexofenadine" is meant the free base, as well as any pharmaceutically acceptable salt thereof (e.g., fexofenadine hydrochloride).

Other features and advantages of the invention will be apparent from the following detailed description, and from the claims.

DETAILED DESCRIPTION

The invention provides therapies useful for the treatment of immunoinflammatory disorders. According to the invention, any of the foregoing conditions may be treated by administration of an effective amount of a tetra-substituted pyrimidopyrimidine or analog thereof, either alone or in combination with one or more companion compounds, including an antihistamine, a corticosteroid, rolipram, ibudilast, a tricyclic or tetracyclic antidepressant, an SSRI, a non-steroidal anti-inflammatory drug, a non-steroidal immunophilin-dependent immunosuppressant, and an analog thereof.

In one embodiment of the invention, treatment of an immunoinflammatory disorder (e.g., an inflammatory dermatosis, proliferative skin disease, organ transplant rejection, or graft versus host disease) is performed by administering a tetra-substituted pyrimidopyrimidine (or an analog thereof) and an antihistamine to a patient in need of such treatment.

In another embodiment of the invention, treatment of an immunoinflammatory disorder is performed by administering a tetra-substituted pyrimidopyrimidine (or an analog thereof) and a tricyclic or tetracyclic antidepressant to a patient in need of such treatment.

In yet another embodiment of the invention, treatment is performed by administering a tetra-substituted pyrimidopyrimidine (or an analog thereof) and a selective serotonin reuptake inhibitor to a patient suffering from any of the foregoing conditions.

In still other embodiments, treatment is performed by administering to a patient in need of such treatment, in conjunction with a tetra-substituted pyrimidopyrimidine or a tetra-substituted pyrimidopyrimidine analog, a corticosteroid, or ibudilast, or rolipram, or an analog of any of these compounds.

Routes of administration for the various embodiments include, but are not limited to, topical, transdermal, and systemic administration (such as, intravenous, intramuscular, subcutaneous, inhalation, rectal, buccal, vaginal, intraperitoneal, intraarticular, ophthalmic or oral administration). As used herein, "systemic administration" refers to all nondermal routes of administration, and specifically excludes topical and transdermal routes of administration.

Any of the foregoing therapies may be administered with conventional pharmaceuticals useful for the treatment of immunoinflammatory disorders.

Tetra-Substituted Pyrimidopyrimidines

We have discovered that certain tetra-substituted pyrimidopyrimidines are effective in treating immunoinflammatory diseases, particularly those mediated by TNFα, IL-1, or IFN-γ.

Tetra-substituted pyrimidopyrimidines have the formula (V):

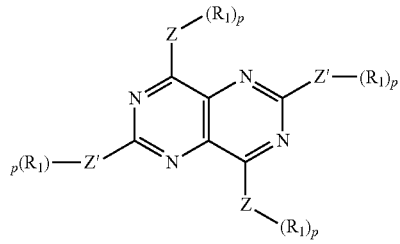

wherein each Z and each Z' is, independently, N, O, C,

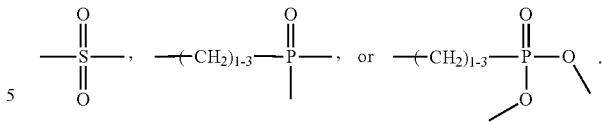

When Z or Z' is O or

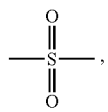

then p=1, when Z or Z' is N,

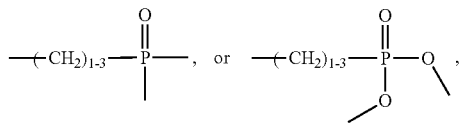

then p=2, and when Z or Z' is C, then p=3. In formula (V), each $R_1$ is, independently, X, OH, N-alkyl (wherein the alkyl group has 1 to 20, more preferably 1-5, carbon atoms); a branched or unbranched alkyl group having 1 to 20, more preferably 1-5, carbon atoms; or a heterocycle, preferably as defined in formula (Y), below. Alternatively, when p>1, two $R_1$ groups from a common Z or Z' atom, in combination with each other, may represent —$(CY_2)_k$— in which k is an integer between 4 and 6, inclusive. Each X is, independently, Y, $CY_3$, $C(CY_3)_3$, $CY_2CY_3$, $(CY_2)_{1-5}OY$, substituted or unsubstituted cycloalkane of the structure $C_nY_{2n-1}$, wherein n=3-7, inclusive. Each Y is, independently, H, F, Cl, Br, or I. In one embodiment, each Z is the same moiety, each Z' is the same moiety, and Z and Z' are different moieties.

Tetra-substituted pyrimidopyrimidines that are useful in the methods, compositions, and kits of this invention include 2,6-disubstituted 4,8-dibenzylaminopyrimido[5,4-d]pyrimidines. Particularly useful tetra-substituted pyrimidopyrimidines include dipyridamole (also known as 2,6-bis(diethanolamino)-4,8-dipiperidinopyrimido(5,4-d)pyrimidine); mopidamole; dipyridamole monoacetate; NU3026 (2,6-di-(2,2-dimethyl-1,3-dioxolan-4-yl)-methoxy-4,8-di-piperidinopyrimidopyrimidine); NU3059 (2,6-bis-(2,3-dimethyoxypropoxy)-4,8-di-piperidinopyrimidopyrimidine); NU3060 (2,6-bis[N,N-di(2-methoxy)ethyl]-4,6-di-piperidinopyrimidopyrimidine); and NU3076 (2,6-bis(diethanolamino)-4,8-di-4-methoxybenzylaminopyrimidopyrimidine). Other tetra-substituted pyrimidopyrimidines are described in U.S. Pat. Nos. 3,031,450 and 4,963,541.

The standard recommended dosage for dipyridamole is 300-400 mg/day.

In one aspect, the invention relates to a method for inhibiting proinflammatory cytokine activity in a patient suffering from or at risk of suffering from a disorder associated with cytokine activity, comprising administering to the patient a unit dose of a tetra-substituted pyrimidopyrimidine in an amount effective to inhibit or decrease the cytokine activity in the patient, said cytokine selected from TNFα, IL-1, IL-2, IL-6, IL-12, IL-15, or IFN-γ, and wherein when the tetra-substituted pyrimidopyrimidine is dipyridamole, the unit dose is suitable for systemic administration.

Antihistamines

Antihistamines are compounds that block the action of histamine. Classes of antihistamines include:

(1) Ethanolamines (e.g., bromodiphenhydramine, carbinoxamine, clemastine, dimenhydrinate, diphenhydramine, diphenylpyraline, and doxylamine);

(2) Ethylenediamines (e.g., pheniramine, pyrilamine, tripelennamine, and triprolidine);

(3) Phenothiazines (e.g., diethazine, ethopropazine, methdilazine, promethazine, thiethylperazine, and trimeprazine);

(4) Alkylamines (e.g., acrivastine, brompheniramine, chlorpheniramine, desbrompheniramine, dexchlorpheniramine, pyrrobutamine, and triprolidine);

(5) Piperazines (e.g., buclizine, cetirizine, chlorcyclizine, cyclizine, meclizine, hydroxyzine);

(6) Piperidines (e.g., astemizole, azatadine, cyproheptadine, desloratadine, fexofenadine, loratadine, ketotifen, olopatadine, phenindamine, and terfenadine);

(7) Atypical antihistamines (e.g., azelastine, levocabastine, methapyrilene, and phenyltoxamine).

In the methods, compositions, and kits of the invention, both non-sedating and sedating antihistamines may be employed. Particularly desirable antihistamines for use in the methods, compositions, and kits of the invention are non-sedating antihistamines such as loratadine and desloratadine. Sedating antihistamines can also be used in the methods, compositions, and kits of the invention. Preferred sedating antihistamines are methods, compositions, and kits of the invention are azatadine, bromodiphenhydramine; chlorpheniramine; clemizole; cyproheptadine; dimenhydrinate; diphenhydramine; doxylamine; meclizine; promethazine; pyrilamine; thiethylperazine; and tripelennamine.

Other antihistamines suitable for use in the methods and compositions of the invention are acrivastine; ahistan; antazoline; astemizole; azelastine (e.g., azelsatine hydrochloride); bamipine; bepotastine; bietanautine; brompheniramine (e.g., brompheniramine maleate); carbinoxamine (e.g., carbinoxamine maleate); cetirizine (e.g., cetirizine hydrochloride); cetoxime; chlorocyclizine; chloropyramine; chlorothen; chlorphenoxamine; cinnarizine; clemastine (e.g., clemastine fumarate); clobenzepam; clobenztropine; clocinizine; cyclizine (e.g., cyclizine hydrochloride; cyclizine lactate); deptropine; dexchlorpheniramine; dexchlorpheniramine maleate; diphenylpyraline; doxepin; ebastine; embramine; emedastine (e.g., emedastine difumarate); epinastine; etymemazine hydrochloride; fexofenadine (e.g., fexofenadine hydrochloride); histapyrrodine; hydroxyzine (e.g., hydroxyzine hydrochloride; hydroxyzine pamoate); isopromethazine; isothipendyl; levocabastine (e.g., levocabastine hydrochloride); mebhydroline; mequitazine; methafurylene; methapyrilene; metron; mizolastine; olapatadine (e.g., olopatadine hydrochloride); orphenadrine; phenindamine (e.g., phenindamine tartrate); pheniramine; phenyltoloxamine; p-methyldiphenhydramine; pyrrobutamine; setastine; talastine; terfenadine; thenyldiamine; thiazinamium (e.g., thiazinamium methylsulfate); thonzylamine hydrochloride; tolpropamine; triprolidine; and tritoqualine.

Structural analogs of antihistamines may also be used in according to the invention. Antihistamine analogs include, without limitation, 10-piperazinylpropylphenothiazine; 4-(3-(2-chlorophenothiazin-10-yl)propyl)-1-piperazineethanol dihydrochloride; 1-(10-(3-(4-methyl-1-piperazinyl)propyl)-10H-phenothiazin-2-yl)-(9CI) 1-propanone; 3-methoxycyproheptadine; 4-(3-(2-Chloro-10H-phenothiazin-10-yl) propyl)piperazine-1-ethanol hydrochloride; 10,11-dihydro-5-(3-(4-ethoxycarbonyl-4-phenylpiperidino)propylidene)-5H-dibenzo(a,d)cycloheptene; aceprometazine; acetophenazine; alimemazin (e.g., alimemazin hydrochloride); aminopromazine; benzimidazole; butaperazine; carfenazine; chlorfenethazine; chlormidazole; cinprazole; desmethylastemizole; desmethylcyproheptadine; diethazine (e.g., diethazine hydrochloride); ethopropazine (e.g., ethopropazine hydrochloride); 2-(p-bromophenyl-(p'-tolyl)methoxy)-N,N-dimethyl-ethylamine hydrochloride; N,N-dimethyl-2-(diphenylmethoxy)-ethylamine methylbromide; EX-10-542A; fenethazine; fuprazole; methyl 10-(3-(4-methyl-1-piperazinyl)propyl)phenothiazin-2-yl ketone; lerisetron; medrylamine; mesoridazine; methylpromazine; N-desmethylpromethazine; nilprazole; northioridazine; perphenazine (e.g., perphenazine enanthate); 10-(3-dimethylaminopropyl)-2-methylthio-phenothiazine; 4-(dibenzo(b,e)thiepin-6(11H)-ylidene)-1-methyl-piperidine hydrochloride; prochlorperazine; promazine; propiomazine (e.g., propiomazine hydrochloride); rotoxamine; rupatadine; Sch 37370; Sch 434; tecastemizole; thiazinamium; thiopropazate; thioridazine (e.g., thioridazine hydrochloride); and 3-(10,11-dihydro-5H-dibenzo(a,d)cyclohepten-5-ylidene)-tropane.

Other compounds that are suitable for use in the invention are AD-0261; AHR-5333; alinastine; arpromidine; ATI-19000; bermastine; bilastin; Bron-12; carebastine; chlorphenamine; clofurenadine; corsym; DF-1105501; DF-11062; DF-1111301; EL-301; elbanizine; F-7946T; F-9505; HE-90481; HE-90512; hivenyl; HSR-609; icotidine; KAA-276; KY-234; lamiakast; LAS-36509; LAS-36674; levocetirizine; levoprotiline; metoclopramide; NIP-531; noberastine; oxatomide; PR-881-884A; quisultazine; rocastine; selenotifen; SK&F-94461; SODAS-HC; tagorizine; TAK-427; temelastine; UCB-34742; UCB-35440; VUF-K-8707; Wy-49051; and ZCR-2060.

Still other compounds that are suitable for use in the invention are described in U.S. Pat. Nos. 3,956,296; 4,254,129; 4,254,130; 4,282,833; 4,283,408; 4,362,736; 4,394,508; 4,285,957; 4,285,958; 4,440,933; 4,510,309; 4,550,116; 4,692,456; 4,742,175; 4,833,138; 4,908,372; 5,204,249; 5,375,693; 5,578,610; 5,581,011; 5,589,487; 5,663,412; 5,994,549; 6,201,124; and 6,458,958.

Standard Recommended Dosages

Standard recommended dosages for several exemplary antihistamines are shown in Table 1. Other standard dosages are provided, e.g., in the Merck Manual of Diagnosis & Therapy (17th Ed. M H Beers et al., Merck & Co.) and Physicians' Desk Reference 2003 (57th Ed. Medical Economics Staff et al., Medical Economics Co., 2002).

TABLE 1

| Compound | Standard Dose |
| --- | --- |
| Desloratadine | 5 mg/once daily |
| Thiethylperazine | 10 mg/1-3 times daily |
| Bromodiphenhydramine | 12.5-25 mg/every 4-6 hours |
| Promethazine | 25 mg/twice daily |
| Cyproheptadine | 12-16 mg/day |
| Loratadine | 10 mg/once daily |
| Clemizole | 100 mg given as IV or IM |
| Azatadine | 1-2 mg/twice daily |
| Cetirizine | 5-10 mg/once daily |
| Chlorpheniramine | 2 mg/every 6 hours or 4 mg/every 6 hours |
| Dimenhydramine | 50-100 mg/every 4-6 hours |
| Diphenhydramine | 25 mg/every 4-6 hours or 38 mg/every 4-6 hours* |
| Doxylamine | 25 mg/once daily or 12.5 mg/every four hours* |
| Fexofenadine | 60 mg/twice daily or 180 mg/once daily |
| Meclizine | 25-100 mg/day |

TABLE 1-continued

| Compound | Standard Dose |
| --- | --- |
| Pyrilamine | 30 mg/every 6 hours |
| Tripelennamine | 25-50 mg/every 4 to 6 hours or 100 mg/twice daily (extended release) |

Loratadine

Loratadine (CLARITIN) is a tricyclic piperidine that acts as a selective peripheral histamine H1-receptor antagonist. We report herein that loratadine and structural and functional analogs thereof, such as piperidines, tricyclic piperidines, histamine H1-receptor antagonists, are useful in the anti-immunoinflammatory combination of the invention for the treatment of immunoinflammatory disorders, transplanted organ rejection, and graft versus host disease.

Loratadine functional and/or structural analogs include other H1-receptor antagonists, such as AHR-11325, acrivastine, antazoline, astemizole, azatadine, azelastine, bromopheniramine, carebastine, cetirizine, chlorpheniramine, chlorcyclizine, clemastine, cyproheptadine, descarboethoxyloratadine, dexchlorpheniramine, dimenhydrinate, diphenylpyraline, diphenhydramine, ebastine, fexofenadine, hydroxyzine ketotifen, lodoxamide, levocabastine, methdilazine, mequitazine, oxatomide, pheniramine pyrilamine, promethazine, pyrilamine, setastine, tazifylline, temelastine, terfenadine, trimeprazine, tripelennamine, triprolidine, utrizine, and similar compounds (described, e.g., in U.S. Pat. Nos. 3,956,296, 4,254,129, 4,254,130, 4,283,408, 4,362,736, 4,394,508, 4,285,957, 4,285,958, 4,440,933, 4,510,309, 4,550,116, 4,692,456, 4,742,175, 4,908,372, 5,204,249, 5,375,693, 5,578,610, 5,581,011, 5,589,487, 5,663,412, 5,994,549, 6,201,124, and 6,458,958).

Loratadine, cetirizine, and fexofenadine are second-generation H1-receptor antagonists that lack the sedating effects of many first generation H1-receptor antagonists. Piperidine H1-receptor antagonists include loratadine, cyproheptadine hydrochloride (PERIACTIN), and phenindiamine tartrate (NOLAHIST). Piperazine H1-receptor antagonists include hydroxyzine hydrochloride (ATARAX), hydroxyzine pamoate (VISTARIL), cyclizine hydrochloride (MAREZINE), cyclizine lactate, and meclizine hydrochloride.

Loratadine Standard Recommended Dosages

Loratadine oral formulations include tablets, redi-tabs, and syrup. Loratadine tablets contain 10 mg micronized loratadine. Loratadine syrup contains 1 mg/ml micronized loratadine, and reditabs (rapidly-disintegrating tablets) contain 10 mg micronized loratadine in tablets that disintegrate quickly in the mouth. While suggested dosages will vary with a patient's condition, standard recommended dosages are provided below. Loratadine is typically administered once daily in a 10 mg dose, although other daily dosages useful in the anti-immunoinflammatory combination of the invention include 0.01-0.05 mg, 0.05-1 mg, 1-3 mg, 3-5 mg, 5-10 mg, 10-15 mg, 15-20 mg, 20-30 mg, and 30-40 mg.

Loratadine is rapidly absorbed following oral administration. It is metabolized in the liver to descarboethoxyloratadine by cytochrome P450 3A4 and cytochrome P450 2D6. Loratadine metabolites are also useful in the anti-immunoinflammatory combination of the invention.

Corticosteroids

If desired, one or more corticosteroid may be administered in a method of the invention or may be formulated with a tetra-substituted pyrimidopyrimidine or analog thereof in a composition of the invention. Our data show that dipyridamole in combination with various corticosteroids is more effective in suppressing TNFα in vitro than either agent alone. Accordingly, this combination may be more effective in treating immunoinflammatory diseases, particularly those mediated by TNFα levels, than either the tetra-substituted pyrimidopyrimidine or corticosteroid alone. Suitable corticosteroids include 11-alpha,17-alpha,21-trihydroxypregn-4-ene-3,20-dione; 11-beta,16-alpha,17,21-tetrahydroxypregn-4-ene-3,20-dione; 11-beta,16-alpha,17,21-tetrahydroxypregn-1,4-diene-3,20-dione; 11-beta,17-alpha,21-trihydroxy-6-alpha-methylpregn-4-ene-3,20-dione; 11-dehydrocorticosterone; 11-deoxycortisol; 11-hydroxy-1,4-androstadiene-3,17-dione; 11-ketotestosterone; 14-hydroxyandrost-4-ene-3,6,17-trione; 15,17-dihydroxyprogesterone; 16-methylhydrocortisone; 17,21-dihydroxy-16-alpha-methylpregna-1,4,9(11)-triene-3,20-dione; 17-alpha-hydroxypregn-4-ene-3,20-dione; 17-alpha-hydroxypregnenolone; 17-hydroxy-16-beta-methyl-5-beta-pregn-9(11)-ene-3,20-dione; 17-hydroxy-4,6,8(14)-pregnatriene-3,20-dione; 17-hydroxypregna-4,9(11)-diene-3,20-dione; 18-hydroxycorticosterone; 18-hydroxycortisone; 18-oxocortisol; 21-deoxyaldosterone; 21-deoxycortisone; 2-deoxyecdysone; 2-methylcortisone; 3-dehydroecdysone; 4-pregnene-17-alpha,20-beta, 21-triol-3,11-dione; 6,17,20-trihydroxypregn-4-ene-3-one; 6-alpha-hydroxycortisol; 6-alpha-fluoroprednisolone, 6-alpha-methylprednisolone, 6-alpha-methylprednisolone 21-acetate, 6-alpha-methylprednisolone 21-hemisuccinate sodium salt, 6-beta-hydroxycortisol, 6-alpha, 9-alpha-difluoroprednisolone 21-acetate 17-butyrate, 6-hydroxycorticosterone; 6-hydroxydexamethasone; 6-hydroxyprednisolone; 9-fluorocortisone; alclometasone dipropionate; aldosterone; algestone; alphaderm; amadinone; amcinonide; anagestone; androstenedione; anecortave acetate; beclomethasone; beclomethasone dipropionate; beclomethasone dipropionate monohydrate; betamethasone 17-valerate; betamethasone sodium acetate; betamethasone sodium phosphate; betamethasone valerate; bolasterone; budesonide; calusterone; chlormadinone; chloroprednisone; chloroprednisone acetate; cholesterol; clobetasol; clobetasol propionate; clobetasone; clocortolone; clocortolone pivalate; clogestone; cloprednol; corticosterone; cortisol; cortisol acetate; cortisol butyrate; cortisol cypionate; cortisol octanoate; cortisol sodium phosphate; cortisol sodium succinate; cortisol valerate; cortisone; cortisone acetate; cortodoxone; daturaolone; deflazacort, 21-deoxycortisol, dehydroepiandrosterone; delmadinone; deoxycorticosterone; deprodone; descinolone; desonide; desoximethasone; dexafen; dexamethasone; dexamethasone 21-acetate; dexamethasone acetate; dexamethasone sodium phosphate; dichlorisone; diflorasone; diflorasone diacetate; diflucortolone; dihydroelatericin a; domoprednate; doxibetasol; ecdysone; ecdysterone; endrysone; enoxolone; flucinolone; fludrocortisone; fludrocortisone acetate; flugestone; flumethasone; flumethasone pivalate; flumoxonide; flunisolide; fluocinolone; fluocinolone acetonide; fluocinonide; 9-fluorocortisone; fluocortolone; fluorohydroxyandrostenedione; fluorometholone; fluorometholone acetate; fluoxymesterone; fluprednidene; fluprednisolone; flurandrenolide; fluticasone; fluticasone propionate; formebolone; formestane; formocortal; gestonorone; glyderinine; halcinonide; hyrcanoside; halometasone; halopredone; haloprogesterone; hydrocortiosone cypionate; hydrocortisone; hydrocortisone 21-butyrate; hydrocortisone aceponate; hydrocortisone acetate; hydrocortisone buteprate; hydrocortisone butyrate; hydrocortisone cypionate; hydrocortisone hemisuccinate; hydrocortisone probutate; hydrocortisone sodium phosphate; hydrocortisone sodium succinate; hydrocortisone valerate; hydroxyprogesterone; inokosterone; isoflupredone; isoflupredone acetate; isoprednidene; meclorisone; mecortolon; medrogestone; medroxyprogesterone; medrysone; megestrol; megestrol acetate; melengestrol; meprednisone; methandrostenolone; methylprednisolone; methylprednisolone aceponate; methylprednisolone acetate; methylprednisolone hemisuccinate; methylprednisolone sodium succinate; methyltestosterone; metribolone; mometasone; mometasone furoate; mometasone furoate monohydrate; nisone; nomegestrol; norgestomet; norvinisterone; oxymesterone; paramethasone; paramethasone acetate; ponasterone; prednisolamate; prednisolone; prednisolone 21-hemisuccinate; prednisolone acetate; prednisolone farnesylate; prednisolone hemisuccinate; prednisolone-21(beta-D-glucuronide); prednisolone metasulphobenzoate; prednisolone sodium phosphate; prednisolone steaglate; prednisolone tebutate; prednisolone tetrahydrophthalate; prednisone; prednival; prednylidene; pregnenolone; procinonide; tralonide; progesterone; promegestone; rhapontisterone; rimexolone; roxibolone; rubrosterone; stizophyllin; tixocortol; topterone; triamcinolone; triamcinolone acetonide; triamcinolone acetonide 21-palmitate; triamcinolone diacetate; triamcinolone hexacetonide; trimegestone; turkesterone; and wortmannin.

Standard recommended dosages for various steroid/disease combinations are provided in Table 2, below.

TABLE 2

Standard Recommended Corticosteroid Dosages

| Indication | Route | Drug | Dose | Schedule |
| --- | --- | --- | --- | --- |
| Psoriasis | oral | prednisolone | 7.5-60 mg | per day or divided b.i.d. |
|  | oral | prednisone | 7.5-60 mg | per day or divided b.i.d. |
| Asthma | inhaled | beclomethasone dipropionate | 42 µg/puff) | 4-8 puffs b.i.d. |
|  | inhaled | budesonide | (200 µg/inhalation) | 1-2 inhalations b.i.d. |
|  | inhaled | flunisolide | (250 µg/puff) | 2-4 puffs b.i.d. |
|  | inhaled | fluticasone propionate | (44, 110 or 220 µg/puff) | 2-4 puffs b.i.d. |
|  | inhaled | triamcinolone acetonide | (100 µg/puff) | 2-4 puffs b.i.d. |
| COPD | oral | prednisone | 30-40 mg | per day |
| Crohn's disease | oral | budesonide | 9 mg | per day |
| Ulcerative colitis | oral | prednisone | 40-60 mg | per day |
|  | oral | hydrocortisone | 300 mg (IV) | per day |
|  | oral | methylprednisolone | 40-60 mg | per day |
| Rheumatoid arthritis | oral | prednisone | 10 mg | per day |

Other standard recommended dosages for corticosteroids are provided, e.g., in the Merck Manual of Diagnosis & Therapy (17th Ed. M H Beers et al., Merck & Co.) and Physicians' Desk Reference 2003 (57$^{th}$ Ed. Medical Economics Staff et al., Medical Economics Co., 2002). In one embodiment, the dosage of corticosteroid administered is a dosage equivalent to a prednisolone dosage, as defined herein. For example, a low dosage of a corticosteroid may be considered as the dosage equivalent to a low dosage of prednisolone.

Steroid Receptor Modulators

Steroid receptor modulators (e.g., antagonists and agonists) may be used as a substitute for or in addition to a corticosteroid in the methods, compositions, and kits of the invention. Thus, in one embodiment, the invention features the combination of a tetra-substituted pyrimidopyridine and a glucocorticoid receptor modulator or other steroid receptor modulator, and methods of treating immunoinflammatory disorders therewith.

Glucocorticoid receptor modulators that may used in the methods, compositions, and kits of the invention include compounds described in U.S. Pat. Nos. 6,380,207, 6,380,223, 6,448,405, 6,506,766, and 6,570,020, U.S. Patent Application Publication Nos. 2003/0176478, 2003/0171585, 2003/0120081, 2003/0073703, 2002/015631, 2002/0147336, 2002/0107235, 2002/0103217, and 2001/0041802, and PCT Publication No. WO00/66522, each of which is hereby incorporated by reference. Other steroid receptor modulators may also be used in the methods, compositions, and kits of the invention are described in U.S. Pat. Nos. 6,093,821, 6,121,450, 5,994,544, 5,696,133, 5,696,127, 5,693,647, 5,693,646, 5,688,810, 5,688,808, and 5,696,130, each of which is hereby incorporated by reference.

Other Compounds

Other compounds that may be used as a substitute for or in addition to a corticosteroid in the methods, compositions, and kits of the invention A-348441 (Karo Bio), adrenal cortex extract (GlaxoSmithKline), alsactide (Aventis), amebucort (Schering AG), amelometasone (Taisho), ATSA (Pfizer), bitolterol (Elan), CBP-2011 (InKine Pharmaceutical), cebaracetam (Novartis) CGP-13774 (Kissei), ciclesonide (Altana), ciclometasone (Aventis), clobetasone butyrate (GlaxoSmithKline), cloprednol (Hoffmann-La Roche), collismycin A (Kirin), cucurbitacin E (NIH), deflazacort (Aventis), deprodone propionate (SSP), dexamethasone acefurate (Schering-Plough), dexamethasone linoleate (GlaxoSmithKline), dexamethasone valerate (Abbott), difluprednate (Pfizer), domoprednate (Hoffmann-La Roche), ebiratide (Aventis), etiprednol dicloacetate (IVAX), fluazacort (Vicuron), flumoxonide (Hoffmann-La Roche), fluocortin butyl (Schering AG), fluocortolone monohydrate (Schering AG), GR-250495X (GlaxoSmithKline), halometasone (Novartis), halopredone (Dainippon), HYC-141 (Fidia), icomethasone enbutate (Hovione), itrocinonide (AstraZeneca), L-6485 (Vicuron), Lipocort (Draxis Health), locicortone (Aventis), meclorisone (Schering-Plough), naflocort (Bristol-Myers Squibb), NCX-1015 (NicOx), NCX-1020 (NicOx), NCX-1022 (NicOx), nicocortonide (Yamanouchi), NIK-236 (Nikken Chemicals), NS-126 (SSP), Org-2766 (Akzo Nobel), Org-6632 (Akzo Nobel), P16CM, propylmesterolone (Schering AG), RGH-1113 (Gedeon Richter), rofleponide (AstraZeneca), rofleponide palmitate (AstraZeneca), RPR-106541 (Aventis), RU-26559 (Aventis), Sch-19457 (Schering-Plough), T25 (Matrix Therapeutics), TBI-PAB (Sigma-Tau), ticabesone propionate (Hoffmann-La Roche), tifluadom (Solvay), timobesone (Hoffmann-La Roche), TSC-5 (Takeda), and ZK-73634 (Schering AG).

Ibudilast

A tetra-substituted pyrimidopyrimidine or a tetra-substituted pyrimidopyrimidine analog may be administered or formulated with ibudilast or an ibudilast analog, defined by formula (VI).

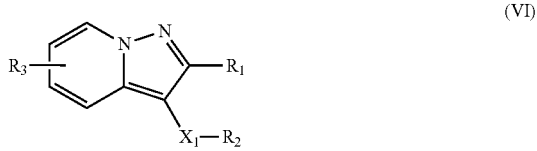

In formula (VI) $R_1$ and $R_2$ are each, independently, selected from H, $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl; $R_3$ is selected from H, halide, alkoxy, and $C_{1-4}$ alkyl; $X_1$ is selected from C=O, C=N—NH—$R_4$, C=C($R_5$)—C(O)—$R_6$, C=CH=CH—C(O)—$R_6$, and C(OH)—$R_7$; $R_4$ is selected from H and acyl; $R_5$ is selected from H, halide, and $C_{1-4}$ alkyl; $R_6$ is selected from OH, alkoxy and amido; and $R_7$ is selected from H, $C_{1-7}$ alkyl, $C_{2-7}$ alkenyl, $C_{2-7}$ alkynyl, $C_{2-6}$ heterocyclyl, $C_{6-12}$ aryl, $C_{7-14}$ alkaryl, $C_{3-10}$ alkheterocyclyl, and $C_{1-7}$ heteroalkyl. Compounds of formula (VI) include, the compounds described in U.S. Pat. Nos. 3,850,941; 4,097,483; 4,578,392; 4,925,849; 4,994,453; and 5,296,490. Commercially available compounds of formula (VI) include ibudilast and KC-764.

The standard recommended dosage for the treatment of bronchial asthma is typically 10 mg of ibudilast twice daily, while in the case of cerebrovascular disorders, the standard recoomended dosage is 10 mg of ibudilast three times daily. The structure of ibudilast is shown below:

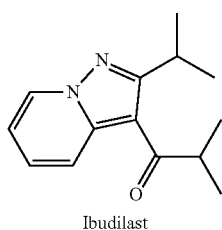

Ibudilast

KC-764 (CAS 94457-09-7) is reported to be a platelet aggregation inhibitor. The structure of KC-764 is shown below:

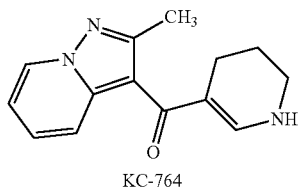

KC-764

KC-764 and other compound of formula (VI) can be prepared using the synthetic methods described in U.S. Pat. Nos. 3,850,941; 4,097,483; 4,578,392; 4,925,849; 4,994,453; and 5,296,490.

Rolipram

In one embodiment of the invention, a tetra-substituted pyrimidopyrimidine or analog thereof is administered or formulated with rolipram (4-[3-(cyclopentyloxy)-4-methoxyphenyl]-2-pyrrolidone) or an analog of rolipram. Rolipram analogs are described by formula (I) of U.S. Pat. No. 4,193,926, hereby incorporated by reference.

Tricyclic and Tetracyclic Antidepressants

In one embodiment of the invention, a tetra-substituted pyrimidopyrimidine or analog thereof is administered or formulated with a tricyclic or tetracyclic antidepressant, or an analog thereof. By "tricyclic or tetracyclic antidepressant analog" is meant a compound having one the formulas (I), (II), (III), or (IV):

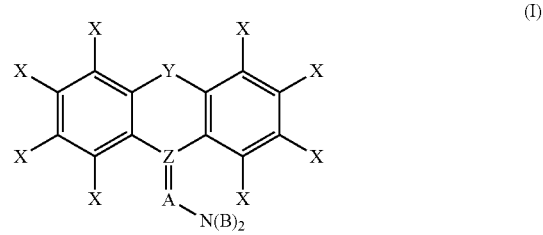

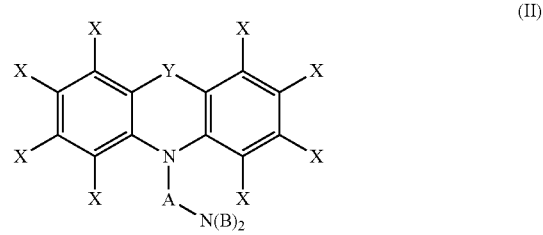

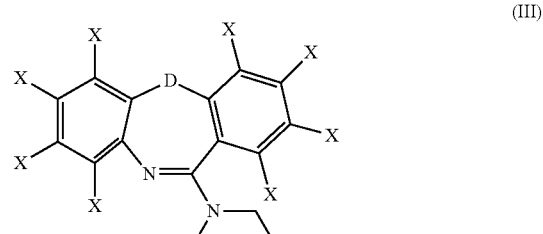

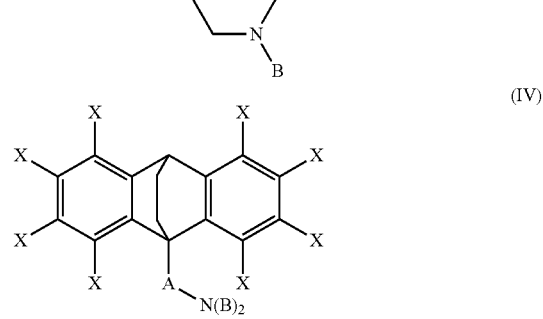

or a pharmaceutically acceptable salt, ester, amide, or derivative thereof, wherein each X is, independently, H, Cl, F, Br, I, $CH_3$, $CF_3$, OH, $OCH_3$, $CH_2CH_3$, or $OCH_2CH_3$; Y is $CH_2$, O, NH, $S(O)_{0-2}$, $(CH_2)_3$, $(CH)_2$, $CH_2O$, $CH_2NH$, CHN, or $CH_2S$; Z is C or S; A is a branched or unbranched, saturated or monounsaturated hydrocarbon chain having between 3 and 6 carbons, inclusive; each B is, independently, H, Cl, F, Br, I, $CX_3$, $CH_2CH_3$, $OCX_3$, or $OCX_2CX_3$; and D is $CH_2$, O, NH, $S(O)_{0-2}$.

In preferred embodiments, each X is, independently, H, Cl, or F; Y is $(CH_2)_2$, Z is C; A is $(CH_2)_3$; and each B is, independently, H, Cl, or F.

Tricyclic or tetracyclic antidepressants, as well as analogs thereof that are suitable for use in the methods and compositions of the invention, include 10-(4-methylpiperazin-1-yl) pyrido(4,3-b)(1,4)benzothiazepine; 11-(4-methyl-1-piperazinyl)-5H-dibenzo(b,e)(1,4)diazepine; 5,10-dihydro-7-chloro-10-(2-(morpholino)ethyl)-11H-dibenzo(b,e)(1,4) diazepin-11-one; 2-(2-(7-hydroxy-4-dibenzo(b,f)(1,4) thiazepine-11-yl-1-piperazinyl)ethoxy)ethanol; 2-chloro-11-(4-methyl-1-piperazinyl)-5H-dibenzo(b,e)(1,4) diazepine; 4-(11H-dibenz(b,e)azepin-6-yl)piperazine; 8-chloro-11-(4-methyl-1-piperazinyl)-5H-dibenzo(b,e)(1,4) diazepin-2-ol; 8-chloro-11-(4-methyl-1-piperazinyl)-5H-dibenzo(b,e)(1,4)diazepine monohydrochloride; 8-chloro-2-methoxy-11-(4-methyl-1-piperazinyl)-5H-dibenzo(b,e)(1,4) diazepine; (Z)-2-butenedioate; 7-hydroxyamoxapine; 8-hydroxyamoxapine; 8-hydroxyloxapine; Adinazolam; Amineptine; amitriptyline; amitriptylinoxide; amoxapine; butriptyline; clomipramine; clothiapine; clozapine; demexiptiline; desipramine; 11-(4-methyl-1-piperazinyl)-dibenz(b,f) (1,4)oxazepine; 11-(4-methyl-1-piperazinyl)-2-nitro-dibenz (b,f)(1,4)oxazepine; 2-chloro-11-(4-methyl-1-piperazinyl)-dibenz(b,f) (1,4)oxazepine monohydrochloride; 11-(4-methyl-1-piperazinyl)-dibenzo(b,f)(1,4)thiazepine; dibenzepin; dimetacrine; dothiepin; doxepin; fluacizine; fluperlapine; imipramine; imipramine N-oxide; iprindole lofepramine; loxapine; loxapine hydrochloride; loxapine succinate; maprotiline; melitracen; metapramine; metiapine; metralindole; mianserin; mirtazapine; 8-chloro-6-(4-methyl-1-piperazinyl)-morphanthridine; N-acetylamoxapine; nomifensine; norclomipramine; norclozapine; nortriptyline; noxiptilin; octriptyline; opipramol; oxaprotiline; perlapine; pizotyline; propizepine; protriptyline; quetiapine; quinupramine; tianeptine; tomoxetine; and trimipramine. Others are described in U.S. Pat. Nos. 4,933,438 and 4,931,435.

Standard recommended dosages for several tricyclic antidepressants are provided in Table 3, below. Other standard dosages are provided, e.g., in the Merck Manual of Diagnosis & Therapy (17th Ed. M H Beers et al., Merck & Co.) and Physicians' Desk Reference 2003 (57th Ed. Medical Economics Staff et al., Medical Economics Co., 2002).

TABLE 3

| Compound | Standard Dose |
| --- | --- |
| Amoxapine | 200-300 mg/day |
| Nortriptyline | 75-150 mg/day |
| Desipramine | 100-200 mg/day |

Selective Serotonin Reuptake Inhibitors

In one embodiment of the invention, a tetra-substituted pyrimidopyrimidine or analog thereof is administered or formulated with an SSRI or an analog thereof. Suitable SSRIs include cericlamine (e.g., cericlamine hydrochloride); citalopram (e.g., citalopram hydrobromide); clovoxamine; cyanodothiepin; dapoxetine; escitalopram (escitalopram oxalate); femoxetine (e.g., femoxetine hydrochloride); fluoxetine (e.g., fluoxetine hydrochloride); fluvoxamine (e.g., fluvoxamine maleate); ifoxetine; indalpine (e.g., indalpine hydrochloride); indeloxazine (e.g., indeloxazine hydrochloride); litoxetine; milnacipran (e.g., minlacipran hydrochloride); paroxetine (e.g., paroxetine hydrochloride hemihydrate; paroxetine maleate; paroxetine mesylate); sertraline (e.g., sertraline hydrochloride); tametraline hydrochloride; viqualine; and zimeldine (e.g., zimeldine hydrochloride).

Cericlamine

Cericlamine has the following structure:

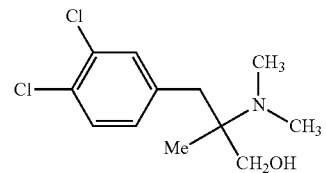

Structural analogs of cericlamine are those having the formula:

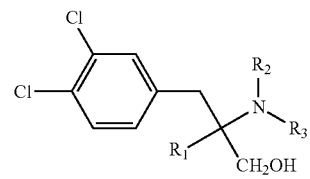

as well as pharmaceutically acceptable salts thereof, wherein $R_1$ is a $C_1$-$C_4$ alkyl and $R_2$ is H or $C_{1-4}$ alkyl, $R_3$ is H, $C_{1-4}$ alkyl, $C_{2-4}$ alkenyl, phenylalkyl or cycloalkylalkyl with 3 to 6 cyclic carbon atoms, alkanoyl, phenylalkanoyl or cycloalkylcarbonyl having 3 to 6 cyclic carbon atoms, or $R_2$ and $R_3$ form, together with the nitrogen atom to which they are linked, a heterocycle saturated with 5 to 7 chain links which can have, as the second heteroatom not directly connected to the nitrogen atom, an oxygen, a sulphur or a nitrogen, the latter nitrogen heteroatom possibly carrying a $C_{2-4}$ alkyl.

Exemplary cericlamine structural analogs are 2-methyl-2-amino-3-(3,4-dichlorophenyl)-propanol, 2-pentyl-2-amino-3-(3,4-dichlorophenyl)-propanol, 2-methyl-2-methylamino-3-(3,4-dichlorophenyl)-propanol, 2-methyl-2-dimethylamino-3-(3,4-dichlorophenyl)-propanol, and pharmaceutically acceptable salts of any thereof.

Citalopram

Citalopram has the following structure:

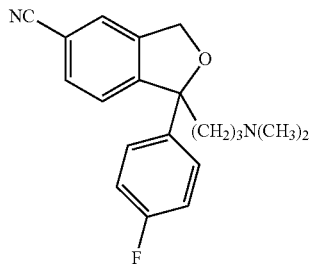

Structural analogs of citalopram are those having the formula:

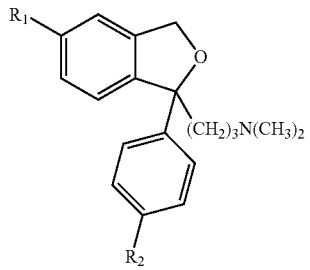

as well as pharmaceutically acceptable salts thereof, wherein each of $R_1$ and $R_2$ is independently selected from the group consisting of bromo, chloro, fluoro, trifluoromethyl, cyano and R—CO—, wherein R is $C_{1-4}$ alkyl.

Exemplary citalopram structural analogs (which are thus SSRI structural analogs according to the invention) are 1-(4'-fluorophenyl)-1-(3-dimethylaminopropyl)-5-bromophthalane; 1-(4'-chlorophenyl)-1-(3-dimethylaminopropyl)-5-chlorophthalane; 1-(4'-bromophenyl)-1-(3-dimethylaminopropyl)-5-chlorophthalane; 1-(4'-fluorophenyl)-1-(3-dimethylaminopropyl)-5-chlorophthalane; 1-(4'-chlorophenyl)-1-(3-dimethylaminopropyl)-5-trifluoromethyl-phthalane; 1-(4'-bromophenyl)-1-(3-dimethylaminopropyl)-5-trifluoromethyl-phthalane; 1-(4'-fluorophenyl)-1-(3-dimethylaminopropyl)-5-trifluoromethyl-phthalane; 1-(4'-fluorophenyl)-1-(3-dimethylaminopropyl)-5-fluorophthalane; 1-(4'-chlorophenyl)-1-(3-dimethylaminopropyl)-5-fluorophthalane; 1-(4'-chlorophenyl)-1-(3-dimethylaminopropyl)-5-phthalancarbonitrile; 1-(4'-fluorophenyl)-1-(3-dimethylaminopropyl)-5-phthalancarbonitrile; 1-(4'-cyanophenyl)-1-(3-dimethylaminopropyl)-5-phthalancarbonitrile; 1-(4'-cyanophenyl)-1-(3-dimethylaminopropyl)-5-chlorophthalane; 1-(4'-cyanophenyl)-1-(3-dimethylaminopropyl)-5-trifluoromethylphthalane; 1-(4'-fluorophenyl)-1-(3-dimethylaminopropyl)-5-phthalancarbonitrile; 1-(4'-chlorophenyl)-1-(3-dimethylaminopropyl)-5-ionylphthalane; 1-(4-(chlorophenyl)-1-(3-dimethylaminopropyl)-5-propionylphthalane; and pharmaceutically acceptable salts of any thereof.

Clovoxamine

Clovoxamine has the following structure:

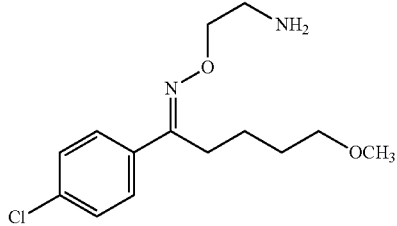

Structural analogs of clovoxamine are those having the formula:

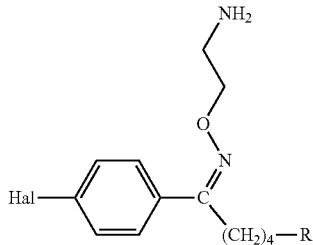

as well as pharmaceutically acceptable salts thereof, wherein Hal is a chloro, bromo, or fluoro group and R is a cyano, methoxy, ethoxy, methoxymethyl, ethoxymethyl, methoxyethoxy, or cyanomethyl group.

Exemplary clovoxamine structural analogs are 4'-chloro-5-ethoxyvalerophenone O-(2-aminoethyl)oxime; 4'-chloro-5-(2-methoxyethoxy)valerophenone O-(2-aminoethyl)oxime; 4'-chloro-6-methoxycaprophenone O-(2-aminoethyl)oxime; 4'-chloro-6-ethoxycaprophenone O-(2-aminoethyl)oxime; 4'-bromo-5-(2-methoxyethoxy)valerophenone O-(2-aminoethyl)oxime; 4'-bromo-5-methoxyvalerophenone O-(2-aminoethyl)oxime; 4'-chloro-6-cyanocaprophenone O-(2-aminoethyl)oxime; 4'-chloro-5-cyanovalerophenone O-(2-aminoethyl)oxime; 4'-bromo-5-cyanovalerophenone O-(2-aminoethyl)oxime; and pharmaceutically acceptable salts of any thereof.

Femoxetine

Femoxetine has the following structure:

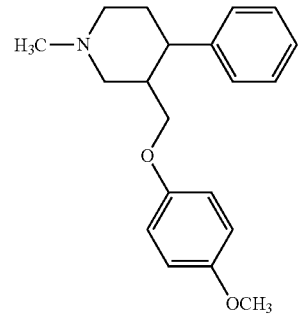

Structural analogs of femoxetine are those having the formula:

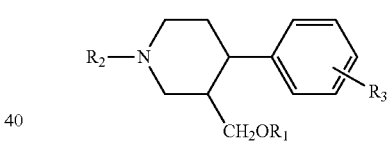

wherein $R_1$ represents a $C_{1-4}$ alkyl or $C_{2-4}$ alkynyl group, or a phenyl group optionally substituted by $C_{1-4}$ alkyl, $C_{1-4}$ alkylthio, $C_{1-4}$ alkoxy, bromo, chloro, fluoro, nitro, acylamino, methylsulfonyl, methylenedioxy, or tetrahydronaphthyl, $R_2$ represents a $C_{1-4}$ alkyl or $C_{2-4}$ alkynyl group, and $R_3$ represents hydrogen, $C_{1-4}$ alkyl, $C_{1-4}$alkoxy, trifluoroalkyl, hydroxy, bromo, chloro, fluoro, methylthio, or aralkyloxy.

Exemplary femoxetine structural analogs are disclosed in Examples 7-67 of U.S. Pat. No. 3,912,743, hereby incorporated by reference.

Fluoxetine

Fluoxetine has the following structure:

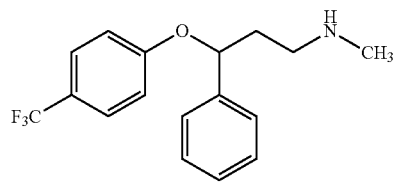

Structural analogs of fluoxetine are those compounds having the formula:

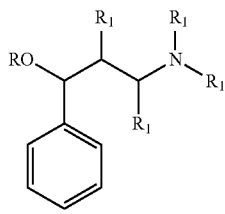

as well as pharmaceutically acceptable salts thereof, wherein each $R_1$ is independently hydrogen or methyl; R is naphthyl or

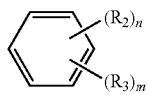

wherein each of $R_2$ and $R_3$ is, independently, bromo, chloro, fluoro, trifluoromethyl, $C_{1-4}$ alkyl, $C_{1-3}$ alkoxy or $C_{3-4}$ alkenyl; and each of n and m is, independently, 0, 1 or 2. When R is naphthyl, it can be either α-naphthyl or β-naphthyl.

Exemplary fluoxetine structural analogs are 3-(p-isopropoxyphenoxy)-3-phenylpropylamine methanesulfonate, N,N-dimethyl 3-(3',4'-dimethoxyphenoxy)-3-phenylpropylamine p-hydroxybenzoate, N,N-dimethyl 3-(α-naphthoxy)-3-phenylpropylamine bromide, N,N-dimethyl 3-(β-naphthoxy)-3-phenyl-1-methylpropylamine iodide, 3-(2'-methyl-4',5'-dichlorophenoxy)-3-phenylpropylamine nitrate, 3-(p-t-butylphenoxy)-3-phenylpropylamine glutarate, N-methyl 3-(2'-chloro-p-tolyloxy)-3-phenyl-1-methylpropylamine lactate, 3-(2',4'-dichlorophenoxy)-3-phenyl-2-methylpropylamine citrate, N,N-dimethyl 3-(m-anisyloxy)-3-phenyl-1-methylpropylamine maleate, N-methyl 3-(p-tolyloxy)-3-phenylpropylamine sulfate, N,N-dimethyl 3-(2',4'-difluorophenoxy)-3-phenylpropylamine 2,4-dinitrobenzoate, 3-(o-ethylphenoxy)-3-phenylpropylamine dihydrogen phosphate, N-methyl 3-(2'-chloro-4'-isopropylphenoxy)-3-phenyl-2-methylpropylamine maleate, N,N-dimethyl 3-(2'-alkyl-4'-fluorophenoxy)-3-phenyl-propylamine succinate, N,N-dimethyl 3-(o-isopropoxyphenoxy)-3-phenyl-propylamine phenylacetate, N,N-dimethyl 3-(o-bromophenoxy)-3-phenyl-propylamine β-phenylpropionate, N-methyl 3-(p-iodophenoxy)-3-phenyl-propylamine propiolate, and N-methyl 3-(3-n-propylphenoxy)-3-phenyl-propylamine decanoate.

Fluvoxamine

Fluvoxamine has the following structure:

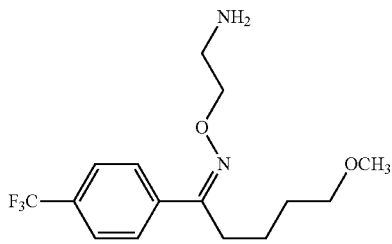

Structural analogs of fluvoxamine are those having the formula:

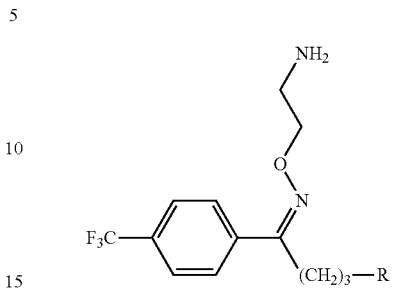

as well as pharmaceutically acceptable salts thereof, wherein R is cyano, cyanomethyl, methoxymethyl, or ethoxymethyl.

Indalpine

Indalpine has the following structure:

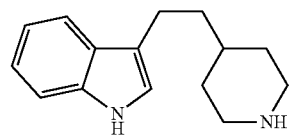

Structural analogs of indalpine are those having the formula:

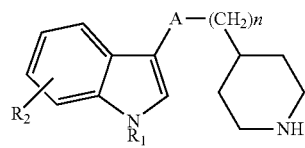

or pharmaceutically acceptable salts thereof, wherein $R_1$ is a hydrogen atom, a $C_1$-$C_4$ alkyl group, or an aralkyl group of which the alkyl has 1 or 2 carbon atoms, $R_2$ is hydrogen, $C_{1-4}$ alkyl, $C_{1-4}$ alkoxy or $C_{1-4}$ alkylthio, chloro, bromo, fluoro, trifluoromethyl, nitro, hydroxy, or amino, the latter optionally substituted by one or two $C_{1-4}$ alkyl groups, an acyl group or a $C_{1-4}$alkylsulfonyl group; A represents —CO or —CH$_2$— group; and n is 0, 1 or 2.

Exemplary indalpine structural analogs are indolyl-3 (piperidyl-4 methyl) ketone; (methoxy-5-indolyl-3)(piperidyl-4 methyl)ketone; (chloro-5-indolyl-3) (piperidyl-4 methyl)ketone; (indolyl-3)-1 (piperidyl-4)-3 propanone, indolyl-3 piperidyl-4 ketone; (methyl-1 indolyl-3)(piperidyl-4 methyl)ketone, (benzyl-1indolyl-3)(piperidyl-4 methyl)ketone; [(methoxy-5 indolyl-3)-2 ethyl]-piperidine, [(methyl-1 indolyl-3)-2 ethyl]-4-piperidine; [(indolyl-3)-2 ethyl]-4 piperidine; (indolyl-3 methyl)-4 piperidine, [(chloro-5 indolyl-3)-2 ethyl]-4 piperidine; [(indolyl-b3)-3 propyl]-4 piperidine; [(benzyl-1 indolyl-3)-2 ethyl]-4 piperidine; and pharmaceutically acceptable salts of any thereof.

Indeloxazine

Indeloxezine has the following structure:

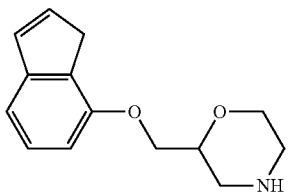

Structural analogs of indeloxazine are those having the formula:

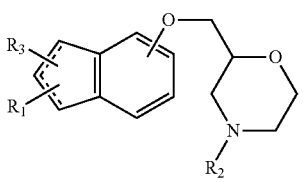

and pharmaceutically acceptable salts thereof, wherein $R_1$ and $R_3$ each represents hydrogen, $C_{1-4}$ alkyl, or phenyl; $R_2$ represents hydrogen, $C_{1-4}$ alkyl, $C_{4-7}$ cycloalkyl, phenyl, or benzyl; one of the dotted lines means a single bond and the other means a double bond, or the tautomeric mixtures thereof.

Exemplary indeloxazine structural analogs are 2-(7-indenyloxymethyl)-4-isopropylmorpholine; 4-butyl-2-(7-indenyloxymethyl)morpholine; 2-(7-indenyloxymethyl)-4-methylmorpholine; 4-ethyl-2-(7-indenyloxymethyl)morpholine, 2-(7-indenyloxymethyl)-morpholine; 2-(7-indenyloxymethyl)-4-propylmorpholine; 4-cyclohexyl-2-(7-indenyloxymethyl)morpholine; 4-benzyl-2-(7-indenyloxymethyl)-morpholine; 2-(7-indenyloxymethyl)-4-phenylmorpholine; 2-(4-indenyloxymethyl)morpholine; 2-(3-methyl-7-indenyloxymethyl)-morpholine; 4-isopropyl-2-(3-methyl-7-indenyloxymethyl)morpholine; 4-isopropyl-2-(3-methyl-4-indenyloxymethyl)morpholine; 4-isopropyl-2-(3-methyl-5-indenyloxymethyl)morpholine; 4-isopropyl-2-(1-methyl-3-phenyl-6-indenyloxymethyl)morpholine; 2-(5-indenyloxymethyl)-4-isopropyl-morpholine, 2-(6-indenyloxymethyl)-4-isopropylmorpholine; and 4-isopropyl-2-(3-phenyl-6-indenyloxymethyl)morpholine; as well as pharmaceutically acceptable salts of any thereof.

Milnacipram

Milnacipram has the following structure:

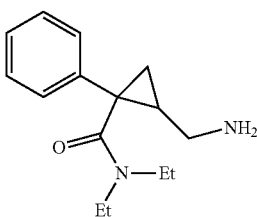

Structural analogs of milnacipram are those having the formula:

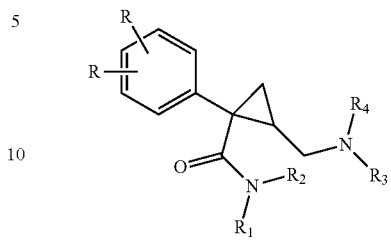

as well as pharmaceutically acceptable salts thereof, wherein each R, independently, represents hydrogen, bromo, chloro, fluoro, $C_{1-4}$ alkyl, $C_{1-4}$ alkoxy, hydroxy, nitro or amino; each of $R_1$ and $R_2$, independently, represents hydrogen, $C_{1-4}$ alkyl, $C_{6-12}$ aryl or $C_{7-14}$ alkylaryl, optionally substituted, preferably in para position, by bromo, chloro, or fluoro, or $R_1$ and $R_2$ together form a heterocycle having 5 or 6 members with the adjacent nitrogen atoms; $R_3$ and R4 represent hydrogen or a $C_{1-4}$ alkyl group or $R_3$ and $R_4$ form with the adjacent nitrogen atom a heterocycle having 5 or 6 members, optionally containing an additional heteroatom selected from nitrogen, sulphur, and oxygen.

Exemplary milnacipram structural analogs are 1-phenyl 1-aminocarbonyl 2-dimethylaminomethyl cyclopropane; 1-phenyl 1-dimethylaminocarbonyl 2-dimethylaminomethyl cyclopropane; 1-phenyl 1-ethylaminocarbonyl 2-dimethylaminomethyl cyclopropane; 1-phenyl 1-diethylaminocarbonyl 2-aminomethyl cyclopropane; 1-phenyl 2-dimethylaminomethyl N-(4'-chlorophenyl)cyclopropane carboxamide; 1-phenyl 2-dimethylaminomethyl N-(4'-chlorobenzyl)cyclopropane carboxamide; 1-phenyl 2-dimethylaminomethyl N-(2-phenylethyl)cyclopropane carboxamide; (3,4-dichloro-1-phenyl) 2-dimethylaminomethyl N,N-dimethylcyclopropane carboxamide; 1-phenyl 1-pyrrolidinocarbonyl 2-morpholinomethyl cyclopropane; 1-p-chlorophenyl 1-aminocarbonyl 2-aminomethyl cyclopropane; 1-orthochlorophenyl 1-aminocarbonyl 2-dimethylaminomethyl cyclopropane; 1-p-hydroxyphenyl 1-aminocarbonyl 2-dimethylaminomethyl cyclopropane; 1-p-nitrophenyl 1-dimethylaminocarbonyl 2-dimethylaminomethyl cyclopropane; 1-p-aminophenyl 1-dimethylaminocarbonyl 2-dimethylaminomethyl cyclopropane; 1-p-tolyl 1-methylaminocarbonyl 2-dimethylaminomethyl cyclopropane; 1-p-methoxyphenyl 1-aminomethylcarbonyl 2-aminomethyl cyclopropane; and pharmaceutically acceptable salts of any thereof.

Paroxetine

Paroxetine has the following structure:

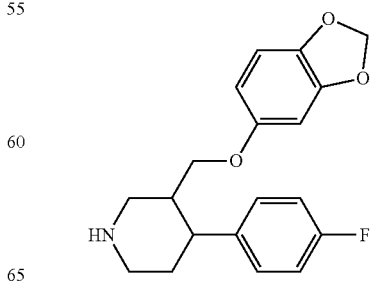

Structural analogs of paroxetine are those having the formula:

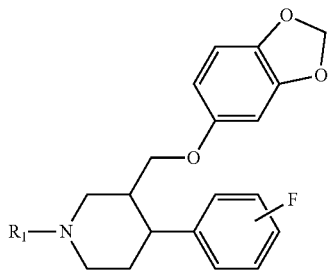

and pharmaceutically acceptable salts thereof, wherein $R_1$ represents hydrogen or a $C_{1-4}$ alkyl group, and the fluorine atom may be in any of the available positions.

Sertraline

Sertraline has the following structure:

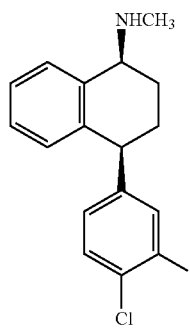

Structural analogs of sertraline are those having the formula:

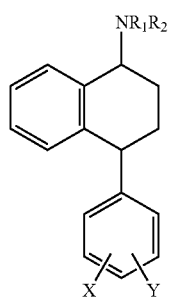

wherein $R_1$ is selected from the group consisting of hydrogen and $C_{1-4}$ alkyl; $R_2$ is $C_{1-4}$ alkyl; X and Y are each selected from the group consisting of hydrogen, fluoro, chloro, bromo, trifluoromethyl, $C_{1-3}$ alkoxy, and cyano; and W is selected from the group consisting of hydrogen, fluoro, chloro, bromo, trifluoromethyl and $C_{1-3}$ alkoxy. Preferred sertraline analogs are in the cis-isomeric configuration. The term "cis-isomeric" refers to the relative orientation of the $NR_1R_2$ and phenyl moieties on the cyclohexene ring (i.e. they are both oriented on the same side of the ring). Because both the 1- and 4-carbons are asymmetrically substituted, each cis- compound has two optically active enantiomeric forms denoted (with reference to the 1-carbon) as the cis-(1R) and cis-(1S) enantiomers.

Particularly useful are the following compounds, in either the (1S)-enantiomeric or (1S)(1R) racemic forms, and their pharmaceutically acceptable salts: cis-N-methyl-4-(3,4-dichlorophenyl)-1,2,3,4-tetrahydro-1-naphthalenamine; cis-N-methyl-4-(4-bromophenyl)-1,2,3,4-tetrahydro-1-naphthalenamine; cis-N-methyl-4-(4-chlorophenyl)-1,2,3,4-tetrahydro-1-naphthalenamine; cis-N-methyl-4-(3-trifluoromethyl-phenyl)-1,2,3,4-tetrahydro-1-naphthalenamine; cis-N-methyl-4-(3-trifluoromethyl-4-chlorophenyl)-1,2,3,4-tetrahydro-1-naphthalenamine; cis-N,N-dimethyl-4-(4-chlorophenyl)-1,2,3,4-tetrahydro-1-naphthalenamine; cis-N,N-dimethyl-4-(3-trifluoromethyl-phenyl)-1,2,3,4-tetrahydro-1-naphthalenamine; and cis-N-methyl-4-(4-chlorophenyl)-7-chloro-1,2,3,4-tetrahydro-1-naphthalenamine. Of interest also is the (1R)-enantiomer of cis-N-methyl-4-(3,4-dichlorophenyl)-1,2,3,4-tetrahydro-1-naphthalenamine.

Sibutramine hydrochloride monohydrate

Sibutramine hydrochloride monohydrate (MERIDIA™) is an orally administered agent for the treatment of obesity. Sibutramine hydrochloride is a racemic mixture of the (+) and (−) enantiomers of cyclobutanemethanamine, 1-(4-chlorophenyl)-N,N-dimethyl-(alpha)-(2-methylpropyl)-, hydrochloride, monohydrate. Each MERIDIA™ capsule contains 5 mg, 10 mg, or 15 mg of sibutramine hydrochloride monohydrate. The recommended starting dose of MERIDIA™ is 10 mg administered once daily with or without food. If there is inadequate weight loss, the dose may be titrated after four weeks to a total of 15 mg once daily. The 5 mg dose is typically reserved for patients who do not tolerate the 10 mg dose.

Zimeldine

Zimeldine has the following structure:

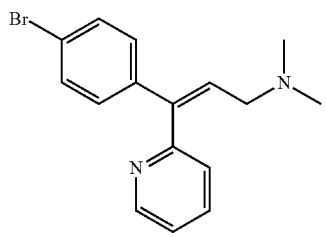

Structural analogs of zimeldine are those compounds having the formula:

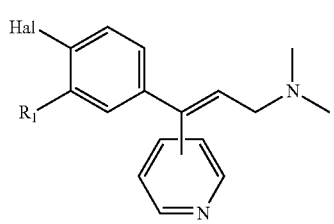

and pharmaceutically acceptable salts thereof, wherein the pyridine nucleus is bound in ortho-, meta- or para-position to the adjacent carbon atom and where $R_1$ is selected from the group consisting of H, chloro, fluoro, and bromo.

Exemplary zimeldine analogs are (e)- and (z)-3-(4'-bromophenyl-3-(2"-pyridyl) -dimethylallylamine; 3-(4'-bromophenyl)-3-(3"-pyridyl)-dimethylallylamine; 3-(4'-bromophenyl)-3-(4"-pyridyl)-dimethylallylamine; and pharmaceutically acceptable salts of any thereof.

Structural analogs of any of the above SSRIs are considered herein to be SSRI analogs and thus may be employed in any of the methods, compositions, and kits of the invention.

Metabolites

Pharmacologically active metabolites of any of the foregoing SSRIs can also be used in the methods, compositions, and kits of the invention. Exemplary metabolites are didesmethylcitalopram, desmethylcitalopram, desmethylsertraline, and norfluoxetine.

Analogs

Functional analogs of SSRIs can also be used in the methods, compositions, and kits of the invention. Exemplary SSRI functional analogs are provided below. One class of SSRI analogs includes SNRIs (selective serotonin norepinephrine reuptake inhibitors), which include venlafaxine, duloxetine, and 4-(2-fluorophenyl)-6-methyl-2-piperazinothieno[2,3-d]pyrimidine.

Venlafaxine

Venlafaxine hydrochloride (EFFEXOR™) is an antidepressant for oral administration. It is designated (R/S)-1-[2-(dimethylamino)-1-(4-methoxyphenyl)ethyl]cyclohexanol hydrochloride or (±)-1-[(alpha)-[(dimethyl-amino)methyl]-p-methoxybenzyl]cyclohexanol hydrochloride. Compressed tablets contain venlafaxine hydrochloride equivalent to 25 mg, 37.5 mg, 50 mg, 75 mg, or 100 mg venlafaxine. The recommended starting dose for venlafaxine is 75 mg/day, administered in two or three divided doses, taken with food. Depending on tolerability and the need for further clinical effect, the dose may be increased to 150 mg/day. If desirable, the dose can be further increased up to 225 mg/day. When increasing the dose, increments of up to 75 mg/day are typically made at intervals of no less than four days.

Venlafaxine has the following structure:

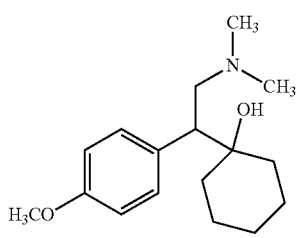

Structural analogs of venlafaxine are those compounds having the formula:

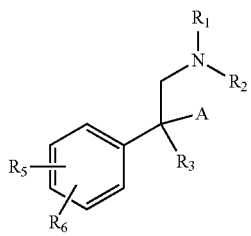

as well as pharmaceutically acceptable salts thereof, wherein A is a moiety of the formula:

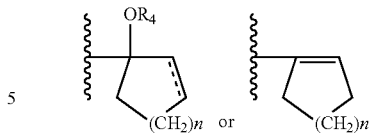

where the dotted line represents optional unsaturation; $R_1$ is hydrogen or alkyl; $R_2$ is $C_{1-4}$ alkyl; $R_4$ is hydrogen, $C_{1-4}$ alkyl, formyl or alkanoyl; $R_3$ is hydrogen or $C_{1-4}$ alkyl; $R_5$ and $R_6$ are, independently, hydrogen, hydroxyl, $C_{1-4}$ alkyl, $C_{1-4}$ alkoxy, $C_{1-4}$ alkanoyloxy, cyano, nitro, alkylmercapto, amino, $C_{1-4}$ alkylamino, dialkylamino, $C_{1-4}$ alkanamido, halo, trifluoromethyl or, taken together, methylenedioxy; and n is 0, 1, 2, 3 or 4.

Duloxetine

Duloxetine has the following structure:

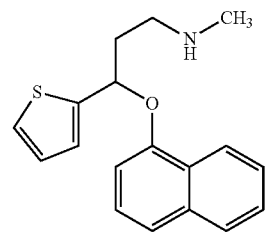

Structural analogs of duloxetine are those compounds described by the formula disclosed in U.S. Pat. No. 4,956,388, hereby incorporated by reference.

Other SSRI analogs are 4-(2-fluorophenyl)-6-methyl-2-piperazinothieno[2,3-d]pyrimidine, 1,2,3,4-tetrahydro-N-methyl-4-phenyl-1-naphthylamine hydrochloride; 1,2,3,4-tetrahydro-N-methyl-4-phenyl-(E)-1-naphthylamine hydrochloride; N,N-dimethyl-1-phenyl-1-phthalanpropylamine hydrochloride; gamma-(4-(trifluoromethyl)phenoxy)-benzenepropanamine hydrochloride; BP 554; CP 53261; O-desmethylvenlafaxine; WY 45,818; WY 45,881; N-(3-fluoropropyl)paroxetine; Lu 19005; and SNRIs described in PCT Publication No. WO04/004734.

Standard Recommended Dosages

Standard recommended dosages for exemplary SSRIs are provided in Table 4, below. Other standard dosages are provided, e.g., in the Merck Manual of Diagnosis & Therapy (17th Ed. M H Beers et al., Merck & Co.) and Physicians' Desk Reference 2003 (57th Ed. Medical Economics Staff et al., Medical Economics Co., 2002).

TABLE 4

| Compound | Standard Dose |
| --- | --- |
| Fluoxetine | 20-80 mg/day |
| Sertraline | 50-200 mg/day |
| Paroxetine | 20-50 mg/day |
| Fluvoxamine | 50-300 mg/day |
| Citalopram | 10-80 mg qid |
| Escitalopram | 10 mg qid |

Other Compounds

Other compounds that may be used as a substitute for or in addition to a corticosteroid in the methods, compositions, and kits of the invention A-348441 (Karo Bio), adrenal cortex extract (GlaxoSmithKline), alsactide (Aventis), amebucort (Schering AG), amelometasone (Taisho), ATSA (Pfizer), bitolterol (Elan), CBP-2011 (InKine Pharmaceutical), cebaracetam (Novartis) CGP-13774 (Kissei), ciclesonide (Altana), ciclometasone (Aventis), clobetasone butyrate (GlaxoSmithKline), cloprednol (Hoffmann-La Roche), collismycin A (Kirin), cucurbitacin E (NIH), deflazacort (Aventis), deprodone propionate (SSP), dexamethasone acefurate (Schering-Plough), dexamethasone linoleate (GlaxoSmithKline), dexamethasone valerate (Abbott), difluprednate (Pfizer), domoprednate (Hoffmann-La Roche), ebiratide (Aventis), etiprednol dicloacetate (IVAX), fluazacort (Vicuron), flumoxonide (Hoffmann-La Roche), fluocortin butyl (Schering AG), fluocortolone monohydrate (Schering AG), GR-250495X (GlaxoSmithKline), halometasone (Novartis), halopredone (Dainippon), HYC-141 (Fidia), icomethasone enbutate (Hovione), itrocinonide (AstraZeneca), L-6485 (Vicuron), Lipocort (Draxis Health), locicortone (Aventis), meclorisone (Schering-Plough), naflocort (Bristol-Myers Squibb), NCX-1015 (NicOx), NCX-1020 (NicOx), NCX-1022 (NicOx), nicocortonide (Yamanouchi), NIK-236 (Nikken Chemicals), NS-126 (SSP), Org-2766 (Akzo Nobel), Org-6632 (Akzo Nobel), P16CM, propylmesterolone (Schering AG), RGH-1113 (Gedeon Richter), rofleponide (AstraZeneca), rofleponide palmitate (AstraZeneca), RPR-106541 (Aventis), RU-26559 (Aventis), Sch-19457 (Schering-Plough), T25 (Matrix Therapeutics), TBI-PAB (Sigma-Tau), ticabesone propionate (Hoffmann-La Roche), tifluadom (Solvay), timobesone (Hoffmann-La Roche), TSC-5 (Takeda), and ZK-73634 (Schering AG).

Non-Steroidal Anti-Inflammatory Drugs (NSAIDs)

If desired, the tetra-substituted pyrimidopyrimidines of the invention may be administered in conjunction with one or more of non-steroidal anti-inflammatory drugs (NSAIDs), such as naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin.

When tetra-substituted pyrimidopyrimidines is administered in combination with acetylsalicylic acid, it is desirable that the combination is effective in suppressing TNFα, IL-1, IL-2 or IFN-γ in vitro. Accordingly, the combination of tetra-substituted pyrimidopyrimidine or tetra-substituted pyrimidopyrimidine analog in combination with acetylsalicylic acid and their analogs may be more effective in treating immunoinflammatory diseases, particulary those mediated by TNFα, IL-1, IL-2 or IFN-γ than either agent alone.

Acetylsalicylic acid, also known by trade name aspirin, is an acetyl derivative of salicylic acid and has the following structural formula.

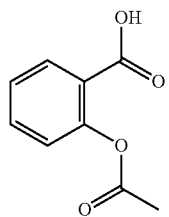

Aspirin is useful in the relief of headache and muscle and joint aches. Aspirin is also effective in reducing fever, inflammation, and swelling and thus has been used for treatment of rheumatoid arthritis, rheumatic fever, and mild infection. Thus in one aspect, combination of a tetra-substituted pyrimidopyrimidine or analog thereof (e.g., dipyridamole) and acetylsalicylic acid (aspirin) or analog thereof can also be administered to enhance the treatment or prevention of the diseases mentioned above.

An NSAID may be administered in conjunction with any one of the combinations described in this application. For example, a patient suffering from immunoinflammatory disorder may be initially treated with a combination of a tetra-substituted pyrimidopyrimidine/SSRI or tetra-substituted pyrimidopyrimidine/glucocorticoid receptor modulator or tetra-substituted pyrimidopyrimidine/antihistamine or tetra-substituted pyrimidopyrimidine/ibudilast combination and then the patient may also be treated with an NSAID, such as acetylsalicylic acid, in conjunction with the combinations described above.

Dosage amounts of acetylsalicylic acid are known to those skilled in medical arts, and generally range from about 70 mg to about 350 mg per day. When a lower or a higher dose of aspirin is needed, a formulation containing dipyridamole and aspirin may contain 0-25 mg, 25-50 mg, 50-70 mg, 70-75 mg, 75-80 mg, 80-85 mg, 85-90 mg, 90-95 mg, 95-100 mg, 100-150 mg, 150-160 mg, 160-250 mg, 250-300mg, 300-350 mg, or 350-1000 mg of aspirin.

When the combinations of the invention are used for treatment in conjunction with an NSAIDs it is possible to reduce the dosage of the individual components substantially to a point far below the dosages which would be required to achieve the same effects by administering NSAIDs (e.g., acetylsalicylic acid) or tetra-substituted pyrimidopyrimidines alone or by administering a combination of NSAIDs (e.g., acetylsalicylic acid) and tetra-substituted pyrimidopyrimidines.

In one aspect, the composition comprising tetra-substituted pyrimidopyrimidine and an NSAID has increased effectiveness, safety, tolerability, or satisfaction of treatment of a patient suffering from or at risk of suffering from immunoinflammatory disorder as compared to a composition having a tetra-substituted pyrimidopyrimidine or a NSAID alone.

Nonsteroidal Immunophilin-dependent Immunosuppressants

In one embodiment, the invention features methods, compositions, and kits employing an SSRI and a non-steroidal immunophilin-dependent immunosuppressant (NsIDI), optionally with a corticosteroid or other agent described herein.

In healthy individuals the immune system uses cellular effectors, such as B-cells and T-cells, to target infectious microbes and abnormal cell types while leaving normal cells intact. In individuals with an autoimmune disorder or a transplanted organ, activated T-cells damage healthy tissues. Calcineurin inhibitors (e.g., cyclosporines, tacrolimus, pimecrolimus), and rapamycin target many types of immunoregulatory cells, including T-cells, and suppress the immune response in organ transplantation and autoimmune disorders.

In one embodiment, the NsIDI is cyclosporine, and is administered in an amount between 0.05 and 50 milligrams per kilogram per day (e.g., orally in an amount between 0.1 and 12 milligrams per kilogram per day). In another embodiment, the NsIDI is tacrolimus and is administered in an amount between 0.0001-20 milligrams per kilogram per day (e.g., orally in an amount between 0.01-0.2 milligrams per kilogram per day). In another embodiment, the NsIDI is rapamycin and is administered in an amount between 0.1-502 milligrams per day (e.g., at a single loading dose of 6 mg/day, followed by a 2 mg/day maintenance dose). In another embodiment, the NsIDI is everolimus, administered at a dosage of 0.75-8 mg/day. In still other embodiments, the NsIDI is pimecrolimus, administered in an amount between 0.1 and 200 milligrams per day (e.g., as a 1% cream/twice a day to treat atopic dermatitis or 60 mg a day for the treatment of psoriasis), or the NsIDI is a calcineurin-binding peptide administered in an amount and frequency sufficient to treat the patient. Two or more NsIDIs can be administered contemporaneously.

Cyclosporines

The cyclosporines are fungal metabolites that comprise a class of cyclic oligopeptides that act as immunosuppressants. Cyclosporine A is a hydrophobic cyclic polypeptide consisting of eleven amino acids. It binds and forms a complex with the intracellular receptor cyclophilin. The cyclosporine/cyclophilin complex binds to and inhibits calcineurin, a $Ca^{2+}$-calmodulin-dependent serine-threonine-specific protein phosphatase. Calcineurin mediates signal transduction events required for T-cell activation (reviewed in Schreiber et al., Cell 70:365-368, 1991). Cyclosporines and their functional and structural analogs suppress the T cell-dependent immune response by inhibiting antigen-triggered signal transduction. This inhibition decreases the expression of proinflammatory cytokines, such as IL-2.

Many different cyclosporines (e.g., cyclosporine A, B, C, D, E, F, G, H, and I) are produced by fungi. Cyclosporine A is a commercially available under the trade name NEORAL from Novartis. Cyclosporine A structural and functional analogs include cyclosporines having one or more fluorinated amino acids (described, e.g., in U.S. Pat. No. 5,227,467); cyclosporines having modified amino acids (described, e.g., in U.S. Pat. Nos. 5,122,511 and 4,798,823); and deuterated cyclosporines, such as ISAtx247 (described in U.S. Patent Application Publication No. 2002/0132763 A1). Additional cyclosporine analogs are described in U.S. Pat. Nos. 6,136, 357, 4,384,996, 5,284,826, and 5,709,797. Cyclosporine analogs include, but are not limited to, D-Sar (α-SMe)$^3$ Val$^2$-DH-Cs (209-825), Allo-Thr-2-Cs, Norvaline-2-Cs, D-Ala(3-acetylamino)-8-Cs, Thr-2-Cs, and D-MeSer-3-Cs, D-Ser (O—CH$_2$CH$_2$—OH)-8-Cs, and D-Ser-8-Cs, which are described in Cruz et al. (Antimicrob. Agents Chemother. 44:143-149, 2000). Cyclosporines are highly hydrophobic and readily precipitate in the presence of water (e.g. on contact with body fluids). Methods of providing cyclosporine formulations with improved bioavailability are described in U.S. Pat. Nos. 4,388,307, 6,468,968, 5,051,402, 5,342,625, 5,977,066, and 6,022,852. Cyclosporine microemulsion compositions are described in U.S. Pat. Nos. 5,866,159, 5,916,589, 5,962,014, 5,962,017, 6,007,840, and 6,024,978.

Cyclosporines can be administered either intravenously or orally, but oral administration is preferred. To overcome the hydrophobicity of cyclosporine A, an intravenous cyclosporine A is usually provided in an ethanol-polyoxyethylated castor oil vehicle that must be diluted prior to administration. Cyclosporine A may be provided, e.g., as a microemulsion in a 25 mg or 100 mg tablets, or in a 100 mg/ml oral solution (NEORAL).

Typically, patient dosage of an oral cyclosporine varies according to the patient's condition, but some standard recommended dosages are provided herein. Patients undergoing organ transplant typically receive an initial dose of oral cyclosporine A in amounts between 12 and 15 mg/kg/day. Dosage is then gradually decreased by 5% per week until a 7-12 mg/kg/day maintenance dose is reached. For intravenous administration 2-6 mg/kg/day is preferred for most patients. For patients diagnosed as having Crohn's disease or ulcerative colitis, dosage amounts from 6-8 mg/kg/day are generally given. For patients diagnosed as having systemic lupus erythematosus, dosage amounts from 2.2-6.0 mg/kg/day are generally given. For psoriasis or rheumatoid arthritis, dosage amounts from 0.5-4 mg/kg/day are typical. A suggested dosing schedule is shown in Table 5. Other useful dosages include 0.5-5 mg/kg/day, 5-10 mg/kg/day, 10-15 mg/kg/day, 15-20 mg/kg/day, or 20-25 mg/kg/day. Often cyclosporines are administered in combination with other immunosuppressive agents, such as glucocorticoids.

TABLE 5

| Compound | Atopic Dermatitis | Psoriasis | RA | Crohn's | UC | Transplant | SLE |
| --- | --- | --- | --- | --- | --- | --- | --- |
| CsA (NEORAL) | N/A | 0.5–4 mg/kg/day | 0.5–4 mg/kg/day | 6–8 mg/kg/day (oral-fistulizing) | 6–8 mg/kg/day (oral) | ~7–12 mg/kg/day | 2.2–6.0 mg/kg/day |
| Tacrolimus | 0.03–0.1% cream/twice day (30 and 60 gram tubes) | 0.05–1.15 mg/kg/day (oral) | 1–3 mg/day (oral) | 0.1–0.2 mg/kg/day (oral) | 0.1–0.2 mg/kg/day (oral) | 0.1–0.2 mg/kg/day (oral) | N/A |
| Pimecrolimus | 1% cream/twice day (15, 30, 100 gram tubes) | 40–60 mg/day (oral) | 40–60 mg/day (oral) | 80–160 mg/day (oral) | 160–240 mg/day (oral) | 40–120 mg/day (oral) | 40–120 mg/day (oral) |

Table Legend
CsA = cyclosporine A
RA = rheumatoid arthritis
UC = ulcerative colitis
SLE = systemic lupus erythamatosus Tacrolimus Tacrolimus (FK506) is an immunosuppressive agent that targets T cell intracellular signal transduction pathways. Tacrolimus binds to an intracellular protein FK506 binding protein (FKBP-12) that is not structurally related to cyclophilin (Harding et al. Nature 341:758-7601, 1989; Siekienka et al. Nature 341:755-757, 1989; and Soltoff et al., J. Biol. Chem. 267:17472-17477, 1992). The FKBP/FK506 complex binds to calcineurin and inhibits calcineurin's phosphatase activity. This inhibition prevents the dephosphorylation and nuclear translocation of nuclear factor of activated T cells (NFAT), a nuclear component that initiates gene transcription required for proinflammatory cytokine (e.g., IL-2, gamma interferon) production and T cell activation. Thus, tacrolimus inhibits T cell activation.

Tacrolimus is a macrolide antibiotic that is produced by *Streptomyces tsukubaensis*. It suppresses the immune system and prolongs the survival of transplanted organs. It is currently available in oral and injectable formulations. Tacrolimus capsules contain 0.5 mg, 1 mg, or 5 mg of anhydrous tacrolimus within a gelatin capsule shell. The injectable formulation contains 5 mg anhydrous tacrolimus in castor oil and alcohol that is diluted with 0.9% sodium chloride or 5% dextrose prior to injection. While oral administration is preferred, patients unable to take oral capsules may receive injectable tacrolimus. The initial dose should be administered no sooner than six hours after transplant by continuous intravenous infusion.

Tacrolimus and tacrolimus analogs are described by Tanaka et al., (J. Am. Chem. Soc., 109:5031, 1987) and in U.S. Pat. Nos. 4,894,366, 4,929,611, and 4,956,352. FK506-related compounds, including FR-900520, FR-900523, and FR-900525, are described in U.S. Pat. No. 5,254,562; O-aryl, O-alkyl, O-alkenyl, and O-alkynylmacrolides are described in U.S. Pat. Nos. 5,250,678, 532,248, 5,693,648; amino O-aryl macrolides are described in U.S. Pat. No. 5,262,533; alkylidene macrolides are described in U.S. Pat. No. 5,284,840; N-heteroaryl, N-alkylheteroaryl, N-alkenylheteroaryl, and N-alkynylheteroaryl macrolides are described in U.S. Pat. No. 5,208,241; aminomacrolides and derivatives thereof are described in U.S. Pat. No. 5,208,228; fluoromacrolides are described in U.S. Pat. No. 5,189,042; amino O-alkyl, O-alkenyl, and O-alkynylmacrolides are described in U.S. Pat. No. 5,162,334; and halomacrolides are described in U.S. Pat. No. 5,143,918.

While suggested dosages will vary with a patient's condition, standard recommended dosages are provided below. Typically patients diagnosed as having Crohn's disease or ulcerative colitis are administered 0.1-0.2 mg/kg/day oral tacrolimus. Patients having a transplanted organ typically receive doses of 0.1-0.2 mg/kg/day of oral tacrolimus. Patients being treated for rheumatoid arthritis typically receive 1-3 mg/day oral tacrolimus. For the treatment of psoriasis, 0.01-0.15 mg/kg/day of oral tacrolimus is administered to a patient. Atopic dermatitis can be treated twice a day by applying a cream having 0.03-0.1% tacrolimus to the affected area. Patients receiving oral tacrolimus capsules typically receive the first dose no sooner than six hours after transplant, or eight to twelve hours after intravenous tacrolimus infusion was discontinued. Other suggested tacrolimus dosages include 0.005-0.01 mg/kg/day, 0.01-0.03 mg/kg/day, 0.03-0.05 mg/kg/day, 0.05-0.07 mg/kg/day, 0.07-0.10 mg/kg/day, 0.10-0.25 mg/kg/day, or 0.25-0.5 mg/kg/day.

Tacrolimus is extensively metabolized by the mixed-function oxidase system, in particular, by the cytochrome P-450 system. The primary mechanism of metabolism is demethylation and hydroxylation. While various tacrolimus metabolites are likely to exhibit immunosuppressive biological activity, the 13-demethyl metabolite is reported to have the same activity as tacrolimus.

Pimecrolimus

Pimecrolimus is the 33-epi-chloro derivative of the macrolactam ascomyin. Pimecrolimus structural and functional analogs are described in U.S. Pat. No. 6,384,073. Pimecrolimus is particularly useful for the treatment of atopic dermatitis. Pimecrolimus is currently available as a 1% cream. Suggested dosing schedule for pimecrolimus is shown at Table 5. While individual dosing will vary with the patient's condition, some standard recommended dosages are provided below. Oral pimecrolimus can be given for the treatment of psoriasis or rheumatoid arthritis in amounts of 40-60 mg/day. For the treatment of Crohn's disease or ulcerative colitis amounts of 80-160 mg/day pimecrolimus can be given. Patients having an organ transplant can be administered 160-240 mg/day of pimecrolimus. Patients diagnosed as having systemic lupus erythamatosus can be administered 40-120 mg/day of pimecrolimus. Other useful dosages of pimecrolimus include 0.5-5 mg/day, 5-10 mg/day, 10-30 mg/day, 40-80 mg/day, 80-120 mg/day, or even 120-200 mg/day.

Rapamycin

Rapamycin is a cyclic lactone produced by *Streptomyces hygroscopicus*. Rapamycin is an immunosuppressive agent that inhibits T cell activation and proliferation. Like cyclosporines and tacrolimus, rapamycin forms a complex with the immunophilin FKBP-12, but the rapamycin-FKBP-12 complex does not inhibit calcineurin phosphatase activity. The rapamycin immunophilin complex binds to and inhibits the mammalian kinase target of rapamycin (mTOR). mTOR is a kinase that is required for cell-cycle progression. Inhibition of mTOR kinase activity blocks T cell activation and proinflammatory cytokine secretion.

Rapamycin structural and functional analogs include mono- and diacylated rapamycin derivatives (U.S. Pat. No. 4,316,885); rapamycin water-soluble prodrugs (U.S. Pat. No. 4,650,803); carboxylic acid esters (PCT Publication No. WO 92/05179); carbamates (U.S. Pat. No. 5,118,678); amide esters (U.S. Pat. No. 5,118,678); biotin esters (U.S. Pat. No. 5,504,091); fluorinated esters (U.S. Pat. No. 5,100,883); acetals (U.S. Pat. No. 5,151,413); silyl ethers (U.S. Pat. No. 5,120,842); bicyclic derivatives (U.S. Pat. No. 5,120,725); rapamycin dimers (U.S. Pat. No. 5,120,727); O-aryl, O-alkyl, O-alkyenyl and O-alkynyl derivatives (U.S. Pat. No. 5,258,389); and deuterated rapamycin (U.S. Pat. No. 6,503,921). Additional rapamycin analogs are described in U.S. Pat. Nos. 5,202,332 and 5,169,851.

Rapamycin is currently available for oral administration in liquid and tablet formulations. RAPAMUNE liquid contains 1 mg/mL rapamycin that is diluted in water or orange juice prior to administration. Tablets containing 1 or 2 mg of rapamycin are also available. Rapamycin is preferably given once daily as soon as possible after transplantation. It is absorbed rapidly and completely after oral administration. Typically, patient dosage of rapamycin varies according to the patient's condition, but some standard recommended dosages are provided below. The initial loading dose for rapamycin is 6 mg. Subsequent maintenance doses of 0.5-2 mg/day are typical. Alternatively, a loading dose of 3 mg, 5 mg, 10 mg, 15 mg, 20 mg, or 25 mg can be used with a 1 mg, 3 mg, 5 mg, 7 mg, or 10 mg per day maintenance dose. In patients weighing less than 40 kg, rapamycin dosages are typically adjusted based on body surface area; generally a 3 mg/m$^2$/day loading dose and a 1 mg/m$^2$/day maintenance dose is used.

Peptide Moieties

Peptides, peptide mimetics, peptide fragments, either natural, synthetic or chemically modified, that impair the calcineurin-mediated dephosphorylation and nuclear translocation of NFAT are suitable for use in practicing the invention. Examples of peptides that act as calcineurin inhibitors by inhibiting the NFAT activation and the NFAT transcription factor are described, e.g., by Aramburu et al., Science 285: 2129-2133, 1999) and Aramburu et al., Mol. Cell 1:627-637, 1998). As a class of calcineurin inhibitors, these agents are useful in the methods of the invention.

Therapy

The invention features methods for suppressing secretion of proinflammatory cytokines as a means for treating an immunoinflammatory disorder, proliferative skin disease, organ transplant rejection, or graft versus host disease.

Therapy according to the invention may be performed alone or in conjunction with another therapy and may be provided at home, the doctor's office, a clinic, a hospital's outpatient department, or a hospital. The duration of the therapy depends on the type of disease or disorder being treated, the age and condition of the patient, the stage and type of the patient's disease, and how the patient responds to the treatment. Additionally, a person having a greater risk of developing an inflammatory disease (e.g., a person who is undergoing age-related hormonal changes) may receive treatment to inhibit or delay the onset of symptoms.

In particular embodiments of any of the methods of the invention, the compounds are administered within 10 days of each other, within five days of each other, within twenty-four hours of each other, or simultaneously. The compounds may be formulated together as a single composition, or may be formulated and administered separately. One or both compounds may be administered in a low dosage or in a high dosage, each of which is defined herein. It may be desirable to administer to the patient other compounds, such as a corticosteroid, NSAID (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid, fenoprofen, flurbiprofen, ketoprofen, meclofenamate sodium, meloxicam, oxaprozin, sulindac, and tolmetin), COX-2 inhibitor (e.g., rofecoxib, celecoxib, valdecoxib, and lumiracoxib), glucocorticoid receptor modulator, or DMARD. Combination therapies of the invention are especially useful for the treatment of immunoinflammatory disorders in combination with other agents—either biologics or small molecules—that modulate the immune response to positively affect disease. Such agents include those that deplete key inflammatory cells, influence cell adhesion, or influence cytokines involved in immune response. This last category includes both agents that mimic or increase the action of anti-inflammatory cytokines such as IL-10, as well as agents inhibit the activity of pro-inflammatory cytokines such as IL-6, IL-1, IL-2, IL-12, IL-15 or TNFα. Agents that inhibit TNFα include etanercept, adelimumab, infliximab, and CDP-870. In this example (that of agents blocking the effect of TNFα), the combination therapy reduces the production of cytokines, etanercept or infliximab act on the remaining fraction of inflammatory cytokines, providing enhanced treatment. Small molecule immunodulators include, e.g., p38 MAP kinase inhibitors such as VX 702, SCIO 469, doramapimod, RO 30201195, SCIO 323, TACE inhibitors such as DPC 333, ICE inhibitors such as pranalcasan, and IMPDH inhibitors such as mycophenolate and merimepodib.

In combination therapy, the dosage and frequency of administration of each component of the combination can be controlled independently. For example, one compound may be administered three times per day, while the second compound may be administered once per day. Combination therapy may be given in on-and-off cycles that include rest periods so that the patient's body has a chance to recover from any as yet unforeseen side effects. The compounds may also be formulated together such that one administration delivers both compounds.

The compound in question may be administered orally in the form of tablets, capsules, elixirs or syrups, or rectally in the form of suppositories. Parenteral administration of a compound is suitably performed, for example, in the form of saline solutions or with the compound incorporated into liposomes. In cases where the compound in itself is not sufficiently soluble to be dissolved, a solubilizer such as ethanol can be applied.

Desirably, the methods, compositions, and kits of the invention are more effective than other methods, compositions, and kits. By "more effective" is meant that a method, composition, or kit exhibits greater efficacy, is less toxic, safer, more convenient, better tolerated, or less expensive, or provides more treatment satisfaction than another method, composition, or kit with which it is being compared.

Chronic Obstructive Pulmonary Disease

In one embodiment, the methods, compositions, and kits of the invention are used for the treatment of chronic obstructive pulmonary disease (COPD). If desired, one or more agents typically used to treat COPD may be used as a substitute for or in addition to a corticosteroid in the methods, compositions, and kits of the invention. Such agents include xanthines (e.g., theophylline), anticholinergic compounds (e.g., ipratropium, tiotropium), biologics, small molecule immunomodulators, and beta receptor agonists/bronchdilators (e.g., ibuterol sulfate, bitolterol mesylate, epinephrine, formoterol fumarate, isoproteronol, levalbuterol hydrochloride, metaproterenol sulfate, pirbuterol scetate, salmeterol xinafoate, and terbutaline). Thus, in one embodiment, the invention features the combination of a tetra-substituted pyrimidopyrimidine and a bronchodilator, and methods of treating COPD therewith.

Psoriasis

The methods, compositions, and kits of the invention may be used for the treatment of psoriasis. If desired, one or more antipsoriatic agents typically used to treat psoriasis may be used as a substitute for or in addition to a corticosteroid in the methods, compositions, and kits of the invention. Such agents include biologics (e.g., alefacept, infliximab, adelimumab, efalizumab, etanercept, and CDP-870), small molecule immunomodulators (e.g., VX 702, SCIO 469, doramapimod, RO 30201195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), vitamin D analogs (e.g., calcipotriene, calcipotriol), psoralens (e.g., methoxsalen), retinoids (e.g., acitretin, tazoretene), DMARDs (e.g., methotrexate), and anthralin. Thus, in one embodiment, the invention features the combination of a tetra-substituted pyrimidopyrimidine and an antipsoriatic agent, and methods of treating psoriasis therewith.

Inflammatory Bowel Disease

The methods, compositions, and kits of the invention may be used for the treatment of inflammatory bowel disease. If desired, one or more agents typically used to treat inflammatory bowel disease may be used as a substitute for or in addition to a corticosteroid in the methods, compositions, and kits of the invention. Such agents include biologics (e.g., inflixamab, adelimumab, and CDP-870), small molecule immunomodulators (e.g., VX 702, SCIO 469, doramapimod, RO 30201195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), 5-amino salicylic acid (e.g., mesalamine, sulfasalazine, balsalazide disodium, and olsalazine sodium), DMARDs (e.g., methotrexate and azathioprine) and alosetron. Thus, in one embodiment, the invention features the combination of a tetra-substituted pyrimidopyrimidine and any of the foregoing agents, and methods of treating inflammatory bowel disease therewith.

Rheumatoid Arthritis

The methods, compositions, and kits of the invention may be used for the treatment of rheumatoid arthritis. If desired, one or more agents typically used to treat rheumatoid arthritis may be used as a substitute for or in addition to a corticosteroid in the methods, compositions, and kits of the invention. Such agents include NSAIDs (e.g., naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin), COX-2 inhibitors (e.g., rofecoxib, celecoxib, valdecoxib, and lumiracoxib), biologics (e.g., inflixamab, adelimumab, etanercept, CDP-870, rituximab, and atlizumab), small molecule immunomodulators (e.g., VX 702, SCIO 469, doramapimod, RO 30201195, SCIO 323, DPC 333, pranalcasan, mycophenolate, and merimepodib), non-steroidal immunophilin-dependent immunosuppressants (e.g., cyclosporine, tacrolimus, pimecrolimus, and ISAtx247), 5-amino salicylic acid (e.g., mesalamine, sulfasalazine, balsalazide disodium, and olsalazine sodium), DMARDs (e.g., methotrexate, leflunomide, minocycline, auranofin, gold sodium thiomalate, aurothioglucose, and azathioprine), hydroxychloroquine sulfate, and penicillamine. Thus, in one embodiment, the invention features the combination of a tetra-substituted pyrimidopyrimidine with any of the foregoing agents, and methods of treating rheumatoid arthritis therewith.

Asthma

The methods, compositions, and kits of the invention may be used for the treatment of asthma. If desired, one or more agents typically used to treat asthma may be used as a substitute for or in addition to a corticosteroid in the methods, compositions, and kits of the invention. Such agents include beta 2 agonists/bronchodilators/leukotriene modifiers (e.g., zafirlukast, montelukast, and zileuton), biologics (e.g., omalizumab), small molecule immunomodulators, anticholinergic compounds, xanthines, ephedrine, guaifenesin, cromolyn sodium, nedocromil sodium, and potassium iodide. Thus, in one embodiment, the invention features the combination of a tetra-substituted pyrimidopyrimidine and any of the foregoing agents, and methods of treating asthma therewith.

Formulation of Compositions

The administration of a combination of the invention may be by any suitable means that results in suppression of proinflammatory cytokine levels at the target region. The compound may be contained in any appropriate amount in any suitable carrier substance, and is generally present in an amount of 1-95% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

Each compound of the combination may be formulated in a variety of ways that are known in the art. For example, the first and second agents may be formulated together or separately. Desirably, the first and second agents are formulated together for the simultaneous or near simultaneous administration of the agents. Such co-formulated compositions can include, for example, the tetra-substituted pyrimidopyrimidine and the antihistamine formulated together in the same pill, capsule, liquid, etc. It is to be understood that, when referring to the formulation of "tetra-substituted pyrimidopyrimidine/antihistamine," the formulation technology employed is also useful for the formulation of the individual agents of the combination, as well as other combinations of the invention (e.g., a tetra-substituted pyrimidopyrimidine/SSRI or tetra-substituted pyrimidopyrimidine/glucocorticoid receptor modulator combination). By using different formulation strategies for different agents, the pharmacokinetic profiles for each agent can be suitably matched.

The individually or separately formulated agents can be packaged together as a kit. Non-limiting examples include kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Controlled and/or Extended Release Formulations

Administration of any one of the combinations of this invention, for example, the tetra-substituted pyrimidopyrimidine/antihistamine combination in which one or both of the active agents is formulated for controlled and/or extended release is useful where the tetra-substituted pyrimidopyrimidine or the antihistamine, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; (iii) a short biological half-life; or (iv) the pharmacokinetic profile of each component must be modified to maximize the contribution of each agent, when used together, to an amount of that is therapeutically effective for cytokine suppression. Accordingly, a sustained release formulation may be used to avoid frequent dosing that may be required in order to sustain the plasma levels of both agents at a therapeutic level. For example, in preferable oral compositions of the invention, half-life and mean residency times from 10 to 20 hours for one or both agents of the combination of the invention are observed.

Many strategies can be pursued to obtain controlled and/or extended release in which the rate of release outweighs the rate of metabolism of the therapeutic compound. For example, controlled release can be obtained by the appropriate selection of formulation parameters and ingredients (e.g., appropriate controlled release compositions and coatings). Examples include single or multiple unit tablet or capsule compositions, oil solutions, suspensions, emulsions, microcapsules, microspheres, nanoparticles, patches, and liposomes. The release mechanism can be controlled such that the tetra-substituted pyrimidopyrimidine and/or companion compounds (e.g., antihistamine, corticosteroid, rolipram, ibudilast, tricyclic and tetracyclic antidepressants, SSRI, non-steroidal anti-inflammatory drugs, non-steroidal immunophilin-dependent immunosuppressants and analogs thereof, as described herein) are released at period intervals, the release could be simultaneous, or a delayed release of one of the agents of the combination can be affected, when the early release of one particular agent is preferred over the other.

When combined with additional compounds such as an NSAID, COX-2 inhibitor, biologic, small molecule immunomodulator, DMARD, xanthine, anticholinergic compound, beta receptor agonist, bronchodilator, non-steroidal immunophilin-dependent immunomodulators, vitamin D analog, psoralen, retinoid, and 5-amino salicylic acid, the release mechanism of additional compounds can also be controlled like that of the tetra-substituted pyrimidopyrimidine and/or companion compounds (e.g., antihistamine, corticosteroid, rolipram, ibudilast, tricyclic and tetracyclic antidepressants, SSRI, non-steroidal immunophilin-dependent immunosuppressants and analogs thereof, as described herein) and are similarly released at period intervals, the release could be simultaneous, or a delayed release of one of the agents of the combination can be affected, when the early release of one particular agent is preferred over the other.

When it is required to obtain a constant level of tetra-substituted pyrimidopyrimidine in the blood, it will be advantageous to start with tetra-substituted pyrimidopyrimidine in the form of pellets that enable this active substance to be released at a steady rate. For example, dipyridamole pellets can be processed together with the acetylsalicylic acid to form corresponding drug preparations. If it is intended that the acetylsalicylic acid should be released first, the dipyridamole-pellets may be coated with a coating which delays the release of this active substance and the cores containing the acetyl-salicylic acid coated with a coating that is soluble in gastric juices. In the case of dipyridamole pellets with a controlled release of the active substance it is particularly advantageous to use pellets prepared according to the instructions given in U.S. Pat. No. 4,367,217.

Controlled and/or extended release formulations may include a degradable or nondegradable polymer, hydrogel, organogel, or other physical construct that modifies the bioabsorption, half-life or biodegradation of the agent. The controlled and/or extended release formulation can be a material that is painted or otherwise applied onto the afflicted site, either internally or externally. In one example, the invention provides a biodegradable bolus or implant that is surgically inserted at or near a site of interest (for example, proximal to an arthritic joint). In another example, the controlled release formulation implant can be inserted into an organ, such as in the lower intestine for the treatment inflammatory bowel disease.

Hydrogels can be used in controlled release formulations for any one of the combinations of this invention. Such polymers are formed from macromers with a polymerizable, non-degradable, region that is separated by at least one degradable region. For example, the water soluble, non-degradable, region can form the central core of the macromer and have at least two degradable regions which are attached to the core, such that upon degradation, the non-degradable regions (in particular a polymerized gel) are separated, as described in U.S. Pat. No. 5,626,863. Hydrogels can include acrylates, which can be readily polymerized by several initiating systems such as eosin dye, ultraviolet or visible light. Hydrogels can also include polyethylene glycols (PEGs), which are highly hydrophilic and biocompatible. Hydrogels can also include oligoglycolic acid, which is a poly($\alpha$-hydroxy acid) that can be readily degraded by hydrolysis of the ester linkage into glycolic acid, a nontoxic metabolite. Other chain extensions can include polylactic acid, polycaprolactone, polyorthoesters, polyanhydrides or polypeptides. The entire network can be gelled into a biodegradable network that can be used to entrap and homogeneously disperse various combinations of the invention for delivery at a controlled rate.

Chitosan and mixtures of chitosan with carboxymethylcellulose sodium (CMC—Na) have been used as vehicles for the sustained release of drugs, as described by Inouye et al., Drug Design and Delivery 1: 297-305, 1987. Mixtures of these compounds and agents of the any one of the combinations described above, when compressed under 200 kg/cm$^2$, form a tablet from which the active agent is slowly released upon administration to a subject. The release profile can be changed by varying the ratios of chitosan, CMC—Na, and active agent(s). The tablets can also contain other additives, including lactose, CaHPO$_4$ dihydrate, sucrose, crystalline cellulose, or croscarmellose sodium. Several examples are given in Table 6.

TABLE 6

| Materials | Tablet components (mg) | | | | | | | | | | | |
|---|---|---|---|---|---|---|---|---|---|---|---|---|
| Active agent | 20 | 20 | 20 | 20 | 20 | 20 | 20 | 20 | 20 | 20 | 20 | 20 |
| Chitosan | 10 | 10 | 10 | 10 | 10 | 20 | 3.3 | 20 | 3.3 | 70 | 40 | 28 |
| Lactose | | 110 | | | | 220 | 36.7 | | | | | |
| CMC-Na | 60 | 60 | 60 | 60 | 60 | 120 | 20 | 120 | 20 | | 30 | 42 |
| CaHPO$_4$*2H$_2$O | | | 110 | | | | | 220 | 36.7 | 110 | 110 | 110 |
| Sucrose | 110 | | | | | | | | | | | |
| Crystalline Cellulose | | | | | 110 | | | | | | | |
| Croscarmellose Na | | | | 110 | | | | | | | | |

Baichwal, in U.S. Pat. No. 6,245,356, describes a sustained release oral solid dosage forms that includes agglomerated particles of a therapeutically active medicament in amorphous form, a gelling agent, an ionizable gel strength enhancing agent and an inert diluent. The gelling agent can be a mixture of a xanthan gum and a locust bean gum capable of cross-linking with the xanthan gum when the gums are exposed to an environmental fluid. Preferably, the ionizable gel enhancing agent acts to enhance the strength of cross-linking between the xanthan gum and the locust bean gum and thereby prolonging the release of the medicament component of the formulation. In addition to xanthan gum and locust bean gum, acceptable gelling agents that may also be used include those gelling agents well known in the art. Examples include naturally occurring or modified naturally occurring gums such as alginates, carrageenan, pectin, guar gum, modified starch, hydroxypropylmethylcellulose, methylcellulose, and other cellulosic materials or polymers, such as, for example, sodium carboxymethylcellulose and hydroxypropyl cellulose, and mixtures of the foregoing.

In another formulation useful for the combinations of the invention, Baichwal and Staniforth in U.S. Pat. No. 5,135,757 describe a free-flowing slow release granulation for use as a pharmaceutical excipient that includes from about 20 to about 70 percent or more by weight of a hydrophilic material that includes a heteropolysaccharide (such as, for example, xanthan gum or a derivative thereof) and a polysaccharide material capable of cross-linking the heteropolysaccharide (such as, for example, galactomannans, and most preferably locust bean gum) in the presence of aqueous solutions, and from about 30 to about 80 percent by weight of an inert pharmaceutical filler (such as, for example, lactose, dextrose, sucrose, sorbitol, xylitol, fructose or mixtures thereof). After mixing the excipient with a combination, or combination agent, of the invention, the mixture is directly compressed into solid dosage forms such as tablets. The tablets thus formed slowly release the medicament when ingested and exposed to gastric fluids. By varying the amount of excipient relative to the medicament, a slow release profile can be attained.

In another formulation useful for the combinations of the invention, Shell, in U.S. Pat. No. 5,007,790, describes sustained-release oral drug-dosage forms that release a drug in solution at a rate controlled by the solubility of the drug. The dosage form comprises a tablet or capsule that includes a plurality of particles of a dispersion of a limited solubility drug (such as, for example, prednisolone, paroxetine, or any other agent of anyone or all of the combination of the present invention) in a hydrophilic, water-swellable, crosslinked polymer that maintains its physical integrity over the dosing lifetime but thereafter rapidly dissolves. Once ingested, the particles swell to promote gastric retention and permit the gastric fluid to penetrate the particles, dissolve drug and leach it from the particles, assuring that drug reaches the stomach in the solution state which is less injurious to the stomach than solid-state drug. The programmed eventual dissolution of the polymer depends upon the nature of the polymer and the degree of crosslinking. The polymer is nonfibrillar and substantially water soluble in its uncrosslinked state, and the degree of crosslinking is sufficient to enable the polymer to remain insoluble for the desired time period, normally at least from about 4 hours to 8 hours up to 12 hours, with the choice depending upon the drug incorporated and the medical treatment involved. Examples of suitable crosslinked polymers that may be used in the invention are gelatin, albumin, sodium alginate, carboxymethyl cellulose, polyvinyl alcohol, and chitin. Depending upon the polymer, crosslinking may be achieved by thermal or radiation treatment or through the use of crosslinking agents such as aldehydes, polyamino acids, metal ions and the like.

Silicone microspheres for pH-controlled gastrointestinal drug delivery that are useful in the formulation of anyone or all of the combinations of the invention have been described by Carelli et al., Int. J. Pharmaceutics 179: 73-83, 1999. The microspheres so described are pH-sensitive semi-interpenetrating polymer hydrogels made of varying proportions of poly(methacrylic acid-co-methylmethacrylate) (Eudragit L100 or Eudragit S100) and crosslinked polyethylene glycol 8000 that are encapsulated into silicone microspheres in the 500 to 1000 μm size range.

Slow-release formulations may include a coating that is not readily water-soluble but is slowly attacked and removed by water, or through which water can slowly permeate. Thus, for example, a combination of the invention can be spray-coated with a solution of a binder under continuously fluidizing conditions, such as describe by Kitamori et al., U.S. Pat. No. 4,036,948. Water-soluble binders include pregelatinized starch (e.g., pregelatinized corn starch, pregelatinized white potato starch), pregelatinized modified starch, water-soluble celluloses (e.g. hydroxypropyl-cellulose, hydroxymethyl-cellulose, hydroxypropylmethyl-cellulose, carboxymethyl-cellulose), polyvinylpyrrolidone, polyvinyl alcohol, dextrin, gum arabicum and gelatin, and organic solvent-soluble binders, such as cellulose derivatives (e.g., cellulose acetate phthalate, hydroxypropylmethyl-cellulose phthalate, ethylcellulose).

Combinations of the invention, or a component thereof, with sustained release properties can also be formulated by spray drying techniques. In one example, as described by Espositio et al., Pharm. Dev. Technol. 5: 267-78, 2000, prednisolone was encapsulated in methyacrylate microparticles (Eudragit RS) using a Mini Spray Dryer, model 190 (Buchi, Laboratorium Technik AG, Flawil, Germany). Optimal conditions for microparticle formation were found to be a feed (pump) rate of 0.5 mL/min of a solution containing 50 mg prednisolone in 10 mL of acetonitrile, a flow rate of nebulized air of 600 L/hr, dry air temperature heating at 80° C., and a flow rate of aspirated drying air of 28 $m^3$/hr.

Yet another form of sustained release combinations can be prepared by microencapsulation of combination agent particles in membranes which act as microdialysis cells. In such a formulation, gastric fluid permeates the microcapsule walls and swells the microcapsule, allowing the active agent(s) to dialyze out (see, for example, Tsuei et al., U.S. Pat. No. 5,589,194). One commercially available sustained-release system of this kind consists of microcapsules having membranes of acacia gum/gelatine/ethyl alcohol. This product is available from Eurand Limited (France) under the trade name Diffucaps™. Microcapsules so formulated might be carried in a conventional gelatine capsule or tabletted.

Extended- and/or controlled-release formulations of combinations of this invention, such as, both tetra-substituted pyrimidopyrimidine and antihistamine or SSRI are known.

Other extended-release formulation examples are described in U.S. Pat. No. 5,422,123. Thus, a system for the controlled release of an active substance which is an tetra-substituted pyrimidopyrimidine such as dipyridamole, comprising (a) a deposit-core comprising an effective amount of the active substance and having defined geometric form, and (b) a support-platform applied to the deposit-core, wherein the deposit-core contains at least the active substance, and at least one member selected from the group consisting of (1) a polymeric material which swells on contact with water or aqueous liquids and a gellable polymeric material wherein the ratio of the swellable polymeric material to the gellable polymeric material is in the range 1:9 to 9:1, and (2) a single polymeric material having both swelling and gelling properties, and wherein the support-platform is an elastic support, applied to said deposit-core so that it partially covers the surface of the deposit-core and follows changes due to hydration of the deposit-core and is slowly soluble and/or slowly gellable in aqueous fluids. The support-platform may comprise polymers such as hydroxypropylmethylcellulose, plasticizers such as a glyceride, binders such as polyvinylpyrrolidone, hydrophilic agents such as lactose and silica, and/or hydrophobic agents such as magnesium stearate and glycerides. The polymer(s) typically make up 30 to 90% by weight of the support-platform, for example about 35 to 40%. Plasticizer may make up at least 2% by weight of the support-platform, for example about 15 to 20%. Binder(s), hydrophilic agent(s) and hydrophobic agent(s) typically total up to about 50% by weight of the support-platform, for example about 40 to 50%.

A controlled-release formulation of budesonide (3 mg capsules) for the treatment of inflammatory bowel disease is available from AstraZeneca (sold as Entocort™). A sustained-release formulation useful for corticosteroids is also described in U.S. Pat. No. 5,792,476, where the formulation includes 2.5-7 mg of a glucocorticoid as active substance with a regulated sustained-release such that at least 90% by weight of the glucocorticoid is released during a period of about 40-80 min, starting about 1-3 h after the entry of said glucocorticoid into the small intestine of the patient. To make these low dose levels of active substance possible, the active substance, i.e. the glucocorticoid, such as prednisolone or prednisone, is micronised, suitably mixed with known diluents, such as starch and lactose, and granulated with PVP (polyvinylpyrrolidone). Further, the granulate is laminated with a sustained release inner layer resistant to a pH of 6.8 and a sustained release outer layer resistant to a pH of 1.0. The inner layer is made of Eudragit®RL (copolymer of acrylic and methacrylic esters with a low content of quaternary ammonium groups) and the outer layer is made of Eudragit®L (anionic polymer synthesized from methacrylic acid and methacrylic acid methyl ester).

A bilayer tablet can be formulated for any one of the combinations described herein in which different custom granulations are made for each agent of the combination and the two agents are compressed on a bi-layer press to form a single tablet. For example, 12.5 mg, 25 mg, 37.5 mg, or 50 mg of paroxetine, formulated for a controlled release that results in a paroxetine $t_{1/2}$ of 15 to 20 hours may be combined in the same tablet with 3 mg of predinisolone, which is formulated such that the $t_{1/2}$ approximates that of paroxetine. Examples of paroxetine extended-release formulations, including those used in bilayer tablets, can be found in U.S. Pat. No.6,548, 084. Cyclodextrins are cyclic polysaccharides containing naturally occurring D(+)-glucopyranose units in an α-(1,4) linkage. Alpha-, beta- and gamma-cyclodextrins, which contain, respectively, six, seven or eight glucopyranose units, are most commonly used and suitable examples are described in WO91/11172, WO94/02518 and WO98/55148. Structurally, the cyclic nature of a cyclodextrin forms a torus or donut-like shape having an inner apolar or hydrophobic cavity, the secondary hydroxyl groups situated on one side of the cyclodextrin torus and the primary hydroxyl groups situated on the other. The side on which the secondary hydroxyl groups are located has a wider diameter than the side on which the primary hydroxyl groups are located. The hydrophobic nature of the cyclodextrin inner cavity allows for the inclusion of a variety of compounds. (Comprehensive Supramolecular Chemistry, Volume 3, J. L. Atwood et al., eds., Pergamon Press (1996); Cserhati, Analytical Biochemistry 225: 328-32, 1995; Husain et al., Applied Spectroscopy 46: 652-8, 1992. Cyclodextrins have been used as a delivery vehicle of various therapeutic compounds by forming inclusion complexes with various drugs that can fit into the hydrophobic cavity of the cyclodextrin or by forming non-covalent association complexes with other biologically active molecules. U.S. Pat. No. 4,727,064 describes pharmaceutical preparations consisting of a drug with substantially low water solubility and an amorphous, water-soluble cyclodextrin-based mixture in which the drug forms an inclusion complex with the cyclodextrins of the mixture.

Formation of a drug-cyclodextrin complex can modify the drug's solubility, dissolution rate, bioavailability, and/or stability properties.

Sulfobutylether-β-cyclodextrin (SBE-β-CD, commercially available from CyDex, Inc, Overland Park, Kans., and sold as CAPTISOL®) can also be used as an aid in the preparation of sustained-release formulations of agents of the combinations of the present invention. For example, a sustained-release tablet has been prepared that includes prednisolone and SBE-β-CD compressed in a hydroxypropyl methylcellulose matrix (see Rao et al., J. Pharm. Sci. 90: 807-16, 2001). In another example of the use of various cyclodextrins, EP 1109806 B1 describes cyclodextrin complexes of paroxetine, where α-, γ-, or β-cyclodextrins [including eptakis(2-6-di-O-methyl)-β-cyclodextrin, (2,3,6-tri-O-methyl)-β-cyclodextrin, monosuccinyl eptakis(2,6-di-O-methyl)-β-cyclodextrin, or 2-hydroxypropyl-β-cyclodextrin] in anhydrous or hydrated form formed complex ratios of agent to cyclodextrin of from 1:0.25 to 1:20 can be obtained.

Polymeric cyclodextrins have also been prepared, as described in U.S. patent application Ser. Nos. 10/021,294 and 10/021,312. The cyclodextrin polymers so formed can be useful for formulating agents of the combinations of the present invention. These multifunctional polymeric cyclodextrins are commercially available from Insert Therapeutics, Inc., Pasadena, Calif.

As an alternative to direct complexation with agents, cyclodextrins may be used as an auxiliary additive, e.g. as a carrier, diluent or solubiliser. Formulations that include cyclodextrins and other agents of the combinations of the present invention can be prepared by methods similar to the preparations of the cyclodextrin formulations described herein.

Liposomal Formulations

One or both components of any one of the combinations of the invention, or mixtures of the two components together, can be incorporated into liposomal carriers for administration. The liposomal carriers are composed of three general types of vesicle-forming lipid components. The first includes vesicle-forming lipids that form the bulk of the vesicle structure in the liposome. Generally, these vesicle-forming lipids include any amphipathic lipids having hydrophobic and polar head group moieties, and which (a) can form spontaneously into bilayer vesicles in water, as exemplified by phospholipids, or (b) are stably incorporated into lipid bilayers, with its hydrophobic moiety in contact with the interior, hydrophobic region of the bilayer membrane, and its polar head group moiety oriented toward the exterior, polar surface of the membrane.

The vesicle-forming lipids of this type are preferably ones having two hydrocarbon chains, typically acyl chains, and a polar head group. Included in this class are the phospholipids, such as phosphatidylcholine (PC), PE, phosphatidic acid (PA), phosphatidylinositol (PI), and sphingomyelin (SM), where the two hydrocarbon chains are typically between about 14-22 carbon atoms in length, and have varying degrees of unsaturation. The above-described lipids and phospholipids whose acyl chains have a variety of degrees of saturation can be obtained commercially, or prepared according to published methods. Other lipids that can be included in the invention are glycolipids and sterols, such as cholesterol.

The second general component includes a vesicle-forming lipid that is derivatized with a polymer chain which will form the polymer layer in the composition. The vesicle-forming lipids thta can be used as the second general vesicle-forming lipid component are any of those described for the first general vesicle-forming lipid component. Vesicle forming lipids with diacyl chains, such as phospholipids, are preferred. One exemplary phospholipid is phosphatidylethanolamine (PE), which provides a reactive amino group that is convenient for coupling to the activated polymers. An exemplary PE is distearyl PE (DSPE).

The preferred polymer in the derivatized lipid, is polyethyleneglycol (PEG), preferably a PEG chain having a molecular weight between 1,000-15,000 daltons, more preferably between 2,000 and 10,000 daltons, most preferably between 2,000 and 5,000 daltons. Other hydrophilic polymers that may be suitable include polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses, such as hydroxymethylcellulose or hydroxyethylcellulose.

Additionally, block copolymers or random copolymers of these polymers, particularly including PEG segments, may be suitable. Methods for preparing lipids derivatized with hydrophilic polymers, such as PEG, are well known e.g., as described in U.S. Pat. No. 5,013,556.

A third general vesicle-forming lipid component, which is optional, is a lipid anchor by which a targeting moiety is anchored to the liposome, through a polymer chain in the anchor. Additionally, the targeting group is positioned at the distal end of the polymer chain in such a way so that the biological activity of the targeting moiety is not lost. The lipid anchor has a hydrophobic moiety which serves to anchor the lipid in the outer layer of the liposome bilayer surface, a polar head group to which the interior end of the polymer is covalently attached, and a free (exterior) polymer end which is or can be activated for covalent coupling to the targeting moiety. Methods for preparing lipid anchor molecules of these types are described below.

The lipids components used in forming the liposomes are preferably present in a molar ratio of about 70-90 percent vesicle forming lipids, 1-25 percent polymer derivatized lipid, and 0.1-5 percent lipid anchor. One exemplary formulation includes 50-70 mole percent underivatized PE, 20-40 mole percent cholesterol, 0.1-1 mole percent of a PE-PEG (3500) polymer with a chemically reactive group at its free end for coupling to a targeting moiety, 5-10 mole percent PE derivatized with PEG 3500 polymer chains, and 1 mole percent alpha-tocopherol.

The liposomes are preferably prepared to have substantially homogeneous sizes in a selected size range, typically between about 0.03 to 0.5 microns. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less.

The liposomal formulations of the present invention include at least one surface-active agent. Suitable surface-active agents useful for the formulation of the various combinations described herein include compounds belonging to the following classes: polyethoxylated fatty acids, PEG-fatty acid diesters, PEG-fatty acid mono-ester and di-ester mixtures, polyethylene glycol glycerol fatty acid esters, alcohol-oil transesterification products, polyglycerized fatty acids, propylene glycol fatty acid esters, mixtures of propylene glycol esters and glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, and ionic surfactants. Commercially available examples for each class of excipient are provided below.

Polyethoxylated fatty acids may be used as excipients for the formulation of any one of the combinations described herein. Examples of commercially available polyethoxylated fatty acid monoester surfactants include: PEG 4-100 monolaurate (Crodet L series, Croda), PEG 4-100 monooleate (Crodet O series, Croda), PEG 4-100 monostearate (Crodet S series, Croda, and Myrj Series, Atlas/ICI), PEG 400 distearate (Cithrol 4DS series, Croda), PEG 100, 200, or 300 monolaurate (Cithrol ML series, Croda), PEG 100, 200, or 300 monooleate (Cithrol MO series, Croda), PEG 400 dioleate (Cithrol 4DO series, Croda), PEG 400-1000 monostearate (Cithrol MS series, Croda), PEG-1 stearate (Nikkol MYS-1EX, Nikko, and Coster K1, Condea), PEG-2 stearate (Nikkol MYS-2, Nikko), PEG-2 oleate (Nikkol MYO-2, Nikko), PEG-4 laurate (Mapeg® 200 ML, PPG), PEG-4 oleate (Mapeg® 200 MO, PPG), PEG-4 stearate (Kessco® PEG 200 MS, Stepan), PEG-5 stearate (Nikkol TMGS-5, Nikko), PEG-5 oleate (Nikkol TMGO-5, Nikko), PEG-6 oleate (Algon OL 60, Auschem SpA), PEG-7 oleate (Algon OL 70, Auschem SpA), PEG-6 laurate (Kessco® PEG300 ML, Stepan), PEG-7 laurate (Lauridac 7, Condea), PEG-6 stearate (Kessco® PEG300 MS, Stepan), PEG-8 laurate (Mapeg® 400 ML, PPG), PEG-8 oleate (Mapeg® 400 MO, PPG), PEG-8 stearate (Mapeg® 400 MS, PPG), PEG-9 oleate (Emulgante A9, Condea), PEG-9 stearate (Cremophor S9, BASF), PEG-10 laurate (Nikkol MYL-10, Nikko), PEG-10 oleate (Nikkol MYO-10, Nikko), PEG-12 stearate (Nikkol MYS-10, Nikko), PEG-12 laurate (Kessco® PEG 600 ML, Stepan), PEG-12 oleate (Kessco® PEG 600 MO, Stepan), PEG-12 ricinoleate (CAS # 9004-97-1), PEG-12 stearate (Mapeg® 600 MS, PPG), PEG-15 stearate (Nikkol TMGS-15, Nikko), PEG-15 oleate (Nikkol TMGO-15, Nikko), PEG-20 laurate (Kessco® PEG 1000 ML, Stepan), PEG-20 oleate (Kessco® PEG 1000 MO, Stepan), PEG-20 stearate (Mapeg® 1000 MS, PPG), PEG-25 stearate (Nikkol MYS-25, Nikko), PEG-32 laurate (Kessco® PEG 1540 ML, Stepan), PEG-32 oleate (Kessco® PEG 1540 MO, Stepan), PEG-32 stearate (Kessco® PEG 1540 MS, Stepan), PEG-30 stearate (Myrj 51), PEG-40 laurate (Crodet L40, Croda), PEG-40 oleate (Crodet O40, Croda), PEG-40 stearate (Emerest® 2715, Henkel), PEG-45 stearate (Nikkol MYS-45, Nikko), PEG-50 stearate (Myrj 53), PEG-55 stearate (Nikkol MYS-55, Nikko), PEG-100 oleate (Crodet O-100, Croda), PEG- 100 stearate (Ariacel 165, ICI), PEG-200 oleate (Albunol 200 MO, Taiwan Surf.), PEG-400 oleate (LACTOMUL, Henkel), and PEG-600 oleate (Albunol 600 MO, Taiwan Surf.). Formulations of one or both components of anyone or all of the combinations according to the invention may include one or more of the polyethoxylated fatty acids above.

Polyethylene glycol fatty acid diesters may also be used as excipients for anyone or all of the combinations described herein. Examples of commercially available polyethylene glycol fatty acid diesters include: PEG-4 dilaurate (Mapeg® 200 DL, PPG), PEG-4 dioleate (Mapeg® 200 DO, PPG), PEG-4 distearate (Kessco® 200 DS, Stepan), PEG-6 dilaurate (Kessco® PEG 300 DL, Stepan), PEG-6 dioleate (Kessco® PEG 300 DO, Stepan), PEG-6 distearate (Kessco® PEG 300 DS, Stepan), PEG-8 dilaurate (Mapeg® 400 DL, PPG), PEG-8 dioleate (Mapeg® 400 DO, PPG), PEG-8 distearate (Mapeg® 400 DS, PPG), PEG-10 dipalmitate (Poly-aldo 2PKFG), PEG-12 dilaurate (Kessco® PEG 600 DL, Stepan), PEG-12 distearate (Kessco® PEG 600 DS, Stepan), PEG-12 dioleate (Mapeg® 600 DO, PPG), PEG-20 dilaurate (Kessco® PEG 1000 DL, Stepan), PEG-20 dioleate (Kessco® PEG 1000 DO, Stepan), PEG-20 distearate (Kessco® PEG 1000 DS, Stepan), PEG-32 dilaurate (Kessco® PEG 1540 DL, Stepan), PEG-32 dioleate (Kessco® PEG 1540 DO, Stepan), PEG-32 distearate (Kessco® PEG 1540 DS, Stepan), PEG-400 dioleate (Cithrol 4DO series, Croda), and PEG-400 distearate Cithrol 4DS series, Croda). Formulations of anyone of the combinations according to the invention may include one or more of the polyethylene glycol fatty acid diesters above.

PEG-fatty acid mono- and di-ester mixtures may be used as excipients for the formulation of anyone or all of the combinations described herein. Examples of commercially available PEG-fatty acid mono- and di-ester mixtures include: PEG 4-150 mono, dilaurate (Kessco® PEG 200-6000 mono, Dilaurate, Stepan), PEG 4-150 mono, dioleate (Kessco® PEG 200-6000 mono, Dioleate, Stepan), and PEG 4-150 mono, distearate (Kessco® 200-6000 mono, Distearate, Stepan). Formulations of the anyone or all of the combinations according to the invention may include one or more of the PEG-fatty acid mono- and di-ester mixtures above.

In addition, polyethylene glycol glycerol fatty acid esters may be used as excipients for the formulation of anyone or all of the combinations described herein. Examples of commercially available polyethylene glycol glycerol fatty acid esters include: PEG-20 glyceryl laurate (Tagat® L, Goldschmidt), PEG-30 glyceryl laurate (Tagat® L2, Goldschmidt), PEG-15 glyceryl laurate (Glycerox L series, Croda), PEG-40 glyceryl laurate (Glycerox L series, Croda), PEG-20 glyceryl stearate (Capmul® EMG, ABITEC), and Aldo® MS-20 KFG, Lonza), PEG-20 glyceryl oleate (Tagat® O, Goldschmidt), and PEG-30 glyceryl oleate (Tagat® O2, Goldschmidt). Formulations of anyone or all of the combinations according to the invention may include one or more of the polyethylene glycol glycerol fatty acid esters above.

Alcohol-oil transesterification products may also be used as excipients for the formulation of anyone or all of the combinations described herein. Examples of commercially available alcohol-oil transesterification products include: PEG-3 castor oil (Nikkol CO-3, Nikko), PEG-5, 9, and 16 castor oil (ACCONON CA series, ABITEC), PEG-20 castor oil, (Emalex C-20, Nihon Emulsion), PEG-23 castor oil (Emulgante EL23), PEG-30 castor oil (Incrocas 30, Croda), PEG-35 castor oil (Incrocas-35, Croda), PEG-38 castor oil (Emulgante EL 65, Condea), PEG-40 castor oil (Emalex C-40, Nihon Emulsion), PEG-50 castor oil (Emalex C-50, Nihon Emulsion), PEG-56 castor oil (Eumulgin® PRT 56, Pulcra SA), PEG-60 castor oil (Nikkol CO-60TX, Nikko), PEG-100 castor oil, PEG-200 castor oil (Eumulgin® PRT 200, Pulcra SA), PEG-5 hydrogenated castor oil (Nikkol HCO-5, Nikko), PEG-7 hydrogenated castor oil (Cremophor WO7, BASF), PEG-10 hydrogenated castor oil (Nikkol HCO-10, Nikko), PEG-20 hydrogenated castor oil (Nikkol HCO-20, Nikko), PEG-25 hydrogenated castor oil (Simulsol® 1292, Seppic), PEG-30 hydrogenated castor oil (Nikkol HCO-30, Nikko), PEG-40 hydrogenated castor oil (Cremophor RH 40, BASF), PEG-45 hydrogenated castor oil (Cerex ELS 450, Auschem Spa), PEG-50 hydrogenated castor oil (Emalex HC-50, Nihon Emulsion), PEG-60 hydrogenated castor oil (Nikkol HCO-60, Nikko), PEG-80 hydrogenated castor oil (Nikkol HCO-80, Nikko), PEG-100 hydrogenated castor oil (Nikkol HCO-100, Nikko), PEG-6 corn oil (Labrafil® M 2125 CS, Gattefosse), PEG-6 almond oil (Labrafil® M 1966 CS, Gattefosse), PEG-6 apricot kernel oil (Labrafil® M 1944 CS, Gattefosse), PEG-6 olive oil (Labrafil® M 1980 CS, Gattefosse), PEG-6 peanut oil (Labrafil® M 1969 CS, Gattefosse), PEG-6 hydrogenated palm kernel oil (Labrafil® M 2130 BS, Gattefosse), PEG-6 palm kernel oil (Labrafil® M 2130 CS, Gattefosse), PEG-6 triolein (Labrafil® M 2735 CS, Gattefosse), PEG-8 corn oil (Labrafil® WL 2609 BS, Gattefosse), PEG-20 corn glycerides (Crovol M40, Croda), PEG-20 almond glycerides (Crovol A40, Croda), PEG-25 trioleate (TAGAT® TO, Goldschmidt), PEG-40 palm kernel oil (Crovol PK-70), PEG-60 corn glycerides (Crovol M70, Croda), PEG-60 almond glycerides (Crovol A70, Croda), PEG-4 caprylic/capric triglyceride (Labrafac® Hydro, Gattefosse), PEG-8 caprylic/capric glycerides (Labrasol, Gattefosse), PEG-6 caprylic/capric glycerides (SOFTIGEN®767, Huls), lauroyl macrogol-32 glyceride (GELUCIRE 44/14, Gattefosse), stearoyl macrogol glyceride (GELUCIRE 50/13, Gattefosse), mono, di, tri, tetra esters of vegetable oils and sorbitol (SorbitoGlyceride, Gattefosse), pentaerythrityl tetraisostearate (Crodamol PTIS, Croda), pentaerythrityl distearate (Albunol DS, Taiwan Surf.), pentaerythrityl tetraoleate (Liponate PO-4, Lipo Chem.), pentaerythrityl tetrastearate (Liponate PS-4, Lipo Chem.), pentaerythrityl tetracaprylate tetracaprate (Liponate PE-810, Lipo Chem.), and pentaerythrityl tetraoctanoate (Nikkol Pentarate 408, Nikko). Also included as oils in this category of surfactants are oil-soluble vitamins, such as vitamins A, D, E, K, etc. Thus, derivatives of these vitamins, such as tocopheryl PEG-1000 succinate (TPGS, available from Eastman), are also suitable surfactants. Formulations of anyone or all of the combinations according to the invention may include one or more of the alcohol-oil transesterification products above.

Polyglycerized fatty acids may also be used as excipients for the formulation of anyone or all of the combinations described herein. Examples of commercially available polyglycerized fatty acids include: polyglyceryl-2 stearate (Nikkol DGMS, Nikko), polyglyceryl-2 oleate (Nikkol DGMO, Nikko), polyglyceryl-2 isostearate (Nikkol DGMIS, Nikko), polyglyceryl-3 oleate (Caprol® 3GO, ABITEC), polyglyceryl-4 oleate (Nikkol Tetraglyn 1-O, Nikko), polyglyceryl-4 stearate (Nikkol Tetraglyn 1-S, Nikko), polyglyceryl-6 oleate (Drewpol 6-1-O, Stepan), polyglyceryl-10 laurate (Nikkol Decaglyn 1-L, Nikko), polyglyceryl-10 oleate (Nikkol Decaglyn 1-O, Nikko), polyglyceryl-10 stearate (Nikkol Decaglyn 1-S, Nikko), polyglyceryl-6 ricinoleate (Nikkol Hexaglyn PR-15, Nikko), polyglyceryl-10 linoleate (Nikkol Decaglyn 1-LN, Nikko), polyglyceryl-6 pentaoleate (Nikkol Hexaglyn 5-O, Nikko), polyglyceryl-3 dioleate (Cremophor GO32, BASF), polyglyceryl-3 distearate (Cremophor GS32, BASF), polyglyceryl-4 pentaoleate (Nikkol Tetraglyn 5-O, Nikko), polyglyceryl-6 dioleate (Caprol® 6G20, ABITEC), polyglyceryl-2 dioleate (Nikkol DGDO, Nikko), polyglyceryl-10 trioleate (Nikkol Decaglyn 3-O, Nikko), polyglyceryl-10 pentaoleate (Nikkol Decaglyn 5-O, Nikko), polyglyceryl-10 septaoleate (Nikkol Decaglyn 7-O, Nikko), polyglyceryl-10 tetraoleate (Caprol® 10G40, ABITEC), polyglyceryl-10 decaisostearate (Nikkol Decaglyn 10-IS, Nikko), polyglyceryl-101 decaoleate (Drewpol 10-10-O, Stepan), polyglyceryl-10 mono, dioleate (Caprol® PGE 860, ABITEC), and polyglyceryl polyricinoleate (Polymuls, Henkel). Formulations of anyone or all of the combinations according to the invention may include one or more of the polyglycerized fatty acids above.

In addition, propylene glycol fatty acid esters may be used as excipients for the formulation of the tetra-substituted pyrimidopyrimidine anyone or all of the combinations described herein. Examples of commercially available propylene glycol fatty acid esters include: propylene glycol monocaprylate (Capryol 90, Gattefosse), propylene glycol monolaurate (Lauroglycol 90, Gattefosse), propylene glycol oleate (Lutrol OP2000, BASF), propylene glycol myristate (Mirpyl), propylene glycol monostearate (LIPO PGMS, Lipo Chem.), propylene glycol hydroxystearate, propylene glycol ricinoleate (PROPYMULS, Henkel), propylene glycol isostearate, propylene glycol monooleate (Myverol P-O6, Eastman), propylene glycol dicaprylate dicaprate (Captex® 200, ABITEC), propylene glycol dioctanoate (Captex® 800, ABITEC), propylene glycol caprylate caprate (LABRAFAC PG, Gattefosse), propylene glycol dilaurate, propylene glycol distearate (Kessco® PGDS, Stepan), propylene glycol dicaprylate (Nikkol Sefsol 228, Nikko), and propylene glycol dicaprate (Nikkol PDD, Nikko). Formulations of anyone or all of the combinations to the invention may include one or more of the propylene glycol fatty acid esters above.

Mixtures of propylene glycol esters and glycerol esters may also be used as excipients for the formulation of anyone or all of the combinations described herein. One preferred mixture is composed of the oleic acid esters of propylene glycol and glycerol (Arlacel 186). Examples of these surfactants include: oleic (ATMOS 300, ARLACEL 186, ICI), and stearic (ATMOS 150). Formulations of anyone or all of the combinations according to the invention may include one or more of the mixtures of propylene glycol esters and glycerol esters above.

Further, mono- and diglycerides may be used as excipients for the formulation of anyone or all of the combinations described herein. Examples of commercially available mono- and diglycerides include: monopalmitolein (C16:1) (Larodan), monoelaidin (C18:1) (Larodan), monocaproin (C6) (Larodan), monocaprylin (Larodan), monocaprin (Larodan), monolaurin (Larodan), glyceryl monomyristate (C14) (Nikkol MGM, Nikko), glyceryl monooleate (C18:1) (PECEOL, Gattefosse), glyceryl monooleate (Myverol, Eastman), glycerol monooleate/linoleate (OLICINE, Gattefosse), glycerol monolinoleate (Maisine, Gattefosse), glyceryl ricinoleate (Softigen® 701, Huls), glyceryl monolaurate (ALDO® MLD, Lonza), glycerol monopalmitate (Emalex GMS-P, Nihon), glycerol monostearate (Capmul® GMS, ABITEC), glyceryl mono- and dioleate (Capmul® GMO-K, ABITEC), glyceryl palmitic/stearic (CUTINA MD-A, ESTAGEL-G18), glyceryl acetate (Lamegin® EE, Grunau GmbH), glyceryl laurate (Imwitor® 312, Huls), glyceryl citrate/lactate/oleate/ linoleate (Imwitor® 375, Huls), glyceryl caprylate (Imwitor® 308, Huls), glyceryl caprylate/caprate (Capmul® MCM, ABITEC), caprylic acid mono- and diglycerides (Imwitor® 988, Huls), caprylic/capric glycerides (Imwitor® 742, Huls), Mono- and diacetylated monoglycerides (Myvacet® 9-45, Eastman), glyceryl monostearate (Aldo® MS, Arlacel 129, ICI), lactic acid esters of mono and diglycerides (LAMEGIN GLP, Henkel), dicaproin (C6) (Larodan), dicaprin (C10) (Larodan), dioctanoin (C8) (Larodan), dimyristin (C14) (Larodan), dipalmitin (C16) (Larodan), distearin (Larodan), glyceryl dilaurate (C12) (Capmul® GDL, ABITEC), glyceryl dioleate (Capmul® GDO, ABITEC), glycerol esters of fatty acids (GELUCIRE 39/01, Gattefosse), dipalmitolein (C16:1) (Larodan), 1,2 and 1,3-diolein (C18:1) (Larodan), dielaidin (C18:1) (Larodan), and dilinolein (C18:2) (Larodan). Formulations of anyone or all of the combinations according to the invention may include one or more of the mono- and diglycerides above.

Sterol and sterol derivatives may also be used as excipients for the formulation of anyone or all of the combinations described herein. Examples of commercially available sterol and sterol derivatives include: cholesterol, sitosterol, lanosterol, PEG-24 cholesterol ether (Solulan C-24, Amerchol), PEG-30 cholestanol (Phytosterol GENEROL series, Henkel), PEG-25 phytosterol (Nikkol BPSH-25, Nikko), PEG-5 soyasterol (Nikkol BPS-5, Nikko), PEG-10 soyasterol (Nikkol BPS-10, Nikko), PEG-20 soyasterol (Nikkol BPS-20, Nikko), and PEG-30 soyasterol (Nikkol BPS-30, Nikko). Formulations of anyone or all of the combinations according to the invention may include one or more of the sterol and sterol derivatives above.

Polyethylene glycol sorbitan fatty acid esters may also be used as excipients for the formulation of anyone or all of the combinations described herein. Examples of commercially available polyethylene glycol sorbitan fatty acid esters include: PEG-10 sorbitan laurate (Liposorb L-10, Lipo Chem.), PEG-20 sorbitan monolaurate (Tween® 20, Atlas/ ICI), PEG-4 sorbitan monolaurate (Tween® 21, Atlas/ICI), PEG-80 sorbitan monolaurate (Hodag PSML-80, Calgene), PEG-6 sorbitan monolaurate (Nikkol GL-1, Nikko), PEG-20 sorbitan monopalmitate (Tween® 40, Atlas/ICI), PEG-20 sorbitan monostearate (Tween® 60, Atlas/ICI), PEG-4 sorbitan monostearate (Tween® 61, Atlas/ICI), PEG-8 sorbitan monostearate (DACOL MSS, Condea), PEG-6 sorbitan monostearate (Nikkol TS106, Nikko), PEG-20 sorbitan tristearate (Tween® 65, Atlas/ICI), PEG-6 sorbitan tetrastearate (Nikkol GS-6, Nikko), PEG-60 sorbitan tetrastearate (Nikkol GS-460, Nikko), PEG-5 sorbitan monooleate (Tween® 81, Atlas/ICI), PEG-6 sorbitan monooleate (Nikkol TO-106, Nikko), PEG-20 sorbitan monooleate (Tween® 80, Atlas/ ICI), PEG-40 sorbitan oleate (Emalex ET 8040, Nihon Emulsion), PEG-20 sorbitan trioleate (Tween® 85, Atlas/ICI), PEG-6 sorbitan tetraoleate (Nikkol GO-4, Nikko), PEG-30 sorbitan tetraoleate (Nikkol GO-430, Nikko), PEG-40 sorbitan tetraoleate (Nikkol GO-440, Nikko), PEG-20 sorbitan monoisostearate (Tween® 120, Atlas/ICI), PEG sorbitol hexaoleate (Atlas G-1086, ICI), polysorbate 80 (Tween® 80, Pharma), polysorbate 85 (Tween® 85, Pharma), polysorbate 20 (Tween® 20, Pharma), polysorbate 40 (Tween® 40, Pharma), polysorbate 60 (Tween® 60, Pharma), and PEG-6 sorbitol hexastearate (Nikkol GS-6, Nikko). Formulations of anyone or all of the combinations according to the invention may include one or more of the polyethylene glycol sorbitan fatty acid esters above.

In addition, polyethylene glycol alkyl ethers may be used as excipients for the formulation of anyone or all of the combinations described herein. Examples of commercially available polyethylene glycol alkyl ethers include: PEG-2 oleyl ether, oleth-2 (Brij 92/93, Atlas/ICI), PEG-3 oleyl ether, oleth-3 (Volpo 3, Croda), PEG-5 oleyl ether, oleth-5 (Volpo 5, Croda), PEG-10 oleyl ether, oleth-10 (Volpo 10, Croda), PEG-20 oleyl ether, oleth-20 (Volpo 20, Croda), PEG-4 lauryl ether, laureth-4 (Brij 30, Atlas/ICI), PEG-9 lauryl ether, PEG-23 lauryl ether, laureth-23 (Brij 35, Atlas/ICI), PEG-2 cetyl ether (Brij 52, ICI), PEG-10 cetyl ether (Brij 56, ICI), PEG-20 cetyl ether (BriJ 58, ICI), PEG-2 stearyl ether (Brij 72, ICI), PEG-10 stearyl ether (Brij 76, ICI), PEG-20 stearyl ether (Brij 78, ICI), and PEG-100 stearyl ether (Brij 700, ICI). Formulations of anyone or all of the combinations according to the invention may include one or more of the polyethylene glycol alkyl ethers above.

Sugar esters may also be used as excipients for the formulation of anyone or all of the combinations described herein. Examples of commercially available sugar esters include: sucrose distearate (SUCRO ESTER 7, Gattefosse), sucrose distearate/monostearate (SUCRO ESTER 11, Gattefosse), sucrose dipalmitate, sucrose monostearate (Crodesta F-160, Croda), sucrose monopalmitate (SUCRO ESTER 15, Gattefosse), and sucrose monolaurate (Saccharose monolaurate 1695, Mitsubisbi-Kasei). Formulations of anyone or all of the combinations according to the invention may include one or more of the sugar esters above.

Polyethylene glycol alkyl phenols are also useful as excipients for the formulation of anyone or all of the combinations described herein. Examples of commercially available polyethylene glycol alkyl phenols include: PEG-10-100 nonylphenol series (Triton X series, Rohm & Haas) and PEG-15-100 octylphenol ether series (Triton N-series, Rohm & Haas). Formulations of anyone or all of the combinations to the invention may include one or more of the polyethylene glycol alkyl phenols above.

Polyoxyethylene-polyoxypropylene block copolymers may also be used as excipients for the formulation of anyone or all of the combinations described herein. These surfactants are available under various trade names, including one or more of Synperonic PE series (ICI), Pluronic® series (BASF), Lutrol (BASF), Supronic, Monolan, Pluracare, and Plurodac. The generic term for these copolymers is "poloxamer" (CAS 9003-11-6). These polymers have the formula shown below:

where "a" and "b" denote the number of polyoxyethylene and polyoxypropylene units, respectively. These copolymers are available in molecular weights ranging from 1000 to 15000 daltons, and with ethylene oxide/propylene oxide ratios between 0.1 and 0.8 by weight. Formulations of anyone or all of the combinations according to the invention may include one or more of the polyoxyethylene-polyoxypropylene block copolymers above.

Polyoxyethylenes, such as PEG 300, PEG 400, and PEG 600, may be used as excipients for the formulation of anyone or all of the combinations described herein.

Sorbitan fatty acid esters may also be used as excipients for the formulation of anyone or all of the combinations described herein. Examples of commercially sorbitan fatty acid esters include: sorbitan monolaurate (Span-20, Atlas/ICI), sorbitan monopalmitate (Span-40, Atlas/ICI), sorbitan monooleate (Span-80, Atlas/ICI), sorbitan monostearate (Span-60, Atlas/ICI), sorbitan trioleate (Span-85, Atlas/ICI), sorbitan sesquioleate (Arlacel-C, ICI), sorbitan tristearate (Span-65, Atlas/ICI), sorbitan monoisostearate (Crill 6, Croda), and sorbitan sesquistearate (Nikkol SS-15, Nikko). Formulations of anyone or all of the combinations according to the invention may include one or more of the sorbitan fatty acid esters above.

Esters of lower alcohols ($C_2$ to $C_4$) and fatty acids ($C_8$ to $C_{18}$) are suitable surfactants for use in the invention. Examples of these surfactants include: ethyl oleate (Crodamol EO, Croda), isopropyl myristate (Crodamol IPM, Croda), isopropyl palmitate (Crodamol IPP, Croda), ethyl linoleate (Nikkol VF-E, Nikko), and isopropyl linoleate (Nikkol VF-IP, Nikko). Formulations of anyone or all of the combinations according to the invention may include one or more of the lower alcohol fatty acid esters above.

In addition, ionic surfactants may be used as excipients for the formulation of anyone or all of the combinations described herein. Examples of useful ionic surfactants include: sodium caproate, sodium caprylate, sodium caprate, sodium laurate, sodium myristate, sodium myristolate, sodium palmitate, sodium palmitoleate, sodium oleate, sodium ricinoleate, sodium linoleate, sodium linolenate, sodium stearate, sodium lauryl sulfate (dodecyl), sodium tetradecyl sulfate, sodium lauryl sarcosinate, sodium dioctyl sulfosuccinate, sodium cholate, sodium taurocholate, sodium glycocholate, sodium deoxycholate, sodium taurodeoxycholate, sodium glycodeoxycholate, sodium ursodeoxycholate, sodium chenodeoxycholate, sodium taurochenodeoxycholate, sodium glyco cheno deoxycholate, sodium cholylsarcosinate, sodium N-methyl taurocholate, egg yolk phosphatides, hydrogenated soy lecithin, dimyristoyl lecithin, lecithin, hydroxylated lecithin, lysophosphatidylcholine, cardiolipin, sphingomyelin, phosphatidylcholine, phosphatidyl ethanolamine, phosphatidic acid, phosphatidyl glycerol, phosphatidyl serine, diethanolamine, phospholipids, polyoxyethylene-10 oleyl ether phosphate, esterification products of fatty alcohols or fatty alcohol ethoxylates, with phosphoric acid or anhydride, ether carboxylates (by oxidation of terminal OH group of, fatty alcohol ethoxylates), succinylated monoglycerides, sodium stearyl fumarate, stearoyl propylene glycol hydrogen succinate, mono/diacetylated tartaric acid esters of mono- and diglycerides, citric acid esters of mono-, diglycerides, glyceryl-lacto esters of fatty acids, acyl lactylates, lactylic esters of fatty acids, sodium stearoyl-2-lactylate, sodium stearoyl lactylate, alginate salts, propylene glycol alginate, ethoxylated alkyl sulfates, alkyl benzene sulfones, α-olefin sulfonates, acyl isethionates, acyl taurates, alkyl glyceryl ether sulfonates, sodium octyl sulfosuccinate, sodium undecylenamideo-MEA-sulfosuccinate, hexadecyl triammonium bromide, decyl trimethyl ammonium bromide, cetyl trimethyl ammonium bromide, dodecyl ammonium chloride, alkyl benzyldimethylammonium salts, diisobutyl phenoxyethoxydimethyl benzylammonium salts, alkylpyridinium salts, betaines (trialkylglycine), lauryl betaine (N-lauryl,N,N-dimethylglycine), and ethoxylated amines (polyoxyethylene-15 coconut amine). For simplicity, typical counterions are provided above. It will be appreciated by one skilled in the art, however, that any bioacceptable counterion may be used. For example, although the fatty acids are shown as sodium salts, other cation counterions can also be used, such as, for example, alkali metal cations or ammonium. Formulations of anyone or all of the combinations according to the invention may include one or more of the ionic surfactants above.

The excipients present in the formulations of the invention are present in amounts such that the carrier forms a clear, or opalescent, aqueous dispersion of the tetra-substituted pyrimidopyrimidine, or the SSRI or the antihistamine, or anyone or all of the combination sequestered within the liposome. The relative amount of a surface active excipient necessary for the preparation of liposomal or solid lipid nanoparticulate formulations is determined using known methodology. For example, liposomes may be prepared by a variety of techniques, such as those detailed in Szoka et al, 1980. Multilamellar vesicles (MLVs) can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

Other established liposomal formulation techniques can be applied as needed. For example, the use of liposomes to facilitate cellular uptake is described in U.S. Pat. Nos. 4,897,355 and 4,394,448.

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

The two compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Thus, for compositions adapted for oral use, an oral vehicle (e.g., a capsule) containing from between 0.01% to 25% (w/w) or more of a tetra-substituted pyrimidopyrimidine or analog and/or additional agent, preferably from between 0.01% to 10% (w/w), more preferably from between 0.05% to 4% (w/w) active agent. The capsule can be taken one to four times daily, or as needed.

For example, for dipyridamole adapted for oral administration, an oral vehicle will contain from between 0.01% to 5% (w/w), preferably from between 0.01% to 2% (w/w), more preferably from between 0.01% to 1% (w/w) dipyridamole.

Performing the methods described herein, the oral vehicle containing a compound of dipyridamole or dipyridamole analog, and/or the additional agent is preferably taken orally. For example, a capsule may be taken in the morning and one in the evening by a subject suffering from an immunoinflammatory disorder or an immunoinflammatory-related disorder, like anti-platelet aggregatory activity.

Topical Formulations

Compositions can also be adapted for topical use with a topical vehicle containing from between 0.0001% to 25% (w/w) or more of tetra-substituted pyrimidopyrimidine and/or analog and between 0.001% to 25% (w/w) and more of antihistamine and/or analog. In such combinations, it is preferred that the tetra-substituted pyrimidopyrimidine is subjected to an extended-release mechanism.

In a preferred combination, the antihistamine and/or tetra-substituted pyrimidopyrimidine are preferably from between 0.0001% to 10% (w/w), more preferably from between 0.0005% to 4% (w/w) active agent. The cream can be applied one to four times daily, or as needed. For example, for prednisolone adapted for topical administration, a topical vehicle will contain from between 0.01% to 5% (w/w), preferably from between 0.01% to 2% (w/w), more preferably from between 0.01% to 1% (w/w) prednisolone in combination with tetra-substituted pyrimidopyrimidine, which is 0.0001% to 2% (w/w), more preferably from between 0.0005% to 1% (w/w).

Performing the methods described herein, the topical vehicle containing a compound of antihistamine or antihistamine analog, and/or the tetra-substituted pyrimidopyrimidine is preferably applied to the site of discomfort on the subject. For example, a cream may be applied to the hands of a subject suffering from arthritic fingers, while topical eye drops may be applied to an eye of a subject to treat uveitis.

Inhalation

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

Dosages

Given the enhanced potency of the combinations of the invention, it is understood that a low dosage (as defined herein) of the tetra-substituted pyrimidopyrimidine and/or the additional agents can be used. These dosages will vary depending on the health and condition of the patient. Thus, a moderate dosage or even a high dosage of one or both agents can be used.

Administration of each drug in the combination can, independently, be one to four times daily for one day to one year, and may even be for the life of the patient. Chronic, long-term administration will be indicated in many cases.

Additional Applications

The compounds of the invention are also useful as screening tools. Single agents and combinations of the invention can be employed in antiproliferative or mechanistic assays to determine whether other combinations, or single agents are as effective as the combination in inhibiting the proliferation of proinflammatory cytokines using assays generally known in the art, e.g., TNFα, IL-1, IL-2, IFN-γ etc., specific, non-limiting examples of which are described in the Examples section. For example, candidate compounds are combined with a compound from with either the tetra-substituted pyrimidopyrimidine (or tetra-substituted pyrimidopyrimidine analog) or the additional agents described herein, applied to stimulate PBMCs, and at after a suitable time, the cells are examined for anitproliferative activity, TNFα or other assays for proinflammatory cytokine secretion. The relative effects of the combinations versus each other, and versus the single agents are compared, and effective compounds and combinations are identified. The screening method can be used for comparing the activity of novel single agents or new combinations of agents (novel or known) for relative activity in the assays.

The combinations of the invention are also useful tools in elucidating mechanistic information about the biological pathways involved in inflammation or novel targets. Such information can lead to the development of new combinations or single agents (mechanistic and/or structural analogs of either the tetra-substituted pyrimidopyrimidine or companion compound) for inhibiting proinflammatory cytokine secretion. Methods known in the art to determine biological pathways can be used to determine the pathway, or network of pathways affected by contacting cells stimulated to produce proinflammatory cytokines with the compounds of the invention.

Such methods can include, analyzing cellular constituents that are expressed or repressed after contact with the compounds of the invention as compared to untreated, positive or negative control compounds, and/or new single agents and combinations, or analyzing some other metabolic activity of the cell such as enzyme activity, nutrient uptake, and proliferation. Cellular components analyzed can include gene transcripts, and protein expression. Suitable methods can include standard biochemistry techniques, radiolabeling the compounds of the invention (e,.g., $^{14}C$ or $^{3}H$ labeling), and observing the compounds binding to proteins, e.g. using 2d gels, gene expression profiling. Once identified, such compounds can be used in in vivo models to further validate the tool or develop new anti-inflammatory agents.

EXAMPLE

The following example is to illustrate the invention, and is not meant to limit the invention in any way.

Methods

TNFα Secretion Assay

The effects of test compound combinations on TNFα secretion were assayed in white blood cells from human buffy coat stimulated with LPS or phorbol 12-myristate 13-acetate- and ionomycin as follows. Human white blood cells from buffy coat were diluted 1:50 in media (RPMI; Gibco BRL, #11875-085), 10% fetal bovine serum (Gibco BRL, #25140-097), 2% penicillin/streptomycin (Gibco BRL, #15140-122)) and 50 μL of the diluted white blood cells was placed in each well of the assay plate. Drugs were added to the indicated concentration. After 16-18 hours of incubation at 37° C. with 5% $CO_2$ in a humidified incubator, the plate was centrifuged and the supernatant transferred to a white opaque polystyrene 384-well plate (NalgeNunc, Maxisorb) coated with an anti-TNFα antibody (PharMingen, #551220). After a two-hour incubation, the plate was washed (Tecan Powerwasher 384) with PBS containing 0.1% Tween 20 and incubated for one additional hour with biotin labeled anti-TNFa antibody (PharMingen, #554511) and HRP coupled to streptavidin (PharMingen, #13047E). The plate was then washed again with 0.1% Tween 20/PBS. An HRP-luminescent substrate was added to each well, and the light intensity of each well was measured using a plate luminometer.

IFNγ Secretion Assay

The effects of test compound combinations on IFN-γ secretion were assayed in white blood cells from human buffy coat stimulated with phorbol 12-myristate 13-acetate as follows. Human white blood cells from buffy coat were diluted 1:50 in media (RPMI; Gibco BRL, #11875-085), 10% fetal bovine serum (Gibco BRL, #25140-097), 2% penicillin/streptomycin (Gibco BRL, #15140-122)) and 50 μL of the diluted white blood cells was placed in each well of the final assay plate created in the above section. After 16-18 hours of incubation at 37° C. with 5% CO2 in a humidified incubator, the plate was centrifuged and the supernatant transferred to a white opaque polystyrene 384-well plate (NalgeNunc, Maxisorb) coated with an anti-IFN-γ antibody (Endogen, M-700-AE). After a two-hour incubation, the plate was washed (Tecan Powerwasher 384) with PBS containing 0.1% Tween 20 and incubated for one additional hour with biotin labeled anti-IFN-γ antibody (Endogen, M-701-B) and HRP coupled to streptavidin (PharMingen, #13047E). The plate was then washed again with 0.1% Tween 20/PBS. An HRP-luminescent substrate was added to each well, and the light intensity of each well was measured using a plate luminometer.

IL-1 Secretion Assay

The effects of test compound combinations on IL-1 secretion were assayed in white blood cells from human buffy coat stimulated with LPS, as follows. Human white blood cells from buffy coat were diluted 1:50 in media (RPMI; Gibco BRL, #11875-085), 10% fetal bovine serum (Gibco BRL, #25140-097), 2% penicillin/streptomycin (Gibco BRL, #15140-122)) and 50 μL of the diluted white blood cells was placed in each well of the final assay plate created in the above section. After 16-18 hours of incubation at 37° C. in a humidified incubator, the plate was centrifuged and the supernatant was transferred to a white opaque 384-well plate (Nalge-Nunc, MAXISORB) coated with an anti-IL-1 antibody (R&D Systems, MAB601). After a two-hour incubation, the plate was washed (Tecan Powerwasher 384) with PBS containing 0.1% Tween 20 and incubated for an additional one hour with a biotin labeled anti-IL-1 antibody (R&D Systems, BAF201) and horse radish peroxidase coupled to streptavidin (PharMingen, #554066). The plate was then washed again with 0.1% Tween 20/PBS, and an HRP-luminescent substrate was added to each well. Light intensity was then measured using a plate luminometer.

IL-2 Secretion Assay

The effects of test compound combinations on IL-2 secretion were assayed in white blood cells from human buffy coat stimulated with phorbol 12-myristate 13-acetate, as follows. Human white blood cells from buffy coat were diluted 1:50 in media (RPMI; Gibco BRL, #11875-085), 10% fetal bovine serum (Gibco BRL, #25140-097), 2% penicillin/streptomycin (Gibco BRL, #15140-122)) and 50 μL of the diluted white blood cells was placed in each well of the final assay plate created in the above section. After 16-18 hours of incubation at 37° C. in a humidified incubator, the plate was centrifuged and the supernatant was transferred to a white opaque 384-well plate (NalgeNunc, MAXISORB) coated with an anti-IL-2 antibody (PharMingen, #555051). After a two-hour incubation, the plate was washed (Tecan Powerwasher 384) with PBS containing 0.1% Tween 20 and incubated for an additional one hour with a biotin labeled anti-IL-2 antibody (Endogen, M600B) and horse radish peroxidase coupled to streptavidin (PharMingen, #13047E). The plate was then washed again with 0.1% Tween 20/PBS, and an HRP-luminescent substrate was added to each well. Light intensity was then measured using a plate luminometer.

Percent Inhibition

The percent inhibition (%I) for each well was calculated using the following formula:

% I=[(avg. untreated wells−treated well)/(avg. untreated wells)]×100

The average untreated well value (avg. untreated wells) is the arithmetic mean of 40 wells from the same assay plate treated with vehicle alone. Negative inhibition values result from local variations in treated wells as compared to untreated wells.

The results of various combinations of compounds described on the reduction of TNFα, IL-2, IL-1, or IFN-γ secretion are shown below in Tables 7-53. The effects of varying concentrations of single compound or when used in combination with another compound is shown in individual tables. For example, Table 8 shows the effects of varying concentrations of dipyridamole and a combination of dipyridamole and bromodiphenhydramine HCl. These results were compared to control wells. These wells were stimulated with phorbol 12-myristate 13-acetate and ionomycin, but did not receive dipyridamole or bromodiphenhydramine HCl. The effects of the agents alone and in combination are shown as percent inhibition of TNFα secretion. In Tables 7-26, TNF-α suppression was determined after cells were stimulated with phorbol 12-myristate 13-acetate and ionomycin.

TABLE 7

| | | Dipyridamole (μM) | | | | | | | |
|---|---|---|---|---|---|---|---|---|---|
| | | 0 | 0.15 | 0.3 | 0.61 | 1.2 | 2.4 | 4.9 | 9.7 | 19 |
| Bromodiphenhydramine HCl (μM) | 0 | −4.6 | 3.4 | 0.92 | 6.6 | 12 | 25 | 40 | 54 | 71 |
| | 0.21 | 0 | 4.5 | 7.7 | 11 | 13 | 24 | 39 | 54 | 73 |
| | 0.43 | −4.4 | 7.6 | 5.1 | 11 | 15 | 23 | 41 | 53 | 71 |
| | 0.85 | 0.72 | 9 | 8.6 | 15 | 23 | 25 | 40 | 55 | 71 |
| | 1.7 | −2.4 | 5.1 | 7.4 | 10 | 20 | 31 | 41 | 54 | 67 |
| | 3.4 | 5.6 | 17 | 19 | 22 | 30 | 36 | 45 | 58 | 74 |

TABLE 7-continued

| Dipyridamole (μM) | | | | | | | | | |
|---|---|---|---|---|---|---|---|---|---|
| | 0 | 0.15 | 0.3 | 0.61 | 1.2 | 2.4 | 4.9 | 9.7 | 19 |
| | 6.8 | 13 | 24 | 25 | 26 | 46 | 47 | 56 | 70 | 75 |
| | 14 | 34 | 45 | 41 | 43 | 47 | 60 | 65 | 67 | 77 |
| | 27 | 61 | 61 | 66 | 72 | 70 | 70 | 77 | 76 | 82 |

TABLE 8

| | | Dipyridamole (μM) | | | | | | | | |
|---|---|---|---|---|---|---|---|---|---|---|
| | | 0 | 0.15 | 0.3 | 0.61 | 1.2 | 2.4 | 4.9 | 9.7 | 19 |
| Cyproheptadine HCl (μM) | 0 | −4.2 | 4.5 | −0.27 | 4.3 | 0.57 | 12 | 33 | 49 | 63 |
| | 0.24 | 0.32 | −1.3 | −1.3 | 5.7 | 4.6 | 15 | 38 | 50 | 71 |
| | 0.48 | 2 | 12 | 4.6 | 7 | 13 | 19 | 34 | 52 | 64 |
| | 0.96 | 1.2 | 12 | 5.1 | 9.9 | 8.7 | 21 | 41 | 54 | 68 |
| | 1.9 | 4.6 | 9.2 | 10 | 15 | 21 | 25 | 43 | 55 | 65 |
| | 3.9 | 2.4 | 13 | 21 | 22 | 23 | 32 | 47 | 62 | 71 |
| | 7.7 | 15 | 32 | 36 | 45 | 40 | 47 | 61 | 66 | 78 |
| | 15 | 29 | 44 | 46 | 50 | 60 | 56 | 70 | 68 | 84 |
| | 31 | 29 | 44 | 46 | 50 | 60 | 73 | 70 | 80 | 84 |

TABLE 9

| | | Dipyridamole (μM) | | | | | | | | |
|---|---|---|---|---|---|---|---|---|---|---|
| | | 0 | 0.15 | 0.3 | 0.61 | 1.2 | 2.4 | 4.9 | 9.7 | 19 |
| Loratadine (μM) | 0 | −6.4 | 6.5 | 9.6 | 12 | 16 | 30 | 37 | 55 | 70 |
| | 0.2 | 0 | 7.5 | 6.4 | 11 | 14 | 28 | 40 | 52 | 71 |
| | 0.41 | −6.2 | 3.4 | 5.5 | 14 | 13 | 29 | 41 | 62 | 70 |
| | 0.82 | −2.1 | 4.8 | 3.9 | 5.3 | 11 | 23 | 39 | 54 | 71 |
| | 1.6 | −2.4 | 7.4 | 6 | 12 | 13 | 26 | 45 | 58 | 71 |

TABLE 9-continued

| | Dipyridamole (μM) | | | | | | | | |
|---|---|---|---|---|---|---|---|---|---|
| | 0 | 0.15 | 0.3 | 0.61 | 1.2 | 2.4 | 4.9 | 9.7 | 19 |
| 3.3 | 8.1 | 17 | 12 | 20 | 24 | 35 | 45 | 61 | 73 |
| 6.5 | 11 | 21 | 25 | 31 | 34 | 44 | 65 | 68 | 80 |
| 13 | 31 | 44 | 42 | 47 | 49 | 61 | 67 | 77 | 67 |
| 26 | 31 | 44 | 42 | 47 | 49 | 61 | 67 | 77 | 66 |

TABLE 10

| | | Dipyridamole (μM) | | | | | | | | |
|---|---|---|---|---|---|---|---|---|---|---|
| | | 0 | 0.15 | 0.3 | 0.61 | 1.2 | 2.4 | 4.9 | 9.7 | 19 |
| Thiethylperazine maleate (μM) | 0 | −4.1 | 6.1 | 7 | 9.1 | 19 | 27 | 40 | 54 | 71 |
| | 0.2 | −3.3 | 6.4 | 12 | 11 | 18 | 26 | 42 | 54 | 72 |
| | 0.39 | −3.9 | 8.2 | 11 | 16 | 18 | 26 | 44 | 55 | 71 |
| | 0.78 | −1 | 3.8 | 9.8 | 16 | 20 | 29 | 42 | 56 | 70 |
| | 1.6 | −3.4 | 5.1 | 4.6 | 16 | 18 | 28 | 42 | 56 | 71 |
| | 3.1 | 1.4 | 15 | 16 | 20 | 24 | 37 | 49 | 62 | 70 |
| | 6.3 | 15 | 27 | 27 | 34 | 41 | 50 | 61 | 71 | 82 |
| | 13 | 51 | 62 | 61 | 64 | 67 | 72 | 79 | 85 | 89 |
| | 25 | 62 | 75 | 76 | 77 | 88 | 87 | 87 | 90 | 95 |

TABLE 11

| | | Prednisolone (μM) | | | | | | | | |
|---|---|---|---|---|---|---|---|---|---|---|
| | | 0 | 0.0078 | 0.016 | 0.031 | 0.062 | 0.12 | 0.25 | 0.5 | 1 |
| Dipyridamole (μM) | 0 | −2.57 | 1.47 | 1.37 | 7.82 | 15.1 | 18 | 21.5 | 29.9 | 34 |
| | 0.3 | 4.32 | 12.6 | 13.1 | 18.1 | 21 | 27.6 | 32.2 | 37.8 | 39.7 |
| | 0.61 | 2.88 | 7.18 | 14.2 | 18.5 | 24.9 | 29.2 | 35.6 | 36.9 | 42.7 |
| | 1.2 | 10.8 | 12.2 | 15.5 | 20.8 | 28.9 | 31.7 | 39 | 42.4 | 46.7 |
| | 2.4 | 19.3 | 24.8 | 28.9 | 31.5 | 38.3 | 38.8 | 48.6 | 53.6 | 50.6 |
| | 4.9 | 34.1 | 42 | 41.9 | 46.9 | 50.8 | 54.4 | 58.7 | 59.8 | 62.5 |
| | 9.7 | 51.4 | 58.2 | 57.3 | 59.3 | 64.1 | 69.6 | 69.3 | 70.9 | 74 |
| | 19 | 68.8 | 70.2 | 73.3 | 72.6 | 74.5 | 79.4 | 80.8 | 83.2 | 82.3 |
| | 39 | 80.8 | 85.5 | 85.1 | 87.9 | 87.6 | 88.2 | 88.6 | 89.8 | 90.6 |

TABLE 12

| | | \multicolumn{9}{c}{Dipyridamole (μM)} | | | | | | | |
|---|---|---|---|---|---|---|---|---|---|
| | | 0 | 0.3 | 0.61 | 1.2 | 2.4 | 4.9 | 9.7 | 19 | 39 |
| Amoxapine (μM) | 0 | 11 | 19 | 20 | 23 | 30 | 45 | 52 | 63 | 78 |
| | 0.25 | 4.5 | 25 | 30 | 31 | 40 | 48 | 59 | 70 | 83 |
| | 0.5 | 14 | 28 | 25 | 33 | 44 | 51 | 60 | 70 | 84 |
| | 1 | 21 | 36 | 36 | 43 | 50 | 58 | 67 | 74 | 88 |
| | 2 | 35 | 42 | 45 | 49 | 55 | 62 | 73 | 79 | 92 |
| | 4 | 52 | 63 | 56 | 64 | 66 | 71 | 80 | 82 | 94 |
| | 8 | 76 | 76 | 75 | 81 | 83 | 85 | 91 | 93 | 97 |
| | 16 | 92 | 90 | 90 | 91 | 94 | 95 | 96 | 96 | 98 |
| | 32 | 89 | 98 | 97 | 97 | 94 | 98 | 97 | 98 | 97 |

TABLE 13

| | | \multicolumn{9}{c}{Dipyridamole (μM)} | | | | | | | |
|---|---|---|---|---|---|---|---|---|---|
| | | 0 | 0.3 | 0.61 | 1.2 | 2.4 | 4.9 | 9.7 | 19 | 39 |
| Fluoxetine (μM) | 0 | 6.6 | 18 | 12 | 17 | 26 | 42 | 49 | 62 | 76 |
| | 0.45 | −4 | 22 | 18 | 20 | 22 | 40 | 54 | 63 | 77 |
| | 0.9 | 4.1 | 12 | 9.3 | 22 | 31 | 38 | 51 | 64 | 76 |
| | 1.8 | 4.1 | 16 | 15 | 26 | 33 | 40 | 55 | 67 | 78 |
| | 3.6 | 14 | 18 | 17 | 23 | 33 | 46 | 58 | 68 | 81 |
| | 7.2 | 37 | 41 | 38 | 47 | 52 | 58 | 68 | 79 | 86 |
| | 14 | 73 | 73 | 73 | 75 | 82 | 82 | 88 | 90 | 93 |
| | 29 | 94 | 93 | 94 | 94 | 90 | 95 | 95 | 96 | 97 |
| | 58 | 98 | 98 | 98 | 93 | 94 | 98 | 98 | 98 | 98 |

TABLE 14

| | | \multicolumn{9}{c}{Dipyridamole (μM)} | | | | | | | |
|---|---|---|---|---|---|---|---|---|---|
| | | 0 | 0.3 | 0.61 | 1.2 | 2.4 | 4.9 | 9.7 | 19 | 39 |
| Nortriptyl (μM) | 0 | −2 | 14 | 8.6 | 20 | 27 | 43 | 54 | 64 | 80 |
| | 0.52 | −7.2 | 16 | 20 | 18 | 28 | 43 | 55 | 66 | 80 |
| | 1 | 3.4 | 20 | 16 | 27 | 34 | 44 | 56 | 69 | 82 |
| | 2.1 | 13 | 23 | 24 | 33 | 39 | 48 | 61 | 73 | 85 |
| | 4.2 | 25 | 38 | 40 | 48 | 50 | 62 | 74 | 82 | 92 |
| | 8.3 | 55 | 57 | 61 | 71 | 70 | 80 | 83 | 89 | 94 |
| | 17 | 83 | 85 | 85 | 86 | 89 | 90 | 94 | 96 | 97 |
| | 33 | 97 | 97 | 97 | 97 | 96 | 97 | 97 | 97 | 98 |
| | 67 | 98 | 98 | 98 | 98 | 98 | 95 | 98 | 98 | 98 |

TABLE 15

| | | \multicolumn{9}{c}{Dipyridamole (μM)} | | | | | | | |
|---|---|---|---|---|---|---|---|---|---|
| | | 0 | 0.3 | 0.61 | 1.2 | 2.4 | 4.9 | 9.7 | 19 | 39 |
| Paroxetine (μM) | 0 | 14 | 21 | 24 | 23 | 32 | 45 | 53 | 60 | 76 |
| | 0.21 | 9.1 | 27 | 15 | 25 | 30 | 42 | 53 | 64 | 76 |
| | 0.42 | 3.2 | 19 | 14 | 24 | 34 | 37 | 56 | 63 | 77 |
| | 0.83 | 4.3 | 25 | 22 | 28 | 36 | 45 | 56 | 67 | 78 |
| | 1.7 | 13 | 21 | 24 | 32 | 32 | 50 | 59 | 70 | 82 |
| | 3.3 | 24 | 36 | 39 | 47 | 52 | 58 | 69 | 79 | 87 |
| | 6.7 | 69 | 67 | 70 | 73 | 75 | 80 | 85 | 89 | 94 |
| | 13 | 91 | 88 | 91 | 90 | 91 | 93 | 95 | 96 | 97 |
| | 27 | 92 | 95 | 97 | 97 | 79 | 96 | 97 | 98 | 98 |

TABLE 16

| | | \multicolumn{9}{c}{Ibudilast (μM)} | | | | | | | |
|---|---|---|---|---|---|---|---|---|---|
| | | 0 | 0.062 | 0.12 | 0.25 | 0.5 | 1 | 2 | 4 | 8 |
| Dipyridamole (μM) | 0 | −5.712 | 2.754 | 15.92 | 14.65 | 22.88 | 37.42 | 42.85 | 45.88 | 53.83 |
| | 0.15 | 6.492 | 14.03 | 18.1 | 26.02 | 30.25 | 39.4 | 43.67 | 47.98 | 54 |
| | 0.3 | 4.72 | 15.87 | 20.92 | 26.85 | 31.68 | 35.62 | 45.98 | 48.62 | 53.15 |
| | 0.61 | 17.75 | 21.47 | 18.07 | 27.9 | 32.62 | 42.7 | 44.95 | 52.58 | 52.18 |
| | 1.2 | 21.77 | 24.08 | 25.17 | 28.68 | 32.15 | 42.2 | 45.2 | 48.53 | 53.25 |
| | 2.4 | 30.18 | 33.2 | 35.45 | 36.58 | 40.28 | 45.45 | 47.73 | 50.23 | 56.35 |
| | 4.9 | 42.1 | 45.8 | 49.1 | 46.48 | 47.25 | 51.42 | 55.22 | 57 | 60.45 |
| | 9.7 | 59.53 | 60.5 | 62.33 | 61.65 | 60.95 | 62.35 | 63.77 | 64.88 | 66.33 |
| | 19 | 69.65 | 72.98 | 71.9 | 73 | 71.83 | 72.4 | 74.62 | 75.4 | 78 |

TABLE 17

| | | \multicolumn{9}{c}{Dipyridamole (μM)} | | | | | | | |
|---|---|---|---|---|---|---|---|---|---|
| | | 0 | 0.15 | 0.3 | 0.61 | 1.2 | 2.4 | 4.9 | 9.7 | 19 |
| Ro-20-1724 (μM) | 0 | −10.88 | −1.893 | −1.961 | 3.388 | 2.338 | 23.67 | 37.2 | 53.33 | 64.05 |
| | 0.28 | 5.143 | 15.46 | 11.11 | 10.86 | 17.73 | 23.77 | 41.05 | 57.15 | 67.88 |
| | 0.56 | 16.35 | 14.53 | 23.85 | 21.85 | 25.32 | 32.5 | 43.7 | 52 | 65.78 |
| | 1.1 | 21.5 | 25.85 | 25.23 | 29.77 | 33.42 | 34.55 | 48.02 | 55.22 | 67.7 |
| | 2.2 | 27.4 | 30.23 | 33.67 | 34.38 | 37.33 | 40.12 | 47.72 | 58.02 | 68.3 |
| | 4.5 | 38.98 | 37.58 | 35.03 | 38.62 | 41 | 36.98 | 52.12 | 58.88 | 68.97 |
| | 9 | 41.4 | 41.95 | 41.4 | 40.3 | 44.47 | 47.08 | 53.58 | 63.73 | 71 |
| | 18 | 39.33 | 46.28 | 48.9 | 46.17 | 49.95 | 50.1 | 55.18 | 59.8 | 70.15 |
| | 36 | 49.38 | 51.98 | 52.85 | 51.3 | 53.67 | 51.02 | 56.38 | 67.38 | 74.6 |

TABLE 18

| | | \multicolumn{9}{c}{Rolipram (μM)} | | | | | | | |
|---|---|---|---|---|---|---|---|---|---|
| | | 0 | 0.0079 | 0.016 | 0.031 | 0.063 | 0.13 | 0.25 | 0.5 | 1 |
| Dipyridamole (μM) | 0 | −8.49 | 6.115 | 5.793 | 14.26 | 14.4 | 25.82 | 30.73 | 36.8 | 38.9 |
| | 0.15 | 3.725 | 9.935 | 15.98 | 15.8 | 23.9 | 32.25 | 35.85 | 41.55 | 45.35 |
| | 0.3 | 2.362 | 11.36 | 13.07 | 19.6 | 20.55 | 33.03 | 35.77 | 40.77 | 43.6 |

TABLE 18-continued

| | | | | Rolipram (μM) | | | | | | |
|---|---|---|---|---|---|---|---|---|---|---|
| | 0 | 0.0079 | 0.016 | 0.031 | 0.063 | 0.13 | 0.25 | 0.5 | 1 |
| 0.61 | 9.21 | 15.37 | 19.71 | 23.27 | 24.9 | 33.23 | 35.1 | 42.75 | 42.8 |
| 1.2 | 19.42 | 22.95 | 20.25 | 24.9 | 27.02 | 36.55 | 37.75 | 42.38 | 45.73 |
| 2.4 | 29 | 34.85 | 33.8 | 34.75 | 35.08 | 39.27 | 42.62 | 46.2 | 48.93 |
| 4.9 | 42.4 | 44.97 | 45.95 | 46.08 | 46.47 | 50.28 | 51 | 55.18 | 54.3 |
| 9.7 | 58.05 | 58.67 | 60.05 | 59.9 | 59.65 | 59.65 | 61 | 63.03 | 62.55 |
| 19 | 71.15 | 72.88 | 72.2 | 72.95 | 70.95 | 74.12 | 73.53 | 74.43 | 75.72 |

TABLE 19

| | | Betamethasone (nM) | | | | | |
|---|---|---|---|---|---|---|---|
| | | 0 | 2.4 | 9.6 | 38 | 153 | 611 |
| Dipyridamole (μM) | 0 | −2.86 | 3.62 | 15.5 | 26.3 | 34.9 | 35.2 |
| | 30 | −0.43 | 4.37 | 15.2 | 30 | 34.5 | 35.8 |
| | 121 | 2.49 | 9.75 | 21.1 | 32.6 | 39.8 | 40.1 |
| | 486 | 7.6 | 13.9 | 22.7 | 33.5 | 40.3 | 43.2 |
| | 1943 | 12.7 | 18.4 | 26.5 | 38.9 | 44.1 | 46 |
| | 7773 | 31.7 | 35.2 | 43.1 | 52.7 | 57 | 58.5 |

TABLE 20

| | | Budesonide (nM) | | | | | |
|---|---|---|---|---|---|---|---|
| | | 0 | 0.54 | 2.2 | 8.7 | 35 | 139 |
| Dipyridamole (μM) | 0 | −3.92 | 3.31 | 11.9 | 25.6 | 36.3 | 38.7 |
| | 30 | 1.6 | 4.05 | 14.1 | 28.8 | 37.1 | 40 |
| | 121 | 6.91 | 10.9 | 18.4 | 30.6 | 39 | 43 |
| | 486 | 9.01 | 13.2 | 20.7 | 32.1 | 41.3 | 45.1 |
| | 1943 | 14.8 | 16.4 | 23.1 | 36.6 | 45.7 | 47.7 |
| | 7773 | 36.3 | 37 | 43.7 | 51.8 | 58.7 | 61.2 |

TABLE 21

| | | Clobetasol propionate (nM) | | | | | |
|---|---|---|---|---|---|---|---|
| | | 0 | 0.33 | 1.3 | 5.4 | 21 | 86 |
| Dipyridamole (μM) | 0 | −3.68 | 12.1 | 27.4 | 37.1 | 41.2 | 42 |
| | 30 | −0.406 | 13.6 | 27.5 | 39.1 | 43.6 | 44.8 |
| | 121 | 4.51 | 16.9 | 32.5 | 43.4 | 47.4 | 49.2 |
| | 486 | 7.76 | 22.1 | 35 | 45.9 | 49.8 | 52.1 |
| | 1943 | 14.2 | 26.1 | 39.5 | 49.7 | 52.7 | 53.4 |
| | 7773 | 29.7 | 42.6 | 52.2 | 60 | 62.2 | 64.3 |

TABLE 22

| | | Dexamethasone (nM) | | | | | |
|---|---|---|---|---|---|---|---|
| | | 0 | 2.4 | 9.6 | 38 | 153 | 611 |
| Dipyridamole (μM) | 0 | −2.26 | 4.24 | 11.3 | 25.1 | 35.8 | 39.8 |
| | 30 | −0.75 | 4.41 | 13.7 | 28.7 | 36.3 | 41.4 |
| | 121 | 3.75 | 11 | 18 | 29.7 | 39.3 | 42.5 |
| | 486 | 8.17 | 12 | 18 | 32.4 | 39.4 | 42.4 |
| | 1943 | 12.6 | 17.2 | 26.1 | 35.9 | 44.2 | 46.4 |
| | 7773 | 33.6 | 38.7 | 43.4 | 51.5 | 58.9 | 61 |

TABLE 23

| | | Diflorasone diacetate (nM) | | | | | |
|---|---|---|---|---|---|---|---|
| | | 0 | 7.6 | 30 | 121 | 485 | 1941 |
| Dipyridamole (μM) | 0 | −2.18 | 8.02 | 22.2 | 33.3 | 37.6 | 38.5 |
| | 30 | −2.05 | 10.4 | 23.8 | 31.8 | 38.3 | 39.2 |
| | 121 | 6.95 | 16.3 | 28.4 | 38.6 | 41.8 | 43.4 |
| | 486 | 7.66 | 18.1 | 28.3 | 38.6 | 43.7 | 44.9 |
| | 1943 | 11.6 | 21.4 | 32.5 | 43.1 | 47.1 | 47.5 |
| | 7773 | 26 | 32.1 | 41.7 | 52.5 | 56.3 | 55.8 |

TABLE 24

| | | Hydrocortisone (nM) | | | | | |
|---|---|---|---|---|---|---|---|
| | | 0 | 21 | 83 | 331 | 1324 | 5297 |
| Dipyridamole (μM) | 0 | −2.48 | 0.846 | 8.64 | 22.2 | 32 | 37.9 |
| | 30 | 0.156 | 4.63 | 12.3 | 24.1 | 33.8 | 37.9 |
| | 121 | 5.34 | 7.83 | 15.6 | 30.4 | 39.2 | 42.7 |
| | 486 | 8.82 | 10.8 | 18.1 | 30.8 | 39.2 | 44.6 |
| | 1943 | 13.2 | 15.7 | 23.6 | 36.6 | 45.5 | 49.8 |
| | 7773 | 30 | 33.7 | 41.5 | 51.5 | 59.5 | 60.9 |

TABLE 25

| | | Prednisolone (nM) | | | | | |
|---|---|---|---|---|---|---|---|
| | | 0 | 10 | 42 | 166 | 664 | 2656 |
| Dipyridamole (μM) | 0 | −1.15 | 1.03 | 7.87 | 22.9 | 34.9 | 39 |
| | 30 | −0.749 | 4 | 9.98 | 25.2 | 37.3 | 41 |
| | 121 | 7.28 | 9.96 | 16.2 | 30.1 | 42.1 | 46.1 |
| | 486 | 10.7 | 14.4 | 17.4 | 32.2 | 44 | 46.3 |
| | 1943 | 17 | 15.9 | 25.2 | 38.1 | 47.1 | 51.3 |
| | 7773 | 33.5 | 35.8 | 40.9 | 52.4 | 60.8 | 62.4 |

TABLE 26

| | | Triamcinolone (nM) | | | | | |
|---|---|---|---|---|---|---|---|
| | | 0 | 9.5 | 38 | 152 | 609 | 2434 |
| Dipyridamole (μM) | 0 | −1.64 | 3.74 | 12.2 | 26.4 | 35.1 | 37.2 |
| | 30 | −0.021 | 4.41 | 15.3 | 29.1 | 36.1 | 40.4 |
| | 121 | 4.48 | 9.43 | 18.5 | 31.7 | 40.9 | 43.3 |
| | 486 | 8.72 | 13.7 | 21.7 | 34.1 | 42.8 | 45.5 |
| | 1943 | 16 | 18.1 | 29.1 | 39.7 | 47.1 | 50.5 |
| | 7773 | 30.5 | 35.1 | 41.9 | 53 | 59 | 61.9 |

In Tables 27-38, TNFα suppression was determined after cells were stimulated with LPS.

TABLE 27

| | | \multicolumn{9}{c}{Prednisolone (μM)} |
|---|---|---|---|---|---|---|---|---|---|---|
| | | 0 | 0.0078 | 0.016 | 0.031 | 0.062 | 0.12 | 0.25 | 0.5 | 1 |
| Dipyridamole (μM) | 0 | −2.05 | −0.704 | −0.915 | 8.37 | 21.7 | 31.4 | 41.5 | 45.5 | 52.5 |
| | 0.15 | 5.72 | 8.79 | 6.98 | 5.76 | 17 | 38 | 47.3 | 57.9 | 64.6 |
| | 0.3 | 7.3 | 10.5 | 13.7 | 19.9 | 23.9 | 39.2 | 46 | 52 | 55.3 |
| | 0.61 | 24.9 | 20.8 | 13.4 | 23.9 | 41.8 | 34.6 | 52.5 | 61.7 | 63.1 |
| | 1.2 | 27.3 | 15.2 | 26.3 | 37.9 | 35.7 | 43.5 | 62.2 | 58.9 | 68.3 |
| | 2.4 | 37.2 | 47.4 | 42.6 | 42.2 | 57.4 | 46.6 | 68.7 | 71.5 | 72.1 |
| | 4.9 | 54.3 | 51.4 | 53.2 | 63.9 | 69.5 | 61.3 | 73.1 | 76.5 | 78.6 |
| | 9.7 | 71.1 | 71.1 | 67.5 | 73.4 | 75.5 | 73.3 | 78.4 | 79.3 | 83 |
| | 19 | 82.7 | 79 | 78.9 | 72.3 | 80.3 | 78 | 83 | 86 | 87.4 |
| | 39 | 83 | 73.6 | 84 | 81.7 | 80.5 | 80.7 | 78.8 | 82.4 | 80.3 |

TABLE 28

| | | \multicolumn{9}{c}{Dipyridamole (μM)} |
|---|---|---|---|---|---|---|---|---|---|---|
| | | 0 | 0.3 | 0.61 | 1.2 | 2.4 | 4.9 | 9.7 | 19 | 39 |
| Amoxapine (μM) | 0 | 5.7 | 14 | 21 | 31 | 30 | 45 | 67 | 77 | 87 |
| | 0.25 | 0.94 | 11 | 17 | 27 | 27 | 51 | 62 | 76 | 85 |
| | 0.5 | −9.7 | 17 | 11 | 22 | 28 | 48 | 68 | 79 | 86 |
| | 1 | −2.8 | 17 | 23 | 19 | 38 | 51 | 65 | 77 | 86 |
| | 2 | 1.2 | 18 | 19 | 26 | 35 | 54 | 69 | 79 | 88 |
| | 4 | −1.3 | 24 | 19 | 30 | 46 | 63 | 74 | 78 | 88 |
| | 8 | 13 | 25 | 31 | 38 | 57 | 64 | 78 | 84 | 90 |
| | 16 | 29 | 48 | 54 | 59 | 71 | 77 | 85 | 89 | 92 |
| | 32 | 47 | 76 | 74 | 79 | 85 | 89 | 92 | 94 | 93 |

TABLE 29

| | | \multicolumn{9}{c}{Dipyridamole (μM)} |
|---|---|---|---|---|---|---|---|---|---|---|
| | | 0 | 0.3 | 0.61 | 1.2 | 2.4 | 4.9 | 9.7 | 19 | 39 |
| Fluoxetine (μM) | 0 | 15 | 21 | 17 | 26 | 35 | 52 | 65 | 76 | 85 |
| | 0.45 | −4.8 | 15 | 8.9 | 15 | 25 | 50 | 64 | 78 | 84 |
| | 0.9 | −8.5 | 13 | 8 | 21 | 33 | 55 | 66 | 79 | 86 |
| | 1.8 | −4.5 | 11 | 7.6 | 10 | 31 | 50 | 65 | 74 | 83 |
| | 3.6 | −10 | 10 | 14 | 28 | 34 | 49 | 73 | 79 | 85 |
| | 7.2 | −11 | 4.9 | 9.2 | 22 | 33 | 58 | 71 | 80 | 86 |
| | 14 | −2 | −9.3 | −6.7 | 9.9 | 22 | 48 | 73 | 81 | 85 |
| | 29 | 79 | 76 | 75 | 83 | 84 | 88 | 90 | 93 | 86 |
| | 58 | 85 | 87 | 90 | 90 | 92 | 91 | 90 | 95 | 80 |

TABLE 30

| | | \multicolumn{9}{c}{Dipyridamole (μM)} |
|---|---|---|---|---|---|---|---|---|---|---|
| | | 0 | 0.3 | 0.61 | 1.2 | 2.4 | 4.9 | 9.7 | 19 | 39 |
| Nortriptyline (μM) | 0 | 12 | 22 | 18 | 28 | 38 | 54 | 69 | 78 | 87 |
| | 0.52 | 2 | 7.7 | 16 | 26 | 32 | 54 | 66 | 80 | 87 |
| | 1 | −3.2 | 14 | 17 | 20 | 40 | 60 | 72 | 81 | 88 |
| | 2.1 | −3.6 | 7.4 | 16 | 26 | 38 | 52 | 70 | 80 | 88 |
| | 4.2 | −2.1 | 24 | 25 | 35 | 45 | 60 | 76 | 81 | 91 |
| | 8.3 | 0.33 | 17 | 32 | 39 | 55 | 67 | 75 | 82 | 89 |
| | 17 | 12 | 22 | 27 | 42 | 63 | 70 | 81 | 86 | 89 |
| | 33 | 88 | 86 | 87 | 91 | 90 | 93 | 94 | 95 | 96 |
| | 67 | 92 | 94 | 95 | 95 | 94 | 94 | 89 | 92 | 89 |

TABLE 31

| | | \multicolumn{9}{c}{Dipyridamole (μM)} |
|---|---|---|---|---|---|---|---|---|---|---|
| | | 0 | 0.3 | 0.61 | 1.2 | 2.4 | 4.9 | 9.7 | 19 | 39 |
| Paroxetine (μM) | 0 | 5.5 | 14 | 15 | 16 | 28 | 51 | 64 | 77 | 85 |
| | 0.21 | −7.2 | 7 | 2.6 | 5.6 | 28 | 49 | 63 | 76 | 86 |
| | 0.42 | −5.6 | 8.9 | −1.1 | 10 | 30 | 54 | 68 | 78 | 86 |
| | 0.83 | −8.7 | 13 | 8.2 | 13 | 26 | 43 | 65 | 77 | 86 |
| | 1.7 | −10 | 5.1 | 4.3 | 18 | 26 | 49 | 74 | 79 | 86 |
| | 3.3 | −11 | 1.8 | 18 | 9 | 22 | 59 | 70 | 78 | 87 |
| | 6.7 | −15 | −9.8 | −4.8 | 20 | 28 | 54 | 72 | 80 | 87 |
| | 13 | 9.9 | 0.92 | 37 | 31 | 48 | 71 | 79 | 88 | 93 |
| | 27 | 73 | 81 | 81 | 81 | 69 | 87 | 87 | 86 | 93 |

TABLE 32

| | | \multicolumn{8}{c}{Ibutilast (μM)} |
|---|---|---|---|---|---|---|---|---|---|
| | | 0 | 0.062 | 0.12 | 0.25 | 0.5 | 1 | 2 | 4 | 8 |
| Dipyridamole (μM) | 0 | −12.66 | 15.85 | 22.9 | 34.3 | 43.8 | 62.25 | 76.65 | 85.05 | 89.72 |
| | 0.15 | 0 | 22.93 | 34.02 | 39.45 | 60.8 | 69.9 | 81.38 | 86.2 | 89.3 |
| | 0.3 | 5.46 | 25.31 | 36.33 | 47.53 | 63.88 | 74 | 81.57 | 88.95 | 90.55 |
| | 0.61 | 15.74 | 29.33 | 41.7 | 50.25 | 61.58 | 73.65 | 80.1 | 88.97 | 90.62 |
| | 1.2 | 21.24 | 32.42 | 43.12 | 57.6 | 66.33 | 76.25 | 81.05 | 86.95 | 90.35 |
| | 2.4 | 39.73 | 48.55 | 49.2 | 58.87 | 72.12 | 76 | 82.7 | 86.97 | 89.77 |
| | 4.9 | 49.8 | 58.62 | 65.52 | 68.47 | 73.67 | 77.75 | 84.15 | 87.73 | 90.1 |
| | 9.7 | 72.85 | 73.9 | 74.15 | 78.97 | 80.53 | 84.4 | 86.28 | 89.1 | 91.5 |
| | 19 | 84.25 | 84.18 | 84.82 | 86.55 | 86.88 | 88.55 | 89.72 | 90.93 | 92.78 |

TABLE 33

| | | \multicolumn{9}{c}{Dipyridamole (µM)} |
|---|---|---|---|---|---|---|---|---|---|---|
| | | 0 | 0.15 | 0.3 | 0.61 | 1.2 | 2.4 | 4.9 | 9.7 | 19 |
| Ro-20-1724 (µM) | 0 | −8.74 | −2.06 | 0.185 | −0.311 | 7.645 | 21.62 | 44.48 | 62.68 | 79.38 |
| | 0.28 | 12.69 | 17.95 | 19.85 | 28.27 | 32.58 | 52.27 | 62.85 | 74.7 | 80.5 |
| | 0.56 | 28.12 | 37.1 | 42.05 | 44.2 | 48.32 | 54.8 | 68.42 | 77.97 | 83.3 |
| | 1.1 | 39.03 | 45.33 | 49.52 | 48.55 | 51.73 | 60.15 | 70.17 | 79.85 | 84.7 |
| | 2.2 | 50.03 | 60.97 | 59.82 | 62.88 | 65.7 | 69.38 | 75.33 | 80.1 | 87 |
| | 4.5 | 66.55 | 68.12 | 69.45 | 71.75 | 74.47 | 74.97 | 77.5 | 82.5 | 85.52 |
| | 9 | 76.92 | 79.33 | 80.17 | 82.4 | 82.05 | 83.3 | 82.7 | 86.62 | 88.9 |
| | 18 | 84.53 | 85.8 | 84.53 | 85.95 | 86.97 | 86.3 | 85.7 | 87.65 | 89.9 |
| | 36 | 88.12 | 88.62 | 88.42 | 89.15 | 89.32 | 88.83 | 89.28 | 90.28 | 92.08 |

TABLE 34

| | | \multicolumn{9}{c}{Rolipram (µM)} |
|---|---|---|---|---|---|---|---|---|---|---|
| | | 0 | 0.0079 | 0.016 | 0.031 | 0.063 | 0.13 | 0.25 | 0.5 | 1 |
| Dipyridamole (µM) | 0 | −9.488 | 17.95 | 19.02 | 17.96 | 32.25 | 45.75 | 60.2 | 69.88 | 80.17 |
| | 0.15 | −0.48 | 18.12 | 29.65 | 31.27 | 44.05 | 59.45 | 67.75 | 76.55 | 84.53 |
| | 0.3 | 4.848 | 26.65 | 34.38 | 45.78 | 49.67 | 63.6 | 71.08 | 80.5 | 84.78 |
| | 0.61 | 14.37 | 27.93 | 41.5 | 46.93 | 52.3 | 63.85 | 72.1 | 83.25 | 85.97 |
| | 1.2 | 25.8 | 49.02 | 48.07 | 53.95 | 62.55 | 67.6 | 75.28 | 82.97 | 87.2 |
| | 2.4 | 44.1 | 54.55 | 56.5 | 65.1 | 70.2 | 72.62 | 78.95 | 82.73 | 87.53 |
| | 4.9 | 62.2 | 69.33 | 69.92 | 75.12 | 77.67 | 80.9 | 82.65 | 86.02 | 89.18 |
| | 9.7 | 77.95 | 78.88 | 79.2 | 81.8 | 82.97 | 85 | 86.95 | 87.53 | 89.52 |
| | 19 | 86.9 | 85.63 | 85.9 | 87.57 | 87.5 | 88.75 | 89.1 | 90.3 | 91.23 |

TABLE 35

| | | \multicolumn{9}{c}{Dipyridamole (µM)} |
|---|---|---|---|---|---|---|---|---|---|---|
| | | 0 | 0.15 | 0.3 | 0.61 | 1.2 | 2.4 | 4.9 | 9.7 | 19 |
| Bromodiphenhydramine HCl (µM) | 0 | −2.4 | 5 | 21 | 32 | 38 | 63 | 76 | 85 | 90 |
| | 0.21 | 5.5 | 9 | 20 | 25 | 47 | 61 | 77 | 86 | 90 |
| | 0.43 | −0.69 | 5.2 | 25 | 27 | 49 | 60 | 76 | 85 | 89 |
| | 0.85 | −8.2 | 4.1 | 16 | 21 | 40 | 60 | 76 | 85 | 89 |
| | 1.7 | −20 | −8.6 | 0.15 | 4.3 | 42 | 57 | 72 | 81 | 90 |
| | 3.4 | −20 | −13 | 1 | −2.3 | 32 | 55 | 76 | 83 | 89 |
| | 6.8 | −20 | −20 | −6.5 | −1.3 | 30 | 58 | 72 | 84 | 90 |
| | 14 | −20 | −20 | −20 | 0.04 | 22 | 51 | 74 | 85 | 90 |
| | 27 | −20 | −9.1 | −9.1 | −8.4 | 28 | 53 | 66 | 79 | 89 |

TABLE 36

| | | \multicolumn{9}{c}{Dipyridamole (µM)} |
|---|---|---|---|---|---|---|---|---|---|---|
| | | 0 | 0.15 | 0.3 | 0.61 | 1.2 | 2.4 | 4.9 | 9.7 | 19 |
| Cyproheptadine HCl (µM) | 0 | −16 | 7.5 | 11 | 25 | 37 | 49 | 66 | 77 | 80 |
| | 0.24 | −10 | 15 | 19 | 29 | 28 | 52 | 63 | 76 | 79 |
| | 0.48 | −8.2 | 3.7 | 4.8 | 23 | 22 | 46 | 61 | 70 | 80 |
| | 0.96 | −4.5 | −5.6 | 12 | 32 | 29 | 57 | 65 | 78 | 81 |
| | 1.9 | −7.2 | −4.5 | 3.2 | 19 | 26 | 52 | 62 | 72 | 81 |
| | 3.9 | −3.3 | −5.5 | 23 | 21 | 28 | 51 | 64 | 72 | 80 |
| | 7.7 | −16 | −0.26 | 14 | 20 | 41 | 56 | 68 | 70 | 79 |
| | 15 | −18 | −3.7 | 23 | 16 | 39 | 50 | 63 | 67 | 72 |
| | 31 | −0.89 | 12 | 23 | 21 | 37 | 39 | 58 | 63 | 72 |

TABLE 37

| | | \multicolumn{9}{c}{Dipyridamole (µM)} |
|---|---|---|---|---|---|---|---|---|---|---|
| | | 0 | 0.15 | 0.3 | 0.61 | 1.2 | 2.4 | 4.9 | 9.7 | 19 |
| Loratadine (µM) | 0 | −3.4 | 8 | 22 | 26 | 49 | 59 | 71 | 77 | 86 |
| | 0.2 | −8 | 7.1 | 29 | 32 | 42 | 50 | 70 | 77 | 84 |
| | 0.41 | −4.7 | 10 | 15 | 27 | 38 | 51 | 68 | 79 | 85 |
| | 0.82 | −6.9 | 9.3 | 12 | 19 | 39 | 62 | 65 | 78 | 86 |
| | 1.6 | −10 | 1.7 | 14 | 22 | 40 | 49 | 71 | 76 | 85 |
| | 3.3 | −15 | 7.1 | 14 | 29 | 43 | 54 | 67 | 78 | 84 |
| | 6.5 | −20 | 0.41 | 24 | 22 | 36 | 52 | 66 | 76 | 84 |
| | 13 | −20 | 1 | 12 | 14 | 42 | 59 | 68 | 80 | 86 |
| | 26 | −4.7 | 1.7 | 24 | 22 | 34 | 53 | 61 | 75 | 82 |

TABLE 38

| | | \multicolumn{9}{c}{Dipyridamole (μM)} | | | | | | | | |
|---|---|---|---|---|---|---|---|---|---|---|
| | | 0 | 0.15 | 0.3 | 0.61 | 1.2 | 2.4 | 4.9 | 9.7 | 19 |
| Thiethyl-perazine maleate (μM) | 0 | −0.7 | 8 | 22 | 34 | 52 | 60 | 72 | 80 | 86 |
| | 0.2 | −8.3 | 5.3 | 21 | 32 | 40 | 58 | 71 | 76 | 85 |
| | 0.39 | −9.7 | −8.4 | 17 | 28 | 39 | 56 | 69 | 77 | 87 |
| | 0.78 | −11 | −4.2 | 20 | 17 | 31 | 54 | 67 | 76 | 85 |
| | 1.6 | −18 | −8.4 | 5.9 | 11 | 36 | 51 | 72 | 76 | 84 |
| | 3.1 | −18 | −10 | 8.1 | 15 | 40 | 55 | 69 | 78 | 81 |
| | 6.3 | −20 | −18 | −7.2 | 7 | 30 | 50 | 64 | 77 | 83 |
| | 13 | −20 | −20 | −18 | 5.7 | 16 | 37 | 60 | 65 | 78 |
| | 25 | −16 | −20 | −1.9 | 10 | 23 | 34 | 54 | 69 | 74 |

The ability of various combinations to suppress IL-2 secretion in vitro was also tested. The results are shown in tables 39 to 47.

TABLE 39

| | | \multicolumn{9}{c}{Prednisolone (μM)} | | | | | | | | |
|---|---|---|---|---|---|---|---|---|---|---|
| | | 0 | 0.0078 | 0.016 | 0.031 | 0.062 | 0.12 | 0.25 | 0.5 | 1 |
| Dipyridamole (μM) | 0 | 1.99 | −3 | −4.03 | −1.64 | −2.42 | −1.86 | −1.08 | −3.96 | 3.43 |
| | 0.3 | 3.22 | — | −8.71 | 3.29 | −0.761 | 1.52 | −0.414 | 3.47 | 5.24 |
| | 0.61 | 2.96 | 4.99 | −6.52 | 1.17 | 3.19 | −0.735 | −6.22 | −3 | 5.75 |
| | 1.2 | 3.94 | −0.287 | −2.22 | 3.03 | −3.51 | −4.7 | 1.35 | 2.43 | 12.1 |
| | 2.4 | 4.37 | −0.595 | 2.59 | −3.44 | −1.92 | −4.09 | 4.07 | 3.68 | 12.3 |
| | 4.9 | 3.32 | 0.363 | −5.51 | −2.89 | 0.346 | −1.24 | 2.44 | 1.84 | 12.6 |
| | 9.7 | 7.5 | 4.26 | −4.75 | 3.85 | −1.93 | 5.08 | −0.524 | 4.28 | 13.9 |
| | 19 | −2.75 | −3.19 | −3.78 | −1.45 | −5.31 | 4.49 | 0.283 | 7.98 | 4.89 |
| | 39 | −2.67 | 4.48 | −0.324 | 4.71 | 8.29 | 7.7 | −1.27 | 7.61 | 13.3 |

TABLE 40

| | | \multicolumn{8}{c}{Dipyridamole (μM)} | | | | | | | |
|---|---|---|---|---|---|---|---|---|---|
| | | 0 | 0.3 | 0.61 | 1.2 | 2.4 | 4.9 | 9.7 | 19 | 39 |
| Amoxapine (μM) | 0 | −2.4 | −18 | −12 | −17 | −14 | −11 | −3.9 | −7.3 | −8.8 |
| | 0.25 | −17 | −13 | −8.1 | −12 | −13 | −7.1 | −7.9 | −4.4 | −1.2 |
| | 0.5 | −15 | −12 | −14 | −19 | 1.4 | −3.4 | −7.4 | −5.8 | 8.5 |
| | 1 | −3.1 | −13 | −6.6 | −14 | −13 | −0.16 | −0.39 | 2.5 | 23 |
| | 2 | −0.082 | −9.6 | −0.51 | −8.2 | −7.4 | −0.06 | 15 | 18 | 43 |
| | 4 | 1.5 | 12 | 10 | 11 | 17 | 17 | 28 | 36 | 70 |
| | 8 | 55 | 38 | 40 | 45 | 58 | 56 | 72 | 77 | 89 |
| | 16 | 83 | 78 | 78 | 81 | 87 | 89 | 91 | 92 | 93 |
| | 32 | 93 | 90 | 94 | 95 | 95 | 95 | 95 | 91 | 94 |

TABLE 41

| | | \multicolumn{8}{c}{Dipyridamole (μM)} | | | | | | | |
|---|---|---|---|---|---|---|---|---|---|
| | | 0 | 0.3 | 0.61 | 1.2 | 2.4 | 4.9 | 9.7 | 19 | 39 |
| Fluoxetine hydrochloride (μM) | 0 | 6 | −6.9 | −10 | −15 | −5.2 | −5.2 | — | 9.3 | 9.8 |
| | 0.45 | −13 | −12 | −10 | −9.6 | −4.5 | −11 | 0.86 | 7.6 | 10 |
| | 0.9 | −6.2 | −11 | −14 | −19 | −2 | −4.5 | −1 | 4.7 | 9.7 |
| | 1.8 | −8.1 | −12 | −4.8 | −14 | −16 | 3.9 | 4.4 | 12 | 22 |
| | 3.6 | −13 | −3.1 | −5.2 | −7.1 | −7.2 | 1.3 | 4.6 | 25 | 40 |
| | 7.2 | 8.3 | 12 | 14 | 12 | 17 | 26 | 31 | 45 | 57 |
| | 14 | 58 | 62 | 62 | 60 | 74 | 69 | 82 | 81 | 87 |
| | 29 | 93 | 92 | 92 | 93 | 92 | 94 | 95 | 96 | 96 |
| | 58 | 97 | 98 | 98 | 98 | 98 | 98 | 98 | 98 | 97 |

TABLE 42

| | | \multicolumn{8}{c}{Dipyridamole (μM)} | | | | | | | |
|---|---|---|---|---|---|---|---|---|---|
| | | 0 | 0.3 | 0.61 | 1.2 | 2.4 | 4.9 | 9.7 | 19 | 39 |
| Nortriptyline hydrochloride (μM) | 0 | −0.24 | 5.8 | 3.4 | −1.7 | 3.2 | 1.8 | 0.7 | 14 | 9.1 |
| | 0.52 | 9.2 | 5.2 | 7 | 5.8 | 6.2 | 2.3 | 6.8 | 18 | 16 |
| | 1 | 12 | 7.6 | 4.7 | −4.1 | 1.6 | 6.7 | 4.1 | 13 | 15 |
| | 2.1 | 7.8 | 19 | 10 | −2.4 | 8.9 | 16 | 12 | 20 | 26 |
| | 4.2 | 14 | 17 | 11 | 6.7 | 10 | 14 | 39 | 35 | 56 |
| | 8.3 | 38 | 32 | 50 | 45 | 42 | 45 | 62 | 69 | 79 |

TABLE 42-continued

| | Dipyridamole (µM) | | | | | | | | |
|---|---|---|---|---|---|---|---|---|---|
| | 0 | 0.3 | 0.61 | 1.2 | 2.4 | 4.9 | 9.7 | 19 | 39 |
| 17 | 76 | 79 | 78 | 77 | 83 | 84 | 88 | 88 | 92 |
| 33 | 83 | 90 | 89 | 91 | 91 | 83 | 92 | 91 | 89 |
| 67 | 88 | 93 | 91 | 94 | 86 | 93 | 93 | 91 | 90 |

TABLE 43

| | | Dipyridamole (µM) | | | | | | | | |
|---|---|---|---|---|---|---|---|---|---|---|
| | | 0 | 0.3 | 0.61 | 1.2 | 2.4 | 4.9 | 9.7 | 19 | 39 |
| Paroxetine (µM) | 0 | −2 | 9.1 | 11 | 4.7 | 14 | 0.58 | 20 | 20 | 24 |
| | 0.21 | 11 | 16 | −2.5 | 6.1 | 16 | 24 | 18 | 25 | 22 |
| | 0.42 | 4.5 | 16 | 8.7 | −0.05 | −0.2 | 33 | 20 | 26 | 23 |
| | 0.83 | 5.9 | 12 | 6.6 | 2.2 | 13 | 18 | 22 | 24 | 29 |
| | 1.7 | −3 | 18 | −0.65 | −14 | 19 | 20 | 26 | 24 | 30 |

TABLE 43-continued

| | Dipyridamole (µM) | | | | | | | | |
|---|---|---|---|---|---|---|---|---|---|
| | 0 | 0.3 | 0.61 | 1.2 | 2.4 | 4.9 | 9.7 | 19 | 39 |
| 3.3 | 21 | 24 | 2.7 | 9.3 | 28 | 36 | 39 | 49 | 51 |
| 6.7 | 4.3 | 61 | 56 | 57 | 70 | 65 | 72 | 42 | 78 |
| 13 | 88 | 84 | 89 | 90 | 91 | 92 | 92 | 93 | 92 |
| 27 | 93 | 95 | 95 | 95 | 94 | 95 | 93 | 96 | 90 |

TABLE 44

| | | Dipyridamole (µM) | | | | | | | |
|---|---|---|---|---|---|---|---|---|---|
| | | 0 | 0.15 | 0.3 | 0.61 | 1.2 | 2.4 | 4.9 | 9.7 | 19 |
| Bromodiphenhydramine HCl (µM) | 0 | −5 | −6.1 | −11 | 0.66 | 4.6 | −4.1 | −3.5 | 8.8 | −6.8 |
| | 0.21 | 6.1 | −1.7 | −4.3 | 2.1 | −1.9 | −13 | −7.4 | 3.5 | −3.5 |
| | 0.43 | −0.38 | 0.68 | −2.3 | −5.1 | −12 | −6.8 | −1.5 | −17 | −0.75 |
| | 0.85 | −4.5 | −9.5 | −7.3 | −12 | −7.9 | −14 | 3.5 | −5.3 | 15 |
| | 1.7 | 3 | −6.8 | −14 | −17 | −16 | 2.1 | 3.1 | 0.065 | 3.5 |
| | 3.4 | 4 | 3.7 | −20 | −13 | −7.3 | −1.8 | −11 | −0.98 | 16 |
| | 6.8 | 6.3 | 6.6 | −3.5 | −9.8 | −7.1 | 1.6 | −0.43 | 2.5 | 16 |
| | 14 | 10 | 6.3 | 5.8 | −15 | 12 | 14 | 4.6 | 12 | 13 |
| | 27 | 25 | 22 | 55 | 45 | 34 | 27 | 33 | 33 | 37 |

TABLE 45

| | | Dipyridamole (µM) | | | | | | | |
|---|---|---|---|---|---|---|---|---|---|
| | | 0 | 0.15 | 0.3 | 0.61 | 1.2 | 2.4 | 4.9 | 9.7 | 19 |
| Cyproheptadine HCl (µM) | 0 | −6 | 5.2 | −7.2 | 1.4 | −2.6 | −2.4 | 0.58 | 13 | −5.3 |
| | 0.24 | 8.6 | −4.8 | 9.3 | 3.1 | −15 | 1.1 | 2.1 | 1.7 | −17 |
| | 0.48 | 8.4 | 7.2 | 9.5 | −1.8 | −12 | −14 | −1.6 | −5.9 | 5.2 |
| | 0.96 | 1.1 | 7.2 | −0.95 | −1 | −3.8 | −7.2 | 4.2 | 0.27 | −0.7 |
| | 1.9 | 4.7 | 3.9 | −1.2 | 2.2 | 9.2 | 0.31 | −1 | −6.2 | −3.7 |
| | 3.9 | 6.4 | 15 | 2.2 | 8.8 | −7.5 | −1.5 | 11 | 8.2 | 14 |
| | 7.7 | 27 | 23 | 5.5 | 4 | 17 | 16 | 0.35 | 1.3 | 14 |
| | 15 | 31 | 36 | 31 | 41 | 33 | 28 | 26 | 36 | 29 |
| | 31 | 24 | 29 | 17 | 2.4 | −4.2 | 44 | 35 | 29 | 31 |

TABLE 46

| | | Dipyridamole (µM) | | | | | | | |
|---|---|---|---|---|---|---|---|---|---|
| | | 0 | 0.15 | 0.3 | 0.61 | 1.2 | 2.4 | 4.9 | 9.7 | 19 |
| Loratadine (µM) | 0 | −6.7 | 4.9 | −9 | −15 | −5.1 | −14 | −5.2 | −5.4 | 3.8 |
| | 0.2 | 1.6 | −4.5 | −2 | 3.3 | −14 | −9.5 | 7.8 | −1.6 | −7.8 |
| | 0.41 | −1.1 | −1.8 | −2.6 | −12 | −4.6 | −12 | −4.8 | −7.4 | 9 |
| | 0.82 | −10 | −9 | −8.2 | −12 | −7.8 | −12 | −8.8 | −16 | −7.9 |
| | 1.6 | −5.6 | −4.8 | −12 | −14 | −19 | −11 | −10 | −9.8 | 13 |
| | 3.3 | −0.54 | 0.04 | −13 | −18 | −15 | −12 | −12 | −20 | 0.6 |
| | 6.5 | −1.4 | −11 | −6.8 | −8.4 | 1.9 | −1.2 | 1.3 | 4.4 | 8.5 |
| | 13 | −13 | 5.9 | 0.15 | −9.9 | −15 | 3.9 | −5.5 | 2.6 | 6.1 |
| | 26 | 16 | 5.9 | −11 | −20 | 11 | 15 | 15 | 4.9 | 2.8 |

TABLE 47

| | | \multicolumn{9}{c}{Dipyridamole (μM)} | | | | | | | | |
|---|---|---|---|---|---|---|---|---|---|---|
| | | 0 | 0.15 | 0.3 | 0.61 | 1.2 | 2.4 | 4.9 | 9.7 | 19 |
| Thiethylperazine maleate (μM) | 0 | 5 | -1.9 | -11 | -8.2 | 1.3 | -10 | -0.47 | -20 | -11 |
| | 0.2 | -10 | 2.6 | -9.6 | -9.9 | -3.8 | 8.2 | -8.5 | -11 | -17 |
| | 0.39 | -7.9 | -15 | -16 | 12 | 6.8 | -4 | -12 | -6.7 | -11 |
| | 0.78 | -17 | -8.4 | -4.7 | -7.3 | -8.3 | -5.5 | -18 | -6.2 | -2.9 |
| | 1.6 | -7 | -11 | -15 | -19 | -7.3 | -10 | -20 | -17 | 2.5 |
| | 3.1 | -19 | -7.8 | -7.6 | -17 | -12 | -4.2 | -7.5 | -5.5 | 4.1 |
| | 6.3 | 3.1 | -20 | -10 | -3.5 | -18 | -15 | -7 | -15 | 12 |
| | 13 | 6 | 4.6 | 11 | 0.53 | 22 | 11 | 21 | 30 | 36 |
| | 25 | -15 | 28 | 22 | 23 | 62 | 67 | 58 | 63 | 72 |

The ability of various combinations to suppress IL-1 secretion in vitro was also tested. The results are shown in Tables 48 to 52.

TABLE 48

| | | \multicolumn{9}{c}{Prednisolone (μM)} | | | | | | | | |
|---|---|---|---|---|---|---|---|---|---|---|
| | | 0 | 0.0078 | 0.016 | 0.031 | 0.062 | 0.12 | 0.25 | 0.5 | 1 |
| Dipyridamole (μM) | 0 | -8.25 | 6.42 | -5.05 | 1.3 | 13.2 | 36 | 52.4 | 61.5 | 68.8 |
| | 0.3 | 3.78 | -7.41 | 3.45 | 11.8 | 4.78 | 42.5 | 56 | 59.6 | 66.5 |
| | 0.61 | -5.65 | 8.23 | 10.1 | 14 | 31.2 | 50.5 | 46.5 | 59.7 | 69 |
| | 1.2 | 10 | 14.9 | 19.2 | 24.2 | 26.3 | 46.9 | 54.5 | 59.8 | 65.9 |
| | 2.4 | 18.5 | 30.8 | 29 | 43.4 | 44.7 | 55.4 | 62.7 | 56.6 | 75.2 |
| | 4.9 | 29.3 | 31.1 | 31.7 | 39.9 | 43.1 | 54.9 | 57.1 | 66.2 | 64.9 |
| | 9.7 | 35.8 | 34.4 | 39.1 | 41.4 | 51.4 | 53.4 | 63.8 | 63.8 | 75.3 |
| | 19 | 46.3 | 44.8 | 47 | 49 | 60.5 | 64 | 61.6 | 71 | 71.7 |
| | 39 | 55.3 | 53.7 | 55.4 | 56.7 | 56.3 | 55.2 | 68.5 | 73.4 | 75.6 |

TABLE 49

| | | \multicolumn{8}{c}{Dipyridamole (μM)} | | | | | | | |
|---|---|---|---|---|---|---|---|---|---|
| | | 0 | 0.3 | 0.61 | 1.2 | 2.4 | 4.9 | 9.7 | 19 | 39 |
| Amoxapine (μM) | 0 | 12 | -1.6 | 0.15 | -16 | -5.5 | 13 | 36 | 35 | 42 |
| | 0.25 | 5.5 | 0.99 | -6.7 | -5.2 | -4.2 | 18 | 37 | 34 | 39 |
| | 0.5 | 6.3 | -7 | -8.6 | -11 | 3.5 | 18 | 25 | 37 | 52 |
| | 1 | 1.1 | -8.7 | -14 | -0.65 | 11 | 18 | 34 | 44 | 49 |
| | 2 | 4.6 | 5.2 | 3.8 | -1.8 | 12 | 22 | 37 | 48 | 42 |
| | 4 | 10 | 15 | -4.9 | 11 | 14 | 17 | 36 | 37 | 37 |
| | 8 | 3.1 | 9.2 | 3.3 | 8.6 | 16 | 18 | 31 | 28 | 19 |
| | 16 | 17 | 25 | 17 | 27 | 18 | 8.8 | -3.7 | -0.71 | -1.4 |
| | 32 | 30 | 7 | 10 | 18 | 13 | -0.7 | 16 | 21 | 35 |

TABLE 50

| | | \multicolumn{8}{c}{Dipyridamole (μM)} | | | | | | | |
|---|---|---|---|---|---|---|---|---|---|
| | | 0 | 0.3 | 0.61 | 1.2 | 2.4 | 4.9 | 9.7 | 19 | 39 |
| Fluoxetine HCl (μM) | 0 | 28 | -3 | -14 | 5.7 | -8.9 | 14 | 44 | 55 | 64 |
| | 0.45 | 7.5 | -20 | -20 | -8.1 | 14 | 30 | 23 | 56 | 56 |
| | 0.9 | 9.9 | 26 | 3.2 | -2.5 | -3.5 | 19 | 34 | 52 | 61 |
| | 1.8 | -19 | 0.79 | -7.3 | 24 | 13 | 8.6 | 33 | 51 | 63 |
| | 3.6 | -5.8 | 1.6 | 17 | 32 | 23 | 35 | 41 | 59 | 54 |
| | 7.2 | 13 | 21 | -0.1 | 22 | 23 | 35 | 48 | 56 | 45 |
| | 14 | -0.095 | 27 | 29 | 14 | 22 | 14 | 6.5 | 6.6 | 13 |
| | 29 | 48 | 36 | 34 | 42 | 35 | 50 | 44 | 46 | 60 |
| | 58 | 63 | 74 | 65 | 59 | 71 | 63 | 71 | 81 | 83 |

TABLE 51

| | | \multicolumn{9}{c}{Dipyridamole (μM)} | | | | | | | | |
|---|---|---|---|---|---|---|---|---|---|---|
| | | 0 | 0.3 | 0.61 | 1.2 | 2.4 | 4.9 | 9.7 | 19 | 39 |
| Nortriptyline HCl (μM) | 0 | 45 | −5.9 | −8.8 | −1.3 | 8.4 | 22 | 35 | 51 | 56 |
| | 0.52 | −13 | −17 | −17 | −4.7 | −0.34 | 23 | 33 | 54 | 55 |
| | 1 | −16 | −6.9 | −12 | −2.6 | 19 | 22 | 36 | 48 | 51 |
| | 2.1 | −17 | −16 | −17 | −2.9 | −0.41 | 17 | 33 | 47 | 50 |
| | 4.2 | −14 | −12 | −12 | 0.11 | 3.9 | 27 | 42 | 47 | 42 |
| | 8.3 | −8.8 | −10 | −1.8 | −0.97 | 13 | 13 | 26 | 19 | 23 |
| | 17 | 11 | −4.8 | −7.5 | 2.9 | 12 | 25 | 10 | 9 | 11 |
| | 33 | 40 | 38 | 34 | 40 | 42 | 56 | 52 | 57 | 73 |
| | 67 | 61 | 74 | 65 | 71 | 73 | 72 | 70 | 79 | 78 |

TABLE 52

| | | \multicolumn{9}{c}{Dipyridamole (μM)} | | | | | | | | |
|---|---|---|---|---|---|---|---|---|---|---|
| | | 0 | 0.3 | 0.61 | 1.2 | 2.4 | 4.9 | 9.7 | 19 | 39 |
| Paroxetine HCl (μM) | 0 | 39 | 6.2 | −15 | −9.5 | −7.3 | 23 | 31 | 47 | 35 |
| | 0.21 | −13 | −10 | −3.5 | −7.6 | −1.8 | 20 | 29 | 39 | 51 |
| | 0.42 | −20 | 9 | 14 | 26 | 20 | 12 | 44 | 46 | 54 |
| | 0.83 | −12 | −7.7 | −7.8 | 10 | 2.4 | 33 | 32 | 36 | 58 |
| | 1.7 | −7.9 | −5.5 | −14 | −2.5 | 21 | 44 | 47 | 56 | 68 |
| | 3.3 | −1.8 | 1.9 | −11 | −15 | 21 | 30 | 50 | 50 | 54 |
| | 6.7 | −14 | −2.6 | 0.8 | 13 | 19 | 4.4 | 27 | 37 | 5.5 |
| | 13 | 31 | 21 | 25 | 32 | 17 | 6 | 16 | 20 | 4 |
| | 27 | 42 | 45 | 45 | 57 | 45 | 53 | 50 | 62 | 58 |

The ability of the combination of prednisolone and dipyridamole to suppress IFN-γ secretion in vitro was also tested. The results are shown in Table 53.

TABLE 53

| | | \multicolumn{9}{c}{Prednisolone (μM)} | | | | | | | | |
|---|---|---|---|---|---|---|---|---|---|---|
| | | 0 | 0.0039 | 0.0078 | 0.016 | 0.031 | 0.062 | 0.12 | 0.25 | 0.5 |
| Dipyridamole (μM) | 0 | 2.41 | 2.85 | 2.65 | 7.72 | 9.9 | 11.8 | 16.4 | 14.4 | 14.8 |
| | 0.15 | −2.89 | 0.45 | 2.25 | −0.151 | 8.81 | 8.41 | 11.8 | 10.4 | 12.4 |
| | 0.3 | −4.9 | −1.7 | 0.543 | 5.36 | 6.42 | 8.75 | 11.5 | 13.9 | 16.2 |
| | 0.61 | −2.5 | −3.96 | 1.24 | 3.85 | 3.81 | 7.13 | 5.03 | 10.2 | 12.1 |
| | 1.2 | −5.45 | −3.47 | −6.18 | 1.66 | 6.21 | 10.2 | 5.27 | 9.36 | 15.5 |
| | 2.4 | −0.679 | −8.62 | −0.23 | 1.97 | 5.66 | 5.26 | 13.6 | 11.2 | 13.8 |
| | 4.9 | −1.31 | −0.765 | 7.49 | 6.78 | 8.58 | 15.6 | 16.9 | 21.2 | 23.1 |
| | 9.7 | 13.3 | 11.1 | 14.5 | 19.8 | 19.9 | 25.7 | 26.2 | 31.1 | 30.8 |
| | 19 | 16.3 | 18 | 17.5 | 21.9 | 30.2 | 35 | 37.6 | 37.7 | 39.3 |

Other Embodiments

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification are herein incorporated by reference to the same extent as if each independent publication was specifically and individually incorporated by reference.

What is claimed is:

1. A method for treating a patient who has osteoarthritis, said method consisting essentially of administering to said patient:
   (a) a corticosteroid; and
   (b) dipyridamole wherein said compound wherein said dipyridamole and said corticosteroid are administered simultaneously or within 14 days of each other, in amounts and for a duration sufficient to treat said patient.

2. The method of claim 1, wherein said corticosteroid is 11-alpha,17-alpha,21-trihydroxypregn-4-ene-3,20-dione; 11-beta,16-alpha,17,21-tetrahydroxypregn-4-ene-3,20-dione; 11-beta,16-alpha,17,21-tetrahydroxypregn-1,4-diene-3,20-dione; 11-beta,17-alpha,21-trihydroxy-6-alpha-methyl-pregn-4-ene-3,20-dione; 11-dehydrocorticosterone; 11-deoxycortisol; 11-hydroxy-1,4-androstadiene-3,17-dione; 11-ketotestosterone; 14-hydroxyandrost-4-ene-3,6,17-trione; 15,17-dihydroxyprogesterone; 16-methylhydrocortisone; 17,21-dihydroxy-16-alpha-methylpregna-1,4,9(11)- triene-3,20-dione; 17-alpha-hydroxypregn-4-ene-3,20-dione; 17-alpha-hydroxypregnenolone; 17-hydroxy-16-beta-methyl-5-beta-pregn-9(11)-ene-3,20-dione; 17-hydroxy-4,6,8(14)-pregnatriene-3,20-dione; 17-hydroxypregna-4,9(11)-diene-3,20-dione; 18-hydroxycorticosterone; 18-hydroxycortisone; 18-oxocortisol; 21-deoxyaldosterone; 21-deoxycortisone; 2-deoxyecdysone; 2-methylcortisone; 3-dehydroecdysone; 4-pregnene-17-alpha,20-beta, 21-triol-3,11-dione; 6,17,20-trihydroxypregn-4-ene-3-one; 6-alpha-hydroxycortisol; 6-alpha-fluoroprednisolone, 6-alpha-methylprednisolone, 6-alpha-methylprednisolone 21-acetate, 6-alpha-methylprednisolone 21-hemisuccinate sodium salt, 6-beta-hydroxycortisol, 6-alpha, 9-alpha-difluoroprednisolone 21-acetate 17-butyrate, 6-hydroxycorticosterone; 6-hydroxydexamethasone; 6-hydroxyprednisolone; 9-fluorocortisone; alclometasone dipropionate; aldosterone; algestone; alphaderm; amadinone; amcinonide; anagestone; androstenedione; anecortave acetate; beclomethasone; beclomethasone dipropionate; beclomethasone dipropionate monohydrate; betamethasone 17-valerate; betamethasone sodium acetate; betamethasone sodium phosphate; betamethasone valerate; bolasterone; budesonide; calusterone; chlormadinone; chloroprednisone; chloroprednisone acetate; cholesterol; clobetasol; clobetasol propionate; clobetasone; clocortolone; clocortolone pivalate; clogestone; cloprednol; corticosterone; cortisol; cortisol acetate; cortisol butyrate; cortisol cypionate; cortisol octanoate; cortisol sodium phosphate; cortisol sodium succinate; cortisol valerate; cortisone; cortisone acetate; cortodoxone; daturaolone; deflazacort, 21-deoxycortisol, dehydroepiandrosterone; delmadinone; deoxycorticosterone; deprodone; descinolone; desonide; desoximethasone; dexafen; dexamethasone; dexamethasone 21-acetate; dexamethasone acetate; dexamethasone sodium phosphate; dichlorisone; diflorasone; diflorasone diacetate; diflucortolone; dihydroelatericin a; domoprednate; doxibetasol; ecdysone; ecdysterone; endrysone; enoxolone; flucinolone; fludrocortisone; fludrocortisone acetate; flugestone; flumethasone; flumethasone pivalate; flumoxonide; flunisolide; fluocinolone; fluocinolone acetonide; fluocinonide; 9-fluorocortisone; fluocortolone; fluorohydroxyandrostenedione; fluorometholone; fluorometholone acetate; fluoxymesterone; fluprednidene; fluprednisolone; flurandrenolide; fluticasone; fluticasone propionate; formebolone; formestane; formocortal; gestonorone; glyderinine; halcinonide; hyrcanoside; halometasone; halopredone; haloprogesterone; hydrocortisone; hydrocortisone 21-butyrate; hydrocortisone aceponate; hydrocortisone acetate; hydrocortisone buteprate; hydrocortisone butyrate; hydrocortisone cypionate; hydrocortisone hemisuccinate; hydrocortisone probutate; hydrocortisone sodium phosphate; hydrocortisone sodium succinate; hydrocortisone valerate; hydroxyprogesterone; inokosterone; isoflupredone; isoflupredone acetate; isoprednidene; meclorisone; mecortolon; medrogestone; medroxyprogesterone; medrysone; megestrol; megestrol acetate; melengestrol; meprednisone; methandrostenolone; methylprednisolone; methylprednisolone aceponate; methylprednisolone acetate; methylprednisolone hemisuccinate; methylprednisolone sodium succinate; methyltestosterone; metribolone; mometasone; mometasone furoate; mometasone furoate monohydrate; nisone; nomegestrol; norgestomet; norvinisterone; oxymesterone; paramethasone; paramethasone acetate; ponasterone; prednisolamate; prednisolone; prednisolone 21-hemisuccinate; prednisolone acetate; prednisolone farnesylate; prednisolone hemisuccinate; prednisolone-21(beta-D-glucuronide); prednisolone metasulphobenzoate; prednisolone sodium phosphate; prednisolone steaglate; prednisolone tebutate; prednisolone tetrahydrophthalate; prednisone; prednival; prednylidene; pregnenolone; procinonide; tralonide; progesterone; promegestone; rhapontisterone; rimexolone; roxibolone; rubrosterone; stizophyllin; tixocortol; topterone; triamcinolone; triamcinolone acetonide; triamcinolone acetonide 21-palmitate; triamcinolone diacetate; triamcinolone hexacetonide; trimegestone; turkesterone; or wortmannin.

3. The method of claim 2, wherein said corticosteroid is fludrocortisone, prednisone, or prednisolone.

4. The method of claim 1, wherein said dipyridamole is administered systemically.

5. The method of claim 4, wherein said dipyridamole is administered orally or intravenously.

6. The method of claim 1, wherein said dipyridamole and said corticosteroid are administered within ten days of each other.

7. The method of claim 6, wherein said dipyridamole and said corticosteroid are administered within five days of each other.

8. The method of claim 7, wherein said dipyridamole and said corticosteroid are administered within twenty-four hours of each other.

9. The method of claim 8, wherein said dipyridamole and said corticosteroid are administered simultaneously.

10. The method of claim 9, wherein said dipyridamole and said corticosteroid are administered in the same pharmaceutical formulation.

11. A method for treating a patient who has osteoarthritis, said method comprising administering to said patient a composition consisting of active ingredients and excipients, wherein said active ingredients consist of a corticosteroid and dipyridamole
in an amount and for a duration sufficient to treat said patient.

12. The method of claim 11, wherein said corticosteroid is 11-alpha,17-alpha,21-trihydroxypregn-4-ene-3,20-dione; 11-beta,16-alpha,17,21-tetrahydroxypregn-4-ene-3,20-dione; 11-beta,16-alpha,17,21-tetrahydroxypregn-1,4-diene-3,20-dione; 11-beta,17-alpha,21-trihydroxy-6-alpha-methylpregn-4-ene-3,20-dione; 11-dehydrocorticosterone; 11-deoxycortisol; 11-hydroxy-1,4-androstadiene-3,17-dione; 11-ketotestosterone; 14-hydroxyandrost-4-ene-3,6,17-trione; 15,17-dihydroxyprogesterone; 16-methylhydrocortisone; 17,21-dihydroxy-16-alpha-methylpregna-1,4,9(11)-triene-3,20-dione; 17-alpha-hydroxypregn-4-ene-3,20-dione; 17-alpha-hydroxypregnenolone; 17-hydroxy-16-beta-methyl-5-beta-pregn-9(11)-ene-3,20-dione; 17-hydroxy-4,6,8(14)-pregnatriene-3,20-dione; 17-hydroxypregna-4,9(11)-diene-3,20-dione; 18-hydroxycorticosterone; 18-hydroxycortisone; 18-oxocortisol; 21-deoxyaldosterone; 21-deoxycortisone; 2-deoxyecdysone; 2-methylcortisone; 3-dehydroecdysone; 4-pregnene-17-alpha,20-beta, 21-triol-3,11-dione; 6,17,20-trihydroxypregn-4-ene-3-one; 6-alpha-hydroxycortisol; 6-alpha-fluoroprednisolone, 6-alpha-methylprednisolone, 6-alpha-methylprednisolone 21-acetate, 6-alpha-methylprednisolone 21-hemisuccinate sodium salt, 6-beta-hydroxycortisol, 6-alpha, 9-alpha-difluoroprednisolone 21-acetate 17-butyrate, 6-hydroxycorticosterone; 6-hydroxydexamethasone; 6-hydroxyprednisolone; 9-fluorocortisone; alclometasone dipropionate; aldosterone; algestone; alphaderm; amadinone; amcinonide; anagestone; androstenedione; anecortave acetate; beclomethasone; beclomethasone dipropionate; beclomethasone dipropionate monohydrate; betamethasone 17-valerate; betamethasone sodium acetate; betamethasone sodium phosphate; betamethasone valerate; bolasterone; budesonide; calusterone; chlormadinone; chloroprednisone; chloroprednisone acetate; cholesterol; clobetasol; clobetasol propionate; clobetasone; clocortolone; clocortolone pivalate; clogestone; cloprednol; corticosterone; cortisol; cortisol acetate; cortisol butyrate; cortisol cypionate; cortisol octanoate; cortisol sodium phosphate; cortisol sodium succinate; cortisol valerate; cortisone; cortisone acetate; cortodoxone; daturaolone; deflazacort, 21-deoxycortisol, dehydroepiandrosterone; delmadinone; deoxycorticosterone; deprodone; descinolone; desonide; desoximethasone; dexafen; dexamethasone; dexamethasone 21-acetate; dexamethasone acetate; dexamethasone sodium phosphate; dichlorisone; diflorasone; diflorasone diacetate; diflucortolone; dihydroelatericin a; domoprednate; doxibetasol; ecdysone; ecdysterone; endrysone; enoxolone; flucinolone; fludrocortisone; fludrocortisone acetate; flugestone; flumethasone; flumethasone pivalate; flumoxonide; flunisolide; fluocinolone; fluocinolone acetonide; fluocinonide; 9-fluorocortisone; fluocortolone; fluorohydroxyandrostenedione; fluorometholone; fluorometholone acetate; fluoxymesterone; fluprednidene; fluprednisolone; flurandrenolide; fluticasone; fluticasone propionate; formebolone; formestane; formocortal; gestonorone; glyderinine; halcinonide; hyrcanoside; halometasone; halopredone; haloprogesterone; hydrocortisone; hydrocortisone 21-butyrate; hydrocortisone aceponate; hydrocortisone acetate; hydrocortisone buteprate; hydrocortisone butyrate; hydrocortisone cypionate; hydrocortisone hemisuccinate; hydrocortisone probutate; hydrocortisone sodium phosphate; hydrocortisone sodium succinate; hydrocortisone valerate; hydroxyprogesterone; inokosterone; isoflupredone; isoflupredone acetate; isoprednidene; meclorisone; mecortolon; medrogestone; medroxyprogesterone; medrysone; megestrol; megestrol acetate; melengestrol; meprednisone; methandrostenolone; methylprednisolone; methylprednisolone aceponate; methylprednisolone acetate; methylprednisolone hemisuccinate; methylprednisolone sodium succinate; methyltestosterone; metribolone; mometasone; mometasone furoate; mometasone furoate monohydrate; nisone; nomegestrol; norgestomet; norvinisterone; oxymesterone; paramethasone; paramethasone acetate; ponasterone; prednisolamate; prednisolone; prednisolone 21-hemisuccinate; prednisolone acetate; prednisolone farnesylate; prednisolone hemisuccinate; prednisolone-21(beta-D-glucuronide); prednisolone metasulphobenzoate; prednisolone sodium phosphate; prednisolone steaglate; prednisolone tebutate; prednisolone tetrahydrophthalate; prednisone; prednival; prednylidene; pregnenolone; procinonide; tralonide; progesterone; promegestone; rhapontisterone; rimexolone; roxibolone; rubrosterone; stizophyllin; tixocortol; topterone; triamcinolone; triamcinolone acetonide; triamcinolone acetonide 21-palmitate; triamcinolone diacetate; triamcinolone hexacetonide; trimegestone; turkesterone; or wortmannin.

13. The method of claim 12, wherein said corticosteroid is fludrocortisone, prednisone, or prednisolone.

14. The method of claim 11, wherein said composition is administered systemically.

15. The method of claim 14, wherein said composition is administered orally or intravenously.

16. A method for treating a patient who has osteoarthritis said method consisting essentially of systemically administering to said patient a composition comprising dipyridamole and a corticosteroid in an amount and for a duration sufficient to treat said patient.

17. The method of claim 16, wherein said corticosteroid is fludrocortisone, prednisone, or prednisolone.

18. The method of claim 16, wherein said composition consists of active ingredients and excipients, wherein said active ingredients consist of a corticosteroid and dipyridamole.

19. The method of claim 18, wherein said corticosteroid is fludrocortisone, prednisone, or prednisolone.

20. The method of claim 19, wherein said composition is administered orally or intravenously.

21. The method of claim 5, wherein said dipyridamole is administered orally.

22. The method of claim 15, wherein said composition is administered orally.

* * * * *